United States Patent
Grifantini et al.

(10) Patent No.: US 10,359,428 B2
(45) Date of Patent: Jul. 23, 2019

(54) TUMOR MARKER, MONOCLONAL ANTIBODIES AND METHODS OF USE THEREOF

(71) Applicant: Externautics S.p.A., Siena (IT)

(72) Inventors: Renata Grifantini, Siena (IT); Piero Pileri, Siena (IT); Susanna Campagnoli, Siena (IT); Alberto Grandi, Siena (IT); Matteo Parri, Siena (IT); Jin Boquan, Xi'an (CN)

(73) Assignee: EXTERNAUTICS S.P.A., Siena (IT)

( * ) Notice: Subject to any disclaimer, the term of this patent is extended or adjusted under 35 U.S.C. 154(b) by 0 days.

(21) Appl. No.: 14/897,654

(22) PCT Filed: Jun. 13, 2014

(86) PCT No.: PCT/EP2014/062419
§ 371 (c)(1),
(2) Date: Dec. 11, 2015

(87) PCT Pub. No.: WO2014/198919
PCT Pub. Date: Dec. 18, 2014

(65) Prior Publication Data
US 2016/0131656 A1    May 12, 2016

(30) Foreign Application Priority Data
Jun. 14, 2013  (EP) .................. 13172028

(51) Int. Cl.
C07K 16/30   (2006.01)
G01N 33/574  (2006.01)
A61K 39/00   (2006.01)
A61K 47/68   (2017.01)

(52) U.S. Cl.
CPC .... *G01N 33/57484* (2013.01); *A61K 39/0011* (2013.01); *A61K 47/6843* (2017.08); *C07K 16/30* (2013.01); *C07K 16/3046* (2013.01); *C07K 16/3069* (2013.01); *G01N 33/57419* (2013.01); *A61K 2039/55505* (2013.01); *C07K 2317/21* (2013.01); *C07K 2317/24* (2013.01); *C07K 2317/34* (2013.01); *C07K 2317/54* (2013.01); *C07K 2317/55* (2013.01); *C07K 2317/565* (2013.01); *C07K 2317/622* (2013.01); *C07K 2317/626* (2013.01); *C07K 2317/77* (2013.01)

(58) Field of Classification Search
None
See application file for complete search history.

(56) References Cited

FOREIGN PATENT DOCUMENTS

WO    2001012781 A1    2/2001

OTHER PUBLICATIONS

Sadeqzadeh ( Journal of Biological Chemistry (2011) vol. 286, pp. 18181-28191).*
Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
C.E. De Bock, et al, "The Fat1 cadherin is overexpressed and an independent prognostic factor for survival in paired diagnosis-relapse samples of precursor B-cell acute lymphoblastic leukemia", Leukemia, vol. 26, No. 5, May 1, 2012, pp. 918-926.
International Search Report and Written Opinion of PCT/EP2014/062419 dated Feb. 10, 2015.
Invitation to pay additional fees for PCT/EP2014/062419 dated Oct. 16, 2014.
Luc Morris, et al, "Recurrent somatic mutation of FAT1 in multiple human cancers leads to aberrant Wnt activation", Nature Genetics, vol, 45, No. 3, Jan. 27, 2013 pp. 253-261.
Zhang et al. "Detection of differentially expressed genes in human colon carcinoma cells treated with a selective Cox-2 inhibitor", Oncogene, Nature Publishing Group, GB, vol. 20, No. 33, Jul. 27, 2001, pp. 4450-4456.
Search Report of PCT/EP2014/062419 dated Feb. 10, 2015.

* cited by examiner

*Primary Examiner* — Nelson B Moseley, II
(74) *Attorney, Agent, or Firm* — Silvia Salvadori, P.C.; Silvia Salvadori

(57) ABSTRACT

Newly identified proteins as markers for the detection of colon, ovary, kidney, esophagus and prostate tumors, or as therapeutic targets for their treatment; affinity ligands and particularly antibodies capable of selectively interacting with the tumor markers and methods for tumor diagnosis and therapy using such antibodies.

10 Claims, 18 Drawing Sheets
Specification includes a Sequence Listing.

Colon Cancer

Normal Colon mAb 91.3 – 30' at 4°C + 1h at 37°C mAb91.3  mAb91.3 + peptide

SEQUENCE LISTING

```
<160> NUMBER OF SEQ ID NOS: 49

<210> SEQ ID NO 1
<211> LENGTH: 4588
<212> TYPE: PRT
<213> ORGANISM: Homo sapiens

<400> SEQUENCE: 1

Met Gly Arg His Leu Ala Leu Leu Leu Leu Leu Leu Leu Phe Gln
1               5                   10                  15

His Phe Gly Asp Ser Asp Gly Ser Gln Arg Leu Glu Gln Thr Pro Leu
                20                  25                  30

Gln Phe Thr His Leu Glu Tyr Asn Val Thr Val Gln Glu Asn Ser Ala
            35                  40                  45

Ala Lys Thr Tyr Val Gly His Pro Val Lys Met Gly Val Tyr Ile Thr
        50                  55                  60

His Pro Ala Trp Glu Val Arg Tyr Lys Ile Val Ser Gly Asp Ser Glu
65                  70                  75                  80

Asn Leu Phe Lys Ala Glu Glu Tyr Ile Leu Gly Asp Phe Cys Phe Leu
                85                  90                  95

Arg Ile Arg Thr Lys Gly Gly Asn Thr Ala Ile Leu Asn Arg Glu Val
            100                 105                 110

Lys Asp His Tyr Thr Leu Ile Val Lys Ala Leu Glu Lys Asn Thr Asn
        115                 120                 125

Val Glu Ala Arg Thr Lys Val Arg Val Gln Val Leu Asp Thr Asn Asp
    130                 135                 140

Leu Arg Pro Leu Phe Ser Pro Thr Ser Tyr Ser Val Ser Leu Pro Glu
145                 150                 155                 160

Asn Thr Ala Ile Arg Thr Ser Ile Ala Arg Val Ser Ala Thr Asp Ala
                165                 170                 175

Asp Ile Gly Thr Asn Gly Glu Phe Tyr Tyr Ser Phe Lys Asp Arg Thr
            180                 185                 190

Asp Met Phe Ala Ile His Pro Thr Ser Gly Val Ile Val Leu Thr Gly
        195                 200                 205

Arg Leu Asp Tyr Leu Glu Thr Lys Leu Tyr Glu Met Glu Ile Leu Ala
    210                 215                 220

Ala Asp Arg Gly Met Lys Leu Tyr Gly Ser Ser Gly Ile Ser Ser Met
225                 230                 235                 240

Ala Lys Leu Thr Val His Ile Glu Gln Ala Asn Glu Cys Ala Pro Val
                245                 250                 255
```

```
Ile Thr Ala Val Thr Leu Ser Pro Ser Glu Leu Asp Arg Asp Pro Ala
            260                 265                 270

Tyr Ala Ile Val Thr Val Asp Asp Cys Asp Gln Gly Ala Asn Gly Asp
            275                 280                 285

Ile Ala Ser Leu Ser Ile Val Ala Gly Asp Leu Leu Gln Gln Phe Arg
            290                 295                 300

Thr Val Arg Ser Phe Pro Gly Ser Lys Glu Tyr Lys Val Lys Ala Ile
305                 310                 315                 320

Gly Gly Ile Asp Trp Asp Ser His Pro Phe Gly Tyr Asn Leu Thr Leu
            325                 330                 335

Gln Ala Lys Asp Lys Gly Thr Pro Pro Gln Phe Ser Ser Val Lys Val
            340                 345                 350

Ile His Val Thr Ser Pro Gln Phe Lys Ala Gly Pro Val Lys Phe Glu
            355                 360                 365

Lys Asp Val Tyr Arg Ala Glu Ile Ser Glu Phe Ala Pro Pro Asn Thr
            370                 375                 380

Pro Val Val Met Val Lys Ala Ile Pro Ala Tyr Ser His Leu Arg Tyr
385                 390                 395                 400

Val Phe Lys Ser Thr Pro Gly Lys Ala Lys Phe Ser Leu Asn Tyr Asn
            405                 410                 415

Thr Gly Leu Ile Ser Ile Leu Glu Pro Val Lys Arg Gln Gln Ala Ala
            420                 425                 430

His Phe Glu Leu Glu Val Thr Thr Ser Asp Arg Lys Ala Ser Thr Lys
            435                 440                 445

Val Leu Val Lys Val Leu Gly Ala Asn Ser Asn Pro Pro Glu Phe Thr
450                 455                 460

Gln Thr Ala Tyr Lys Ala Ala Phe Asp Glu Asn Val Pro Ile Gly Thr
465                 470                 475                 480

Thr Val Met Ser Leu Ser Ala Val Asp Pro Asp Glu Gly Glu Asn Gly
            485                 490                 495

Tyr Val Thr Tyr Ser Ile Ala Asn Leu Asn His Val Pro Phe Ala Ile
            500                 505                 510

Asp His Phe Thr Gly Ala Val Ser Thr Ser Glu Asn Leu Asp Tyr Glu
            515                 520                 525

Leu Met Pro Arg Val Tyr Thr Leu Arg Ile Arg Ala Ser Asp Trp Gly
            530                 535                 540

Leu Pro Tyr Arg Arg Glu Val Glu Val Leu Ala Thr Ile Thr Leu Asn
545                 550                 555                 560

Asn Leu Asn Asp Asn Thr Pro Leu Phe Glu Lys Ile Asn Cys Glu Gly
            565                 570                 575

Thr Ile Pro Arg Asp Leu Gly Val Gly Glu Gln Ile Thr Thr Val Ser
            580                 585                 590

Ala Ile Asp Ala Asp Glu Leu Gln Leu Val Gln Tyr Gln Ile Glu Ala
            595                 600                 605

Gly Asn Glu Leu Asp Phe Phe Ser Leu Asn Pro Asn Ser Gly Val Leu
            610                 615                 620

Ser Leu Lys Arg Ser Leu Met Asp Gly Leu Gly Ala Lys Val Ser Phe
625                 630                 635                 640

His Ser Leu Arg Ile Thr Ala Thr Asp Gly Glu Asn Phe Ala Thr Pro
            645                 650                 655

Leu Tyr Ile Asn Ile Thr Val Ala Ala Ser His Lys Leu Val Asn Leu
            660                 665                 670
```

```
Gln Cys Glu Glu Thr Gly Val Ala Lys Met Leu Ala Glu Lys Leu Leu
            675                 680                 685

Gln Ala Asn Lys Leu His Asn Gln Gly Glu Val Glu Asp Ile Phe Phe
690                 695                 700

Asp Ser His Ser Val Asn Ala His Ile Pro Gln Phe Arg Ser Thr Leu
705                 710                 715                 720

Pro Thr Gly Ile Gln Val Lys Glu Asn Gln Pro Val Gly Ser Ser Val
            725                 730                 735

Ile Phe Met Asn Ser Thr Asp Leu Asp Thr Gly Phe Asn Gly Lys Leu
                740                 745                 750

Val Tyr Ala Val Ser Gly Gly Asn Glu Asp Ser Cys Phe Met Ile Asp
            755                 760                 765

Met Glu Thr Gly Met Leu Lys Ile Leu Ser Pro Leu Asp Arg Glu Thr
    770                 775                 780

Thr Asp Lys Tyr Thr Leu Asn Ile Thr Val Tyr Asp Leu Gly Ile Pro
785                 790                 795                 800

Gln Lys Ala Ala Trp Arg Leu Leu His Val Val Val Asp Ala Asn
            805                 810                 815

Asp Asn Pro Pro Glu Phe Leu Gln Ser Tyr Phe Val Glu Val Ser
                820                 825                 830

Glu Asp Lys Glu Val His Ser Glu Ile Ile Gln Val Glu Ala Thr Asp
    835                 840                 845

Lys Asp Leu Gly Pro Asn Gly His Val Thr Tyr Ser Ile Val Thr Asp
    850                 855                 860

Thr Asp Thr Phe Ser Ile Asp Ser Val Thr Gly Val Val Asn Ile Ala
865                 870                 875                 880

Arg Pro Leu Asp Arg Glu Leu Gln His Glu His Ser Leu Lys Ile Glu
            885                 890                 895

Ala Arg Asp Gln Ala Arg Glu Glu Pro Gln Leu Phe Ser Thr Val Val
                900                 905                 910

Val Lys Val Ser Leu Glu Asp Val Asn Asp Asn Pro Pro Thr Phe Ile
    915                 920                 925

Pro Pro Asn Tyr Arg Val Lys Val Arg Glu Asp Leu Pro Glu Gly Thr
    930                 935                 940

Val Ile Met Trp Leu Glu Ala His Asp Pro Asp Leu Gly Gln Ser Gly
945                 950                 955                 960

Gln Val Arg Tyr Ser Leu Leu Asp His Gly Glu Gly Asn Phe Asp Val
            965                 970                 975

Asp Lys Leu Ser Gly Ala Val Arg Ile Val Gln Gln Leu Asp Phe Glu
            980                 985                 990

Lys Lys Gln Val Tyr Asn Leu Thr Val Arg Ala Lys Asp Lys Gly Lys
            995                 1000                1005

Pro Val Ser Leu Ser Ser Thr Cys Tyr Val Glu Val Glu Val Val
    1010                1015                1020

Asp Val Asn Glu Asn Leu His Pro Pro Val Phe Ser Ser Phe Val
    1025                1030                1035

Glu Lys Gly Thr Val Lys Glu Asp Ala Pro Val Gly Ser Leu Val
    1040                1045                1050

Met Thr Val Ser Ala His Asp Glu Asp Ala Arg Arg Asp Gly Glu
    1055                1060                1065

Ile Arg Tyr Ser Ile Arg Asp Gly Ser Gly Val Gly Val Phe Lys
    1070                1075                1080

Ile Gly Glu Glu Thr Gly Val Ile Glu Thr Ser Asp Arg Leu Asp
```

```
              1085              1090              1095
Arg Glu Ser Thr Ser His Tyr Trp Leu Thr Val Phe Ala Thr Asp
    1100              1105              1110
Gln Gly Val Val Pro Leu Ser Ser Phe Ile Glu Ile Tyr Ile Glu
    1115              1120              1125
Val Glu Asp Val Asn Asp Asn Ala Pro Gln Thr Ser Glu Pro Val
    1130              1135              1140
Tyr Tyr Pro Glu Ile Met Glu Asn Ser Pro Lys Asp Val Ser Val
    1145              1150              1155
Val Gln Ile Glu Ala Phe Asp Pro Asp Ser Ser Asn Asp Lys
    1160              1165              1170
Leu Met Tyr Lys Ile Thr Ser Gly Asn Pro Gln Gly Phe Phe Ser
    1175              1180              1185
Ile His Pro Lys Thr Gly Leu Ile Thr Thr Thr Ser Arg Lys Leu
    1190              1195              1200
Asp Arg Glu Gln Gln Asp Glu His Ile Leu Glu Val Thr Val Thr
    1205              1210              1215
Asp Asn Gly Ser Pro Pro Lys Ser Thr Ile Ala Arg Val Ile Val
    1220              1225              1230
Lys Ile Leu Asp Glu Asn Asp Asn Lys Pro Gln Phe Leu Gln Lys
    1235              1240              1245
Phe Tyr Lys Ile Arg Leu Pro Glu Arg Glu Lys Pro Asp Arg Glu
    1250              1255              1260
Arg Asn Ala Arg Arg Glu Pro Leu Tyr His Val Ile Ala Thr Asp
    1265              1270              1275
Lys Asp Glu Gly Pro Asn Ala Glu Ile Ser Tyr Ser Ile Glu Asp
    1280              1285              1290
Gly Asn Glu His Gly Lys Phe Phe Ile Glu Pro Lys Thr Gly Val
    1295              1300              1305
Val Ser Ser Lys Arg Phe Ser Ala Ala Gly Glu Tyr Asp Ile Leu
    1310              1315              1320
Ser Ile Lys Ala Val Asp Asn Gly Arg Pro Gln Lys Ser Ser Thr
    1325              1330              1335
Thr Arg Leu His Ile Glu Trp Ile Ser Lys Pro Lys Pro Ser Leu
    1340              1345              1350
Glu Pro Ile Ser Phe Glu Glu Ser Phe Phe Thr Phe Thr Val Met
    1355              1360              1365
Glu Ser Asp Pro Val Ala His Met Ile Gly Val Ile Ser Val Glu
    1370              1375              1380
Pro Pro Gly Ile Pro Leu Trp Phe Asp Ile Thr Gly Gly Asn Tyr
    1385              1390              1395
Asp Ser His Phe Asp Val Asp Lys Gly Thr Gly Thr Ile Ile Val
    1400              1405              1410
Ala Lys Pro Leu Asp Ala Glu Gln Lys Ser Asn Tyr Asn Leu Thr
    1415              1420              1425
Val Glu Ala Thr Asp Gly Thr Thr Thr Ile Leu Thr Gln Val Phe
    1430              1435              1440
Ile Lys Val Ile Asp Thr Asn Asp His Arg Pro Gln Phe Ser Thr
    1445              1450              1455
Ser Lys Tyr Glu Val Val Ile Pro Glu Asp Thr Ala Pro Glu Thr
    1460              1465              1470
Glu Ile Leu Gln Ile Ser Ala Val Asp Gln Asp Glu Lys Asn Lys
    1475              1480              1485
```

```
Leu Ile Tyr Thr Leu Gln Ser    Ser Arg Asp Pro Leu   Ser Leu Lys
    1490                1495                1500

Lys Phe Arg Leu Asp Pro Ala    Thr Gly Ser Leu Tyr   Thr Ser Glu
    1505                1510                1515

Lys Leu Asp His Glu Ala Val    His Gln His Thr Leu   Thr Val Met
    1520                1525                1530

Val Arg Asp Gln Asp Val Pro    Val Lys Arg Asn Phe   Ala Arg Ile
    1535                1540                1545

Val Val Asn Val Ser Asp Thr    Asn Asp His Ala Pro   Trp Phe Thr
    1550                1555                1560

Ala Ser Ser Tyr Lys Gly Arg    Val Tyr Glu Ser Ala   Ala Val Gly
    1565                1570                1575

Ser Val Val Leu Gln Val Thr    Ala Leu Asp Lys Asp   Lys Gly Lys
    1580                1585                1590

Asn Ala Glu Val Leu Tyr Ser    Ile Glu Ser Gly Asn   Ile Gly Asn
    1595                1600                1605

Ser Phe Met Ile Asp Pro Val    Leu Gly Ser Ile Lys   Thr Ala Lys
    1610                1615                1620

Glu Leu Asp Arg Ser Asn Gln    Ala Glu Tyr Asp Leu   Met Val Lys
    1625                1630                1635

Ala Thr Asp Lys Gly Ser Pro    Pro Met Ser Glu Ile   Thr Ser Val
    1640                1645                1650

Arg Ile Phe Val Thr Ile Ala    Asp Asn Ala Ser Pro   Lys Phe Thr
    1655                1660                1665

Ser Lys Glu Tyr Ser Val Glu    Leu Ser Glu Thr Val   Ser Ile Gly
    1670                1675                1680

Ser Phe Val Gly Met Val Thr    Ala His Ser Gln Ser   Ser Val Val
    1685                1690                1695

Tyr Glu Ile Lys Asp Gly Asn    Thr Gly Asp Ala Phe   Asp Ile Asn
    1700                1705                1710

Pro His Ser Gly Thr Ile Ile    Thr Gln Lys Ala Leu   Asp Phe Glu
    1715                1720                1725

Thr Leu Pro Ile Tyr Thr Leu    Ile Ile Gln Gly Thr   Asn Met Ala
    1730                1735                1740

Gly Leu Ser Thr Asn Thr Thr    Val Leu Val His Leu   Gln Asp Glu
    1745                1750                1755

Asn Asp Asn Ala Pro Val Phe    Met Gln Ala Glu Tyr   Thr Gly Leu
    1760                1765                1770

Ile Ser Glu Ser Ala Ser Ile    Asn Ser Val Val Leu   Thr Asp Arg
    1775                1780                1785

Asn Val Pro Leu Val Ile Arg    Ala Ala Asp Ala Asp   Lys Asp Ser
    1790                1795                1800

Asn Ala Leu Leu Val Tyr His    Ile Val Glu Pro Ser   Val His Thr
    1805                1810                1815

Tyr Phe Ala Ile Asp Ser Ser    Thr Gly Ala Ile His   Thr Val Leu
    1820                1825                1830

Ser Leu Asp Tyr Glu Glu Thr    Ser Ile Phe His Phe   Thr Val Gln
    1835                1840                1845

Val His Asp Met Gly Thr Pro    Arg Leu Phe Ala Glu   Tyr Ala Ala
    1850                1855                1860

Asn Val Thr Val His Val Ile    Asp Ile Asn Asp Cys   Pro Pro Val
    1865                1870                1875
```

```
Phe Ala Lys Pro Leu Tyr Glu Ala Ser Leu Leu Pro Thr Tyr
        1880                1885            1890

Lys Gly Val Lys Val Ile Thr Val Asn Ala Thr Asp Ala Asp Ser
    1895                1900            1905

Ser Ala Phe Ser Gln Leu Ile Tyr Ser Ile Thr Glu Gly Asn Ile
    1910                1915            1920

Gly Glu Lys Phe Ser Met Asp Tyr Lys Thr Gly Ala Leu Thr Val
    1925                1930            1935

Gln Asn Thr Thr Gln Leu Arg Ser Arg Tyr Glu Leu Thr Val Arg
    1940                1945            1950

Ala Ser Asp Gly Arg Phe Ala Gly Leu Thr Ser Val Lys Ile Asn
    1955                1960            1965

Val Lys Glu Ser Lys Glu Ser His Leu Lys Phe Thr Gln Asp Val
    1970                1975            1980

Tyr Ser Ala Val Val Lys Glu Asn Ser Thr Glu Ala Glu Thr Leu
    1985                1990            1995

Ala Val Ile Thr Ala Ile Gly Asn Pro Ile Asn Glu Pro Leu Phe
    2000                2005            2010

Tyr His Ile Leu Asn Pro Asp Arg Arg Phe Lys Ile Ser Arg Thr
    2015                2020            2025

Ser Gly Val Leu Ser Thr Thr Gly Thr Pro Phe Asp Arg Glu Gln
    2030                2035            2040

Gln Glu Ala Phe Asp Val Val Val Glu Val Thr Glu Glu His Lys
    2045                2050            2055

Pro Ser Ala Val Ala His Val Val Val Lys Val Ile Val Glu Asp
    2060                2065            2070

Gln Asn Asp Asn Ala Pro Val Phe Val Asn Leu Pro Tyr Tyr Ala
    2075                2080            2085

Val Val Lys Val Asp Thr Glu Val Gly His Val Ile Arg Tyr Val
    2090                2095            2100

Thr Ala Val Asp Arg Asp Ser Gly Arg Asn Gly Glu Val His Tyr
    2105                2110            2115

Tyr Leu Lys Glu His His Glu His Phe Gln Ile Gly Pro Leu Gly
    2120                2125            2130

Glu Ile Ser Leu Lys Lys Gln Phe Glu Leu Asp Thr Leu Asn Lys
    2135                2140            2145

Glu Tyr Leu Val Thr Val Val Ala Lys Asp Gly Gly Asn Pro Ala
    2150                2155            2160

Phe Ser Ala Glu Val Ile Val Pro Ile Thr Val Met Asn Lys Ala
    2165                2170            2175

Met Pro Val Phe Glu Lys Pro Phe Tyr Ser Ala Glu Ile Ala Glu
    2180                2185            2190

Ser Ile Gln Val His Ser Pro Val Val His Val Gln Ala Asn Ser
    2195                2200            2205

Pro Glu Gly Leu Lys Val Phe Tyr Ser Ile Thr Asp Gly Asp Pro
    2210                2215            2220

Phe Ser Gln Phe Thr Ile Asn Phe Asn Thr Gly Val Ile Asn Val
    2225                2230            2235

Ile Ala Pro Leu Asp Phe Glu Ala His Pro Ala Tyr Lys Leu Ser
    2240                2245            2250

Ile Arg Ala Thr Asp Ser Leu Thr Gly Ala His Ala Glu Val Phe
    2255                2260            2265

Val Asp Ile Ile Val Asp Asp Ile Asn Asp Asn Pro Pro Val Phe
```

-continued

```
                  2270                2275                2280
Ala Gln Gln Ser Tyr Ala Val Thr Leu Ser Glu Ala Ser Val Ile
        2285                2290                2295
Gly Thr Ser Val Val Gln Val Arg Ala Thr Asp Ser Asp Ser Glu
        2300                2305                2310
Pro Asn Arg Gly Ile Ser Tyr Gln Met Phe Gly Asn His Ser Lys
        2315                2320                2325
Ser His Asp His Phe His Val Asp Ser Ser Thr Gly Leu Ile Ser
        2330                2335                2340
Leu Leu Arg Thr Leu Asp Tyr Glu Gln Ser Arg Gln His Thr Ile
        2345                2350                2355
Phe Val Arg Ala Val Asp Gly Gly Met Pro Thr Leu Ser Ser Asp
        2360                2365                2370
Val Ile Val Thr Val Asp Val Thr Asp Leu Asn Asp Asn Pro Pro
        2375                2380                2385
Leu Phe Glu Gln Gln Ile Tyr Glu Ala Arg Ile Ser Glu His Ala
        2390                2395                2400
Pro His Gly His Phe Val Thr Cys Val Lys Ala Tyr Asp Ala Asp
        2405                2410                2415
Ser Ser Asp Ile Asp Lys Leu Gln Tyr Ser Ile Leu Ser Gly Asn
        2420                2425                2430
Asp His Lys His Phe Val Ile Asp Ser Ala Thr Gly Ile Ile Thr
        2435                2440                2445
Leu Ser Asn Leu His Arg His Ala Leu Lys Pro Phe Tyr Ser Leu
        2450                2455                2460
Asn Leu Ser Val Ser Asp Gly Val Phe Arg Ser Ser Thr Gln Val
        2465                2470                2475
His Val Thr Val Ile Gly Gly Asn Leu His Ser Pro Ala Phe Leu
        2480                2485                2490
Gln Asn Glu Tyr Glu Val Glu Leu Ala Glu Asn Ala Pro Leu His
        2495                2500                2505
Thr Leu Val Met Glu Val Lys Thr Thr Asp Gly Asp Ser Gly Ile
        2510                2515                2520
Tyr Gly His Val Thr Tyr His Ile Val Asn Asp Phe Ala Lys Asp
        2525                2530                2535
Arg Phe Tyr Ile Asn Glu Arg Gly Gln Ile Phe Thr Leu Glu Lys
        2540                2545                2550
Leu Asp Arg Glu Thr Pro Ala Glu Lys Val Ile Ser Val Arg Leu
        2555                2560                2565
Met Ala Lys Asp Ala Gly Gly Lys Val Ala Phe Cys Thr Val Asn
        2570                2575                2580
Val Ile Leu Thr Asp Asp Asn Asp Asn Ala Pro Gln Phe Arg Ala
        2585                2590                2595
Thr Lys Tyr Glu Val Asn Ile Gly Ser Ser Ala Ala Lys Gly Thr
        2600                2605                2610
Ser Val Val Lys Val Leu Ala Ser Asp Ala Asp Glu Gly Ser Asn
        2615                2620                2625
Ala Asp Ile Thr Tyr Ala Ile Glu Ala Asp Ser Glu Ser Val Lys
        2630                2635                2640
Glu Asn Leu Glu Ile Asn Lys Leu Ser Gly Val Ile Thr Thr Lys
        2645                2650                2655
Glu Ser Leu Ile Gly Leu Glu Asn Glu Phe Phe Thr Phe Phe Val
        2660                2665                2670
```

```
Arg Ala Val Asp Asn Gly Ser Pro Ser Lys Glu Ser Val Val Leu
2675                2680                2685

Val Tyr Val Lys Ile Leu Pro Pro Glu Met Gln Leu Pro Lys Phe
2690                2695                2700

Ser Glu Pro Phe Tyr Thr Phe Thr Val Ser Glu Asp Val Pro Ile
2705                2710                2715

Gly Thr Glu Ile Asp Leu Ile Arg Ala Glu His Ser Gly Thr Val
2720                2725                2730

Leu Tyr Ser Leu Val Lys Gly Asn Thr Pro Glu Ser Asn Arg Asp
2735                2740                2745

Glu Ser Phe Val Ile Asp Arg Gln Ser Gly Arg Leu Lys Leu Glu
2750                2755                2760

Lys Ser Leu Asp His Glu Thr Thr Lys Trp Tyr Gln Phe Ser Ile
2765                2770                2775

Leu Ala Arg Cys Thr Gln Asp Asp His Glu Met Val Ala Ser Val
2780                2785                2790

Asp Val Ser Ile Gln Val Lys Asp Ala Asn Asp Asn Ser Pro Val
2795                2800                2805

Phe Glu Ser Ser Pro Tyr Glu Ala Phe Ile Val Glu Asn Leu Pro
2810                2815                2820

Gly Gly Ser Arg Val Ile Gln Ile Arg Ala Ser Asp Ala Asp Ser
2825                2830                2835

Gly Thr Asn Gly Gln Val Met Tyr Ser Leu Asp Gln Ser Gln Ser
2840                2845                2850

Val Glu Val Ile Glu Ser Phe Ala Ile Asn Met Glu Thr Gly Trp
2855                2860                2865

Ile Thr Thr Leu Lys Glu Leu Asp His Glu Lys Arg Asp Asn Tyr
2870                2875                2880

Gln Ile Lys Val Val Ala Ser Asp His Gly Glu Lys Ile Gln Leu
2885                2890                2895

Ser Ser Thr Ala Ile Val Asp Val Thr Val Thr Asp Val Asn Asp
2900                2905                2910

Ser Pro Pro Arg Phe Thr Ala Glu Ile Tyr Lys Gly Thr Val Ser
2915                2920                2925

Glu Asp Asp Pro Gln Gly Gly Val Ile Ala Ile Leu Ser Thr Thr
2930                2935                2940

Asp Ala Asp Ser Glu Glu Ile Asn Arg Gln Val Thr Tyr Phe Ile
2945                2950                2955

Thr Gly Gly Asp Pro Leu Gly Gln Phe Ala Val Glu Thr Ile Gln
2960                2965                2970

Asn Glu Trp Lys Val Tyr Val Lys Lys Pro Leu Asp Arg Glu Lys
2975                2980                2985

Arg Asp Asn Tyr Leu Leu Thr Ile Thr Ala Thr Asp Gly Thr Phe
2990                2995                3000

Ser Ser Lys Ala Ile Val Glu Val Lys Val Leu Asp Ala Asn Asp
3005                3010                3015

Asn Ser Pro Val Cys Glu Lys Thr Leu Tyr Ser Asp Thr Ile Pro
3020                3025                3030

Glu Asp Val Leu Pro Gly Lys Leu Ile Met Gln Ile Ser Ala Thr
3035                3040                3045

Asp Ala Asp Ile Arg Ser Asn Ala Glu Ile Thr Tyr Thr Leu Leu
3050                3055                3060
```

```
Gly Ser Gly Ala Glu Lys Phe Lys Leu Asn Pro Asp Thr Gly Glu
    3065            3070            3075

Leu Lys Thr Ser Thr Pro Leu Asp Arg Glu Glu Gln Ala Val Tyr
    3080            3085            3090

His Leu Leu Val Arg Ala Thr Asp Gly Gly Arg Phe Cys Gln
    3095            3100            3105

Ala Ser Ile Val Leu Thr Leu Glu Asp Val Asn Asp Asn Ala Pro
    3110            3115            3120

Glu Phe Ser Ala Asp Pro Tyr Ala Ile Thr Val Phe Glu Asn Thr
    3125            3130            3135

Glu Pro Gly Thr Leu Leu Thr Arg Val Gln Ala Thr Asp Ala Asp
    3140            3145            3150

Ala Gly Leu Asn Arg Lys Ile Leu Tyr Ser Leu Ile Asp Ser Ala
    3155            3160            3165

Asp Gly Gln Phe Ser Ile Asn Glu Leu Ser Gly Ile Ile Gln Leu
    3170            3175            3180

Glu Lys Pro Leu Asp Arg Glu Leu Gln Ala Val Tyr Thr Leu Ser
    3185            3190            3195

Leu Lys Ala Val Asp Gln Gly Leu Pro Arg Arg Leu Thr Ala Thr
    3200            3205            3210

Gly Thr Val Ile Val Ser Val Leu Asp Ile Asn Asp Asn Pro Pro
    3215            3220            3225

Val Phe Glu Tyr Arg Glu Tyr Gly Ala Thr Val Ser Glu Asp Ile
    3230            3235            3240

Leu Val Gly Thr Glu Val Leu Gln Val Tyr Ala Ala Ser Arg Asp
    3245            3250            3255

Ile Glu Ala Asn Ala Glu Ile Thr Tyr Ser Ile Ile Ser Gly Asn
    3260            3265            3270

Glu His Gly Lys Phe Ser Ile Asp Ser Lys Thr Gly Ala Val Phe
    3275            3280            3285

Ile Ile Glu Asn Leu Asp Tyr Glu Ser Ser His Glu Tyr Tyr Leu
    3290            3295            3300

Thr Val Glu Ala Thr Asp Gly Gly Thr Pro Ser Leu Ser Asp Val
    3305            3310            3315

Ala Thr Val Asn Val Asn Val Thr Asp Ile Asn Asp Asn Thr Pro
    3320            3325            3330

Val Phe Ser Gln Asp Thr Tyr Thr Thr Val Ile Ser Glu Asp Ala
    3335            3340            3345

Val Leu Glu Gln Ser Val Ile Thr Val Met Ala Asp Asp Ala Asp
    3350            3355            3360

Gly Pro Ser Asn Ser His Ile His Tyr Ser Ile Ile Asp Gly Asn
    3365            3370            3375

Gln Gly Ser Ser Phe Thr Ile Asp Pro Val Arg Gly Glu Val Lys
    3380            3385            3390

Val Thr Lys Leu Leu Asp Arg Glu Thr Ile Ser Gly Tyr Thr Leu
    3395            3400            3405

Thr Val Gln Ala Ser Asp Asn Gly Ser Pro Pro Arg Val Asn Thr
    3410            3415            3420

Thr Thr Val Asn Ile Asp Val Ser Asp Val Asn Asp Asn Ala Pro
    3425            3430            3435

Val Phe Ser Arg Gly Asn Tyr Ser Val Ile Ile Gln Glu Asn Lys
    3440            3445            3450

Pro Val Gly Phe Ser Val Leu Gln Leu Val Val Thr Asp Glu Asp
```

```
              3455                3460                3465
Ser  Ser  His  Asn  Gly  Pro  Pro  Phe  Phe  Phe  Thr  Ile  Val  Thr  Gly
     3470                3475                3480

Asn  Asp  Glu  Lys  Ala  Phe  Glu  Val  Asn  Pro  Gln  Gly  Val  Leu  Leu
     3485                3490                3495

Thr  Ser  Ser  Ala  Ile  Lys  Arg  Lys  Glu  Lys  Asp  His  Tyr  Leu  Leu
     3500                3505                3510

Gln  Val  Lys  Val  Ala  Asp  Asn  Gly  Lys  Pro  Gln  Leu  Ser  Ser  Leu
     3515                3520                3525

Thr  Tyr  Ile  Asp  Ile  Arg  Val  Ile  Glu  Glu  Ser  Ile  Tyr  Pro  Pro
     3530                3535                3540

Ala  Ile  Leu  Pro  Leu  Glu  Ile  Phe  Ile  Thr  Ser  Gly  Glu  Glu
     3545                3550                3555

Tyr  Ser  Gly  Gly  Val  Ile  Gly  Lys  Ile  His  Ala  Thr  Asp  Gln  Asp
     3560                3565                3570

Val  Tyr  Asp  Thr  Leu  Thr  Tyr  Ser  Leu  Asp  Pro  Gln  Met  Asp  Asn
     3575                3580                3585

Leu  Phe  Ser  Val  Ser  Ser  Thr  Gly  Gly  Lys  Leu  Ile  Ala  His  Lys
     3590                3595                3600

Lys  Leu  Asp  Ile  Gly  Gln  Tyr  Leu  Leu  Asn  Val  Ser  Val  Thr  Asp
     3605                3610                3615

Gly  Lys  Phe  Thr  Thr  Val  Ala  Asp  Ile  Thr  Val  His  Ile  Arg  Gln
     3620                3625                3630

Val  Thr  Gln  Glu  Met  Leu  Asn  His  Thr  Ile  Ala  Ile  Arg  Phe  Ala
     3635                3640                3645

Asn  Leu  Thr  Pro  Glu  Glu  Phe  Val  Gly  Asp  Tyr  Trp  Arg  Asn  Phe
     3650                3655                3660

Gln  Arg  Ala  Leu  Arg  Asn  Ile  Leu  Gly  Val  Arg  Arg  Asn  Asp  Ile
     3665                3670                3675

Gln  Ile  Val  Ser  Leu  Gln  Ser  Ser  Glu  Pro  His  Pro  His  Leu  Asp
     3680                3685                3690

Val  Leu  Leu  Phe  Val  Glu  Lys  Pro  Gly  Ser  Ala  Gln  Ile  Ser  Thr
     3695                3700                3705

Lys  Gln  Leu  Leu  His  Lys  Ile  Asn  Ser  Ser  Val  Thr  Asp  Ile  Glu
     3710                3715                3720

Glu  Ile  Ile  Gly  Val  Arg  Ile  Leu  Asn  Val  Phe  Gln  Lys  Leu  Cys
     3725                3730                3735

Ala  Gly  Leu  Asp  Cys  Pro  Trp  Lys  Phe  Cys  Asp  Glu  Lys  Val  Ser
     3740                3745                3750

Val  Asp  Glu  Ser  Val  Met  Ser  Thr  His  Ser  Thr  Ala  Arg  Leu  Ser
     3755                3760                3765

Phe  Val  Thr  Pro  Arg  His  His  Arg  Ala  Ala  Val  Cys  Leu  Cys  Lys
     3770                3775                3780

Glu  Gly  Arg  Cys  Pro  Pro  Val  His  His  Gly  Cys  Glu  Asp  Asp  Pro
     3785                3790                3795

Cys  Pro  Glu  Gly  Ser  Glu  Cys  Val  Ser  Asp  Pro  Trp  Glu  Glu  Lys
     3800                3805                3810

His  Thr  Cys  Val  Cys  Pro  Ser  Gly  Arg  Phe  Gly  Gln  Cys  Pro  Gly
     3815                3820                3825

Ser  Ser  Ser  Met  Thr  Leu  Thr  Gly  Asn  Ser  Tyr  Val  Lys  Tyr  Arg
     3830                3835                3840

Leu  Thr  Glu  Asn  Glu  Asn  Lys  Leu  Glu  Met  Lys  Leu  Thr  Met  Arg
     3845                3850                3855
```

-continued

```
Leu Arg Thr Tyr Ser Thr His Ala Val Val Met Tyr Ala Arg Gly
    3860                3865                3870

Thr Asp Tyr Ser Ile Leu Glu Ile His His Gly Arg Leu Gln Tyr
    3875                3880                3885

Lys Phe Asp Cys Gly Ser Gly Pro Gly Ile Val Ser Val Gln Ser
    3890                3895                3900

Ile Gln Val Asn Asp Gly Gln Trp His Ala Val Ala Leu Glu Val
    3905                3910                3915

Asn Gly Asn Tyr Ala Arg Leu Val Leu Asp Gln Val His Thr Ala
    3920                3925                3930

Ser Gly Thr Ala Pro Gly Thr Leu Lys Thr Leu Asn Leu Asp Asn
    3935                3940                3945

Tyr Val Phe Phe Gly Gly His Ile Arg Gln Gln Gly Thr Arg His
    3950                3955                3960

Gly Arg Ser Pro Gln Val Gly Asn Gly Phe Arg Gly Cys Met Asp
    3965                3970                3975

Ser Ile Tyr Leu Asn Gly Gln Glu Leu Pro Leu Asn Ser Lys Pro
    3980                3985                3990

Arg Ser Tyr Ala His Ile Glu Glu Ser Val Asp Val Ser Pro Gly
    3995                4000                4005

Cys Phe Leu Thr Ala Thr Glu Asp Cys Ala Ser Asn Pro Cys Gln
    4010                4015                4020

Asn Gly Gly Val Cys Asn Pro Ser Pro Ala Gly Gly Tyr Tyr Cys
    4025                4030                4035

Lys Cys Ser Ala Leu Tyr Ile Gly Thr His Cys Glu Ile Ser Val
    4040                4045                4050

Asn Pro Cys Ser Ser Lys Pro Cys Leu Tyr Gly Gly Thr Cys Val
    4055                4060                4065

Val Asp Asn Gly Gly Phe Val Cys Gln Cys Arg Gly Leu Tyr Thr
    4070                4075                4080

Gly Gln Arg Cys Gln Leu Ser Pro Tyr Cys Lys Asp Glu Pro Cys
    4085                4090                4095

Lys Asn Gly Gly Thr Cys Phe Asp Ser Leu Asp Gly Ala Val Cys
    4100                4105                4110

Gln Cys Asp Ser Gly Phe Arg Gly Glu Arg Cys Gln Ser Asp Ile
    4115                4120                4125

Asp Glu Cys Ser Gly Asn Pro Cys Leu His Gly Ala Leu Cys Glu
    4130                4135                4140

Asn Thr His Gly Ser Tyr His Cys Asn Cys Ser His Glu Tyr Arg
    4145                4150                4155

Gly Arg His Cys Glu Asp Ala Ala Pro Asn Gln Tyr Val Ser Thr
    4160                4165                4170

Pro Trp Asn Ile Gly Leu Ala Glu Gly Ile Gly Ile Val Val Phe
    4175                4180                4185

Val Ala Gly Ile Phe Leu Leu Val Val Val Phe Val Leu Cys Arg
    4190                4195                4200

Lys Met Ile Ser Arg Lys Lys Lys His Gln Ala Glu Pro Lys Asp
    4205                4210                4215

Lys His Leu Gly Pro Ala Thr Ala Phe Leu Gln Arg Pro Tyr Phe
    4220                4225                4230

Asp Ser Lys Leu Asn Lys Asn Ile Tyr Ser Asp Ile Pro Pro Gln
    4235                4240                4245
```

```
Val Pro Val Arg Pro Ile Ser Tyr Thr Pro Ser Ile Pro Ser Asp
    4250            4255                4260

Ser Arg Asn Asn Leu Asp Arg Asn Ser Phe Glu Gly Ser Ala Ile
4265                4270                4275

Pro Glu His Pro Glu Phe Ser Thr Phe Asn Pro Glu Ser Val His
        4280                4285                4290

Gly His Arg Lys Ala Val Ala Val Cys Ser Val Ala Pro Asn Leu
    4295                4300                4305

Pro Pro Pro Pro Ser Asn Ser Pro Ser Asp Ser Asp Ser Ile
4310                4315                4320

Gln Lys Pro Ser Trp Asp Phe Asp Tyr Asp Thr Lys Val Val Asp
    4325                4330                4335

Leu Asp Pro Cys Leu Ser Lys Lys Pro Leu Glu Lys Pro Ser
4340                4345                4350

Gln Pro Tyr Ser Ala Arg Glu Ser Leu Ser Glu Val Gln Ser Leu
    4355                4360                4365

Ser Ser Phe Gln Ser Glu Ser Cys Asp Asp Asn Gly Tyr His Trp
4370                4375                4380

Asp Thr Ser Asp Trp Met Pro Ser Val Pro Leu Pro Asp Ile Gln
    4385                4390                4395

Glu Phe Pro Asn Tyr Glu Val Ile Asp Glu Gln Thr Pro Leu Tyr
4400                4405                4410

Ser Ala Asp Pro Asn Ala Ile Asp Thr Asp Tyr Tyr Pro Gly Gly
    4415                4420                4425

Tyr Asp Ile Glu Ser Asp Phe Pro Pro Pro Glu Asp Phe Pro
4430                4435                4440

Ala Ala Asp Glu Leu Pro Pro Leu Pro Pro Glu Phe Ser Asn Gln
    4445                4450                4455

Phe Glu Ser Ile His Pro Pro Arg Asp Met Pro Ala Ala Gly Ser
4460                4465                4470

Leu Gly Ser Ser Ser Arg Asn Arg Gln Arg Phe Asn Leu Asn Gln
    4475                4480                4485

Tyr Leu Pro Asn Phe Tyr Pro Leu Asp Met Ser Glu Pro Gln Thr
4490                4495                4500

Lys Gly Thr Gly Glu Asn Ser Thr Cys Arg Glu Pro His Ala Pro
    4505                4510                4515

Tyr Pro Pro Gly Tyr Gln Arg His Phe Glu Ala Pro Ala Val Glu
4520                4525                4530

Ser Met Pro Met Ser Val Tyr Ala Ser Thr Ala Ser Cys Ser Asp
    4535                4540                4545

Val Ser Ala Cys Cys Glu Val Glu Ser Glu Val Met Met Ser Asp
4550                4555                4560

Tyr Glu Ser Gly Asp Asp Gly His Phe Glu Glu Val Thr Ile Pro
    4565                4570                4575

Pro Leu Asp Ser Gln Gln His Thr Glu Val
4580                4585

<210> SEQ ID NO 2
<211> LENGTH: 488
<212> TYPE: PRT
<213> ORGANISM: Homo sapiens

<400> SEQUENCE: 2

Met Gly Arg His Leu Ala Leu Leu Leu Leu Leu Leu Leu Phe Gln
1               5                   10                  15
```

His Phe Gly Asp Ser Asp Gly Ser Gln Arg Leu Glu Gln Thr Pro Leu
                20                  25                  30

Gln Phe Thr His Leu Glu Tyr Asn Val Thr Val Gln Glu Asn Ser Ala
            35                  40                  45

Ala Lys Thr Tyr Val Gly His Pro Val Lys Met Gly Val Tyr Ile Thr
        50                  55                  60

His Pro Ala Trp Glu Val Arg Tyr Lys Ile Val Ser Gly Asp Ser Glu
65                  70                  75                  80

Asn Leu Phe Lys Ala Glu Glu Tyr Ile Leu Gly Asp Phe Cys Phe Leu
                85                  90                  95

Arg Ile Arg Thr Lys Gly Gly Asn Thr Ala Ile Leu Asn Arg Glu Val
            100                 105                 110

Lys Asp His Tyr Thr Leu Ile Val Lys Ala Leu Glu Lys Asn Thr Asn
        115                 120                 125

Val Glu Ala Arg Thr Lys Val Arg Val Gln Val Leu Asp Thr Asn Asp
130                 135                 140

Leu Arg Pro Leu Phe Ser Pro Thr Ser Tyr Ser Val Ser Leu Pro Glu
145                 150                 155                 160

Asn Thr Ala Ile Arg Thr Ser Ile Ala Arg Val Ser Ala Thr Asp Ala
                165                 170                 175

Asp Ile Gly Thr Asn Gly Glu Phe Tyr Tyr Ser Phe Lys Asp Arg Thr
            180                 185                 190

Asp Met Phe Ala Ile His Pro Thr Ser Gly Val Ile Val Leu Thr Gly
        195                 200                 205

Arg Leu Asp Tyr Leu Glu Thr Lys Leu Tyr Glu Met Glu Ile Leu Ala
210                 215                 220

Ala Asp Arg Gly Met Lys Leu Tyr Gly Ser Ser Gly Ile Ser Ser Met
225                 230                 235                 240

Ala Lys Leu Thr Val His Ile Glu Gln Ala Asn Glu Cys Ala Pro Val
                245                 250                 255

Ile Thr Ala Val Thr Leu Ser Pro Ser Glu Leu Asp Arg Asp Pro Ala
            260                 265                 270

Tyr Ala Ile Val Thr Val Asp Asp Cys Asp Gln Gly Ala Asn Gly Asp
        275                 280                 285

Ile Ala Ser Leu Ser Ile Val Ala Gly Asp Leu Leu Gln Gln Phe Arg
290                 295                 300

Thr Val Arg Ser Phe Pro Gly Ser Lys Glu Tyr Lys Val Lys Ala Ile
305                 310                 315                 320

Gly Gly Ile Asp Trp Asp Ser His Pro Phe Gly Tyr Asn Leu Thr Leu
                325                 330                 335

Gln Ala Lys Asp Lys Gly Thr Pro Pro Gln Phe Ser Ser Val Lys Val
            340                 345                 350

Ile His Val Thr Ser Pro Gln Phe Lys Ala Gly Pro Val Lys Phe Glu
        355                 360                 365

Lys Asp Val Tyr Arg Ala Glu Ile Ser Glu Phe Ala Pro Pro Asn Thr
370                 375                 380

Pro Val Val Met Val Lys Ala Ile Pro Ala Tyr Ser His Leu Arg Tyr
385                 390                 395                 400

Val Phe Lys Ser Thr Pro Gly Lys Ala Lys Phe Ser Leu Asn Tyr Asn
                405                 410                 415

Thr Gly Leu Ile Ser Ile Leu Glu Pro Val Lys Arg Gln Gln Ala Ala
            420                 425                 430

```
His Phe Glu Leu Glu Val Thr Thr Ser Asp Arg Lys Ala Ser Thr Lys
                435                 440                 445

Val Leu Val Lys Val Leu Gly Ala Asn Ser Asn Pro Pro Glu Phe Thr
450                 455                 460

Gln Thr Ala Tyr Lys Ala Ala Phe Asp Glu Asn Val Pro Ile Gly Thr
465                 470                 475                 480

Thr Val Met Ser Leu Ser Ala Val
                485

<210> SEQ ID NO 3
<211> LENGTH: 368
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 3

Xaa Asp Ser Lys Leu Asn Lys Asn Ile Tyr Ser Asp Ile Pro Pro Gln
1               5                   10                  15

Val Pro Val Arg Pro Ile Ser Tyr Thr Pro Ser Ile Pro Ser Asp Ser
            20                  25                  30

Arg Asn Asn Leu Asp Arg Asn Ser Phe Glu Gly Ser Ala Ile Pro Glu
        35                  40                  45

His Pro Glu Phe Ser Thr Phe Asn Pro Glu Ser Val His Gly His Arg
    50                  55                  60

Lys Ala Val Ala Val Cys Ser Val Ala Pro Asn Leu Pro Pro Pro Pro
65                  70                  75                  80

Pro Ser Asn Ser Pro Ser Asp Ser Asp Ser Ile Gln Lys Pro Ser Trp
                85                  90                  95

Asp Phe Asp Tyr Asp Thr Lys Val Val Asp Leu Asp Pro Cys Leu Ser
            100                 105                 110

Lys Lys Pro Leu Glu Glu Lys Pro Ser Gln Pro Tyr Ser Ala Arg Glu
        115                 120                 125

Ser Leu Ser Glu Val Gln Ser Leu Ser Ser Phe Gln Ser Glu Ser Cys
130                 135                 140

Asp Asp Asn Glu Ser Leu Ala Ala Pro Asp Leu Ser Lys Pro Arg Gly
145                 150                 155                 160

Tyr His Trp Asp Thr Ser Asp Trp Met Pro Ser Val Pro Leu Pro Asp
                165                 170                 175

Ile Gln Glu Phe Pro Asn Tyr Glu Val Ile Asp Glu Gln Thr Pro Leu
            180                 185                 190

Tyr Ser Ala Asp Pro Asn Ala Ile Asp Thr Asp Tyr Tyr Pro Gly Gly
        195                 200                 205

Tyr Asp Ile Glu Ser Asp Phe Pro Pro Pro Glu Asp Phe Pro Ala
    210                 215                 220

Ala Asp Glu Leu Pro Pro Leu Pro Pro Glu Phe Ser Asn Gln Phe Glu
225                 230                 235                 240

Ser Ile His Pro Pro Arg Asp Met Pro Ala Ala Gly Ser Leu Gly Ser
                245                 250                 255

Ser Ser Arg Asn Arg Gln Arg Phe Leu Asn Gln Tyr Leu Pro Asn
            260                 265                 270

Phe Tyr Pro Leu Asp Met Ser Glu Pro Gln Thr Lys Gly Thr Gly Glu
        275                 280                 285

Asn Ser Thr Cys Arg Glu Pro His Ala Pro Tyr Pro Pro Gly Tyr Gln
```

```
            290                 295                 300
Arg His Phe Glu Ala Pro Ala Val Glu Ser Met Pro Met Ser Val Tyr
305                 310                 315                 320

Ala Ser Thr Ala Ser Cys Ser Asp Val Ser Ala Cys Cys Glu Val Glu
                325                 330                 335

Ser Glu Val Met Met Ser Asp Tyr Glu Ser Gly Asp Asp Gly His Phe
                340                 345                 350

Glu Glu Val Thr Ile Pro Pro Leu Asp Ser Gln Gln His Thr Glu Val
            355                 360                 365

<210> SEQ ID NO 4
<211> LENGTH: 285
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 4

Xaa Ser Thr Thr Glu Ala Leu Phe Ala Ser Val Glu Asp Tyr Ile Leu
1               5                   10                  15

Val Arg Gly Val Ser Leu Val His Thr Ala Lys Met Asn Pro Val Arg
            20                  25                  30

Met Ala Glu His Ala Leu Thr Val Trp Met Ala Pro Phe Val Ser Val
        35                  40                  45

Ile Arg Val Leu Gly Glu Lys Gly Val Arg Val Ile Ser Thr Ser Ala
    50                  55                  60

Leu Glu Thr Leu Ala Cys Thr Gly Pro Ser Val Arg Thr Arg Thr Ala
65                  70                  75                  80

Pro Ile Thr Ala Thr Ala Ala Thr Ser Thr Gly Asp Val Thr Ala Arg
                85                  90                  95

Met Leu Arg Pro Thr Thr Lys Val Val Asp Leu Asp Pro Cys Leu Ser
            100                 105                 110

Lys Lys Pro Leu Glu Glu Lys Pro Ser Gln Pro Tyr Ser Ala Arg Glu
        115                 120                 125

Ser Leu Ser Glu Val Gln Ser Leu Ser Ser Phe Gln Ser Glu Ser Cys
    130                 135                 140

Asp Asp Asn Gly Tyr His Trp Asp Thr Ser Asp Trp Met Pro Ser Val
145                 150                 155                 160

Pro Leu Pro Asp Ile Gln Glu Phe Pro Asn Tyr Glu Val Ile Asp Glu
                165                 170                 175

Gln Thr Pro Leu Tyr Ser Ala Asp Pro Asn Ala Ile Asp Thr Asp Tyr
            180                 185                 190

Tyr Pro Gly Gly Tyr Asp Ile Glu Ser Asp Phe Pro Pro Pro Pro Glu
        195                 200                 205

Asp Phe Pro Ala Ala Asp Glu Leu Pro Leu Pro Pro Glu Phe Ser
    210                 215                 220

Asn Gln Phe Glu Ser Ile His Pro Pro Arg Asp Met Pro Ala Ala Gly
225                 230                 235                 240

Ser Leu Gly Ser Ser Arg Asn Arg Gln Arg Phe Asn Leu Asn Gln
                245                 250                 255

Tyr Leu Pro Asn Phe Tyr Pro Leu Asp Met Ser Glu Pro Gln Thr Lys
            260                 265                 270

Gly Thr Gly Glu Asn Ser Thr Cys Arg Glu Pro His Ala
        275                 280                 285
```

<210> SEQ ID NO 5
<211> LENGTH: 119
<212> TYPE: PRT
<213> ORGANISM: Homo sapiens

<400> SEQUENCE: 5

```
Leu Ser Lys Lys Pro Leu Glu Glu Lys Pro Ser Gln Pro Tyr Ser Ala
1               5                   10                  15

Arg Glu Ser Leu Ser Glu Val Gln Ser Leu Ser Ser Phe Gln Ser Glu
            20                  25                  30

Ser Cys Asp Asp Asn Ala Ser Ile Val Thr Val Met His Leu Val Asn
        35                  40                  45

Ala Val Val Asp Thr Val Ser Thr Glu Glu Ser Leu Ala Ala Pro Asp
    50                  55                  60

Leu Ser Lys Pro Arg Gly Tyr His Trp Asp Thr Ser Asp Trp Met Pro
65                  70                  75                  80

Ser Val Pro Leu Pro Asp Ile Gln Glu Phe Pro Asn Tyr Glu Val Ile
                85                  90                  95

Asp Glu Gln Thr Pro Leu Tyr Ser Ala Asp Pro Asn Ala Ile Asp Thr
            100                 105                 110

Asp Tyr Tyr Pro Gly Gly Tyr
        115
```

<210> SEQ ID NO 6
<211> LENGTH: 14786
<212> TYPE: DNA
<213> ORGANISM: Homo sapiens

<400> SEQUENCE: 6

```
agcgtgaggc gccggcgccg agctgggcgg ccgggcgcgg ggagagggcg cgggagcggc      60
tcgtgcggca ggtaccatgc ggacgcgcga gcccggcgag ggccccggca ggccccggtcc    120 ctgctcgggg gcgcgctgag acggcgggtg agctccacga gagcgccgtc gccacttcgg    180
gccaactttg cgattcccga cagttaagca atggggagac atttggcttt gctcctgctt    240
ctgctccttc tcttccaaca ttttggagac agtgatggca gccaacgact tgaacagact    300
cctctgcagt ttacacacct cgagtacaac gtcaccgtgc aggagaactc tgcagctaag    360
acttatgtgg ggcatcctgt caagatgggt gtttacatta cacatccagc gtgggaagta    420
aggtacaaaa ttgtttccgg agacagtgaa aacctgttca agctgaaga gtacattctc    480 ggagactttt gctttctaag aataaggacc aaaggaggaa atacagctat tcttaataga    540
gaagtgaagg atcactacac attgatagtg aaagcacttg aaaaaaatac taatgtggag    600
gcgcgaacaa aggtcagggt gcaggtgctg atacaaatg acttgagacc gttattctca    660
cccacctcat acagcgtttc tttacctgaa acacagcta aaggaccag tatcgcaaga    720 gtcagcgcca cggatgcaga cataggaacc aacgggaat tttactacag ttttaaagat    780
cgaacagata tgtttgctat tcacccaacc agtggtgtga tagtgttaac tggtagactt    840
gattacctag agaccaagct ctatgagatg gaaatcctcg ctgcggaccg tggcatgaag    900
ttgtatggga gcagtggcat cagcagcatg gccaagctaa cggtgcacat cgaacaggcc    960
aatgaatgtg ctccggtgat aacagcagtg acattgtcac catcagaact ggacagggac   1020
ccagcatatg caattgtgac agtggatgac tgcgatcagg gtgccaatgg tgacatagca   1080
tctttaagca tcgtggcagg tgaccttctc cagcagttta aacagtgag gtccttttcca   1140
```

```
gggagtaagg agtataaagt caaagccatc ggtggcattg attgggacag tcatcctttc    1200
ggctacaatc tcacactaca ggctaaagat aaaggaactc cgccccagtt ctcttctgtt    1260
aaagtcattc acgtgacttc tccacagttc aaagccgggc cagtcaagtt tgaaaaggat    1320
gtttacagag cagaaataag tgaatttgct cctcccaaca cacctgtggt catggtaaag    1380
gccattcctg cttattccca tttgaggtat gttttttaaaa gtacacctgg aaaagctaaa    1440
ttcagtttaa attacaacac tggtctcatt tctattttag aaccagttaa aagacagcag    1500
gcagcccatt ttgaacttga agtaacaaca agtgacagaa aagcgtccac caaggtcttg    1560
gtgaaagtct taggtgcaaa tagcaatccc cctgaattta cccagacagc gtacaaagct    1620
gcttttgatg agaacgtgcc cattggtact actgtcatga gcctgagtgc cgtagaccct    1680
gatgagggtg agaacgggta cgtgacatac agtatcgcaa atttaaatca tgtgccgttt    1740
gcgattgacc atttcactgg tgccgtgagt acgtcagaaa acctggacta cgaactgatg    1800
cctcgggttt atactctgag gattcgtgca tcagactggg gcttgccgta ccgccgggaa    1860
gtcgaagtcc ttgctacaat tactctcaat aacttgaatg caacacacc tttgtttgag    1920 aaaataaatt gtgaagggac aattcccaga gatctaggcg tgggagagca ataaccact     1980 gtttctgcta ttgatgcaga tgaacttcag ttggtacagt atcagattga agctggaaat    2040
gaactggatt tctttagttt aaaccccaac tcggggtat tgtcattaaa gcgatcgcta     2100
atggatggct taggtgcaaa ggtgtctttc cacagtctga gaatcacagc tacagatgga    2160
gaaaattttg ccacaccatt atatatcaac ataacagtgg ctgccagtca caagctggta    2220
aacttgcagt gtgaagagac tggtgttgcc aaaatgctgg cagagaagct cctgcaggca    2280
aataaattac acaaccaggg agaggtggag gatattttct tcgattctca ctctgtcaat    2340
gctcacatac cgcagtttag aagcactctt ccgactggta ttcaggtaaa ggaaaaccag    2400
cctgtgggtt ccagtgtaat tttcatgaac tccactgacc ttgacactgg cttcaatgga    2460
aaactggtct atgctgtttc tggaggaaat gaggatagtt gcttcatgat tgatatggaa    2520
acaggaatgc tgaaaatttt atctcctctt gaccgtgaaa caacagacaa atacaccctg    2580
aatattaccg tctatgacct tgggataccc cagaaggctg cgtggcgtct tctacatgtc    2640
gtggttgtcg atgccaatga taatccaccc gagttttac aggagagcta ttttgtggaa     2700
gtgagtgaag acaaggaggt acatagtgaa atcatccagg ttgaagccac agataaagac    2760
ctggggccca acggacacgt gacgtactca attgttacag acacagacac attttcaatt    2820
gacagcgtga cgggtgttgt taacatcgca cgccctctgg atcgagagct gcagcatgag    2880
cactccttaa agattgaggc cagggaccaa gccagagaag agcctcagct gttctccact    2940
gtcgttgtga agtatcact agaagatgtt aatgacaacc cacctacatt tattccacct    3000
aattatcgtg tgaaagtccg agaggatctt ccagaaggaa ccgtcatcat gtggttagaa    3060
gcccacgatc ctgatttagg tcagtctggt caggtgagat acagccttct ggaccacgga    3120
gaaggaaact tcgatgtgga taaactcagt ggagcagtta ggatcgtcca gcagttggac    3180
tttgagaaga agcaagtgta atctcact gtgagggcca aagacaaggg aaagccagtt      3240
tctctgtctt ctacttgcta tgttgaagtt gaggtggttg atgtgaatga aacctgcac     3300 ccacccgtgt tttccagctt tgtggaaaag gggacagtga agaagatgc acctgttggt     3360 tcattggtaa tgacggtgtc ggctcatgat gaggacgcca aagagatgg ggagatccga    3420 tactccatta gagatggctc tggcgttggt gttttcaaaa taggtgaaga cacaggtgtc    3480
atagagacgt cagatcgact ggaccgtgaa tcgacctccc attattggct aacagtcttt    3540
```

```
gcaaccgatc agggtgtcgt gcctctttca tcgttcatag agatctacat agaggttgag    3600
gatgtcaatg acaatgcacc acagacatca gagcctgttt attacccaga aatcatggaa    3660
aattctccta aagatgtatc tgtggtccag atcgaggcat ttgatccaga ttcgagctct    3720
aatgacaagc tcatgtacaa aattacaagt ggaaatccac aaggattctt ttcaatacat    3780
cctaaaacag gtctcatcac aactacgtca aggaagctag accgagaaca gcaagatgaa    3840
cacatattag aggttactgt gacagacaat ggtagtcccc ccaaatcaac cattgcaaga    3900
gtcattgtga aaatccttga tgaaaatgac aacaaacctc agtttctgca aaagttctac    3960
aaaatcagac tccctgagcg ggaaaagcca gaccgagaaa gaaatgccag acgggagccg    4020
ctctatcacg tcatagccac cgacaaggat gagggcccca atgcagaaat ctcctacagc    4080
atcgaagacg ggaatgagca tggcaaattt ttcatcgaac cgaaaactgg agtggtttcg    4140
tccaagaggt tttcagcagc tggagaatat gatattcttt caattaaggc agttgacaat    4200
ggtcgccctc aaaagtcatc aaccaccaga ctccatattg aatggatctc caagcccaaa    4260
ccgtccctgg agcccatttc atttgaagaa tcattttttta cctttactgt gatggaaagt    4320
gaccccgttc tcacatgat tggagtaata tctgtggagc ctcctggcat acccctttgg    4380
tttgacatca ctggtggcaa ctacgacagt cacttcgatg tggacaaggg aactggaacc    4440
atcattgttg ccaaacctct tgatgcagaa cagaagtcaa actacaacct cacagtcgag    4500
gctacagatg gaaccaccac tatcctcact caggtattca tcaaagtaat agacacaaat    4560
gaccatcgtc ctcagttttc tacatcaaag tatgaagttg ttattcctga agatacagcg    4620
ccagaaacag aaattttgca aatcagtgct gtggatcagg atgagaaaaa caaactaatc    4680
tacactctgc agagcagtag agatccactg agtctcaaga aatttcgtct tgatcctgca    4740
accggctctc tctatacttc tgagaaactg gatcatgaag ctgttcacca gcacaccctc    4800
acggtcatgg tacgagatca agatgtgcct gtaaaacgca actttgcaag gattgtggtc    4860
aatgtcagcg acacgaatga ccacgccccg tggttcaccg cttcctccta caagggcgg    4920 gtttatgaat cggcagccgt tggctcagtt gtgttgcagg tgacggctct ggacaaggac    4980
aaagggaaaa atgctgaagt gctgtactcg atcgagtcag gaaatattgg aaattctttt    5040
atgattgatc ctgtcttggg ctctattaaa actgccaaag aattagatcg aagtaaccaa    5100
gcggagtatg atttaatggt aaaagctaca gataagggca gtccaccaat gagtgaaata    5160
acttctgtgc gtatctttgt cacaattgct gacaacgcct ctccgaagtt tacatcaaaa    5220
gaatattctg ttgaacttag tgaaactgtc agcattggga gtttcgttgg atggttaca    5280 gcccatagtc aatcatcagt ggtgtatgaa ataaaagatg gaaatacagg tgatgctttt    5340
gatattaatc cacattctgg aactatcatc actcagaaag ccctggactt tgaaactttg    5400
cccatttaca cattgataat acaaggaact aacatggctg gtttgtccac taatacaacg    5460
gttctagttc acttgcagga tgagaatgac aacgcgccag ttttatgca ggcagaatat    5520 acaggactca ttagtgaatc agcctcaatt aacagcgtgg tcctaacaga caggaatgtc    5580
ccactggtga ttcgagcagc tgatgctgat aaagactcaa atgctttgct tgtatatcac    5640
attgttgaac catctgtaca cacatatttt gctattgatt ctagcactgg tgctattcat    5700
acagtactaa gtctggacta tgaagaaaca agtatttttc actttaccgt ccaagtgcat    5760
gacatgggaa cccacgtttt atttgctgag tatgcagcga atgtaacagt acatgtaatt    5820
gacattaatg actgccccccc tgtgtttgcc aagccattat atgaagcatc tcttttgtta    5880
```

```
ccaacataca aaggagtaaa agtcatcaca gtaaatgcta cagatgctga ttcaagtgca    5940
ttctcacagt tgatttactc catcaccgaa ggcaacatcg gggagaagtt ttctatggac    6000
tacaagactg gtgctctcac tgtccaaaac acaactcagt taagaagccg ctacgagcta    6060
accgttagag cttccgatgg cagatttgcc ggccttacct ctgtcaaaat taatgtgaaa    6120
gaaagcaaag aaagtcacct aaagtttacc caggatgtct actctgcggt agtgaaagag    6180
aattccaccg aggccgaaac attagctgtc attactgcta ttgggaatcc aatcaatgag    6240
cctttgtttt atcacatcct caacccagat cgcagattta aaataagccg cacttcagga    6300
gttctgtcaa ccactggcac gcccttcgat cgtgagcagc aggaggcgtt tgatgtggtt    6360
gtagaagtga cagaggaaca taagccttct gcagtggccc acgttgtcgt gaaggtcatt    6420
gtagaagacc aaaatgataa tgcgccggtg tttgtcaacc ttccctacta cgccgttgtt    6480
aaagtggaca ctgaggtggg ccatgtcatt cgctatgtca ctgctgtaga cagagacagt    6540
ggcagaaacg gggaagtgca ttactacctc aaggaacatc atgaacactt tcaaattgga    6600
cccttgggtg aaatttcact gaaaaagcaa tttgagcttg acaccttaaa taagaatat     6660
cttgttacag tggttgcaaa agatggaggg aacccggcct tttcagcgga agttatcgtt    6720
ccgatcactg tcatgaataa agccatgcct gtgtttgaaa acctttctca cagtgcagag    6780
attgcagaga gcatccaggt gcacagccct gtggtccacg tgcaggctaa cagcccggaa    6840
ggcctgaaag tgttctacag catcacagac ggagacccctt tcagccagtt cactattaac    6900
ttcaatactg gagttatcaa tgtcatagct cctctggact ttgaggccca cccggcatat    6960
aagctgagca tacgcgcaac tgactccttg acgggcgctc atgctgaagt atttgtggac    7020
atcatagtag acgacatcaa tgataaccct cctgtgtttg ctcagcagtc ttatgcggtg    7080
accctgtctg aggcatctgt aattggaacg tctgttgttc aagttagagc caccgattct    7140
gattcagaac caaatagagg aatctcatac cagatgtttg ggaatcacag caagagtcat    7200
gatcattttc atgtagacag cagcactggc ctcatctcac tactcagaac cctggattac    7260
gagcagtccc ggcagcacac gattttttgtg agggcagttg atggtggtat gcccacgctg    7320
agcagtgatg tgattgtcac ggtggacgtt accgacctca atgataatcc accactcttt    7380
gaacaacaga tttatgaagc cagaattagc gagcacgccc ctcatgggca tttcgtgacc    7440
tgtgtaaaag cctatgatgc agacagttca gacatagaca agttgcagta ttccattctg    7500
tctggcaatg atcataaaca ttttgtcatt gacagtgcaa cagggattat caccctctca    7560
aacctgcacc ggcacgccct gaagccattt tacagtctta acctgtcagt gtctgatgga    7620
gtttttagaa gttccaccca ggttcatgta actgtaattg gaggcaattt gcacagtcct    7680
gctttccttc agaacgaata tgaagtggaa ctagctgaaa acgctcccct acataccctg    7740
gtgatggagg tgaaaactac ggatggggat tctggtattt atggtcacgt tacttaccat    7800
attgtaaatg actttgccaa agacagattt tacataaatg agagaggaca gatatttact    7860
ttggaaaaac ttgatcgaga aaccccggcg gagaaagtga tctcagtccg tttaatggct    7920
aaggatgctg gaggaaaagt tgctttctgc accgtgaatg tcatccttac agatgacaat    7980
gacaatgcac cacaatttcg agcaaccaaa tacgaagtga atatcgggtc cagtgctgct    8040
aaagggactt cagtcgttaa agttcttgca agtgatgccg atgagggctc caatgccgac    8100
atcacctatg ccattgaagc agactctgaa agtgtaaaag agaatttgga aattaacaaa    8160
ctgtccggcg taatcactac aaaggagagc ctcattggct tggaaaatga attcttcact    8220
ttctttgtta gagctgtgga taatgggtct ccatcaaaag aatctgttgt tcttgtctat    8280
```

```
gttaaaatcc ttccaccgga aatgcagctt ccaaaatttt cagaaccttt ctataccttt    8340
acagtgtcag aggacgtgcc tattggaaca gagatagatc tcatccgagc agaacatagt    8400
gggactgttc tttacagcct ggtcaaaggg aatactccag aaagcaatag ggatgagtcc    8460
tttgtgattg acagacagag cgggagactg aagttggaga agagtcttga tcatgagaca    8520
actaagtggt atcagttttc catactggcc aggtgcactc aagatgacca tgagatggtg    8580
gcttctgtag atgttagtat ccaagtgaaa gatgcaaatg acaacagccc ggtctttgaa    8640
tctagtccat atgaggcatt cattgttgaa aacctgccag ggggaagtag agtaattcag    8700
atcagggcat ctgatgctga ctcaggaacc aacggccaag ttatgtatag cctggatcag    8760
tcacaaagtg tggaagtcat tgaatccttt gccattaaca tggaaacagg ctggattaca    8820
actttaaagg aacttgacca tgaaaagaga gacaattacc agattaaagt ggttgcatca    8880
gatcatggtg aaaagatcca gctatcctcc acagccattg tggatgttac cgtcaccgat    8940
gtcaacgata gtccaccacg attcacggcc gagatctata aagggactgt gagtgaggat    9000
gaccccaag gtggggtgat tgccatctta agtaccacgg atgctgattc tgaagagatc    9060
aacagacaag ttacatattt cataacagga ggggatcctt taggacagtt tgccgttgaa    9120
actatacaga atgaatggaa ggtatatgtg aagaaacctc tagacaggga aaaaagggac    9180
aattaccttc ttactatcac ggcaactgat ggcaccttct catcaaaagc gatagttgaa    9240
gtgaaagttc tggatgcaaa tgacaacagt ccagtttgtg aaaagacttt atattcagac    9300
actattcctg aagacgtcct tcctggaaaa ttgatcatgc agatctctgc tacagacgca    9360
gacatccgct ctaacgctga aattacttac acgttattgg gttcaggtgc agaaaaattc    9420
aaactaaatc cagacacagg tgaactgaaa acgtcaaccc cccttgatcg tgaggagcaa    9480
gctgtttatc atcttctcgt cagggccaca gatggaggag gaagattctg ccaagccagt    9540
attgtgctca cgctagaaga tgtgaacgat aacgcccccg aattctctgc cgatccttat    9600
gccatcaccg tgtttgaaaa cacagagccg ggaacgctgc tgacaagagt gcaggccaca    9660
gatgccgacg caggattaaa tcggaagatt ttatactcac tgattgactc tgctgatggg    9720
cagttctcca ttaacgaatt atctggaatt attcagttag aaaaacccttt ggacagagaa    9780
ctccaggcag tatacaccct ctcttttgaaa gctgtggatc aaggcttgcc aaggaggctg    9840
actgccactg gcactgtgat tgtatcagtt cttgacataa atgacaaccc ccctgtgttt    9900
gagtaccgtg aatatggtgc caccgtgtct gaggacattc ttgttggaac tgaagttctt    9960
caagtgtatg cagcaagtcg ggatattgaa gcaaatgcag aaatcaccta ctcaataata   10020
agtggaaatg aacatgggaa attcagcata gattctaaaa caggggccgt atttatcatt   10080
gagaatctgg attatgagag ctctcatgag tattacctaa cagtagaggc cactgatgga   10140
ggcacgcctt cactgagcga cgttgccact gtgaacgtta atgtaacaga tatcaacgat   10200
aatacccctg tgttcagcca agacacctac acgacagtca tcagtgaaga tgccgttctt   10260
gagcagtctg tcatcacggt tatggccgat gatgccgatg accttccaa cagccacatc    10320
cactactcaa ttatagatgg caaccaagga agctcgttca caattgaccc cgtcagggga   10380
gaagtcaaag tgaccaaact tctcgaccga gaaacgattt caggttacac gctcacggtt   10440
caagcttctg ataatggcag tccacccaga gtcaacacga cgaccgtgaa catcgatgtg   10500
tccgatgtca atgacaacgc gcccgtcttc tccaggggaa actacagtgt cattatccag   10560
gaaaataagc cagtgggctt cagcgtgctg cagctggtag taacagatga ggattcttcc   10620
```

```
cataacggtc caccettctt ctttactatt gtaactggaa atgatgagaa ggcttttgaa    10680
gttaacccgc aaggagtcct cctgacatca tctgccatca agaggaagga gaaagatcat    10740
tacttactgc aggtgaaggt ggcagataat ggaaagcctc agttgtcatc tttgacatac    10800
attgacatta gggtaattga ggagagcatc tatccgcctg cgattttgcc cctggagatt    10860
ttcatcacct cttctggaga agaatactca ggtggcgtca ttgggaagat ccatgccaca    10920
gaccaggacg tgtatgatac tctaacctac agtctcgacc ctcagatgga caacctgttc    10980 tctgttttcca gcacaggggg caagctgata gcacacaaaa agctagacat agggcaatac    11040
cttctcaatg tcagcgtaac agatgggaag ttcacgacgg tggccgacat cacagtgcat    11100
atcagacaag tcacacagga gatgttgaac cacaccatcg cgatccgctt tgccaacctc    11160
actccggaag aattcgttgg tgactactgg cgcaacttcc agcgagcttt acggaacatc    11220
ctgggtgtga ggaggaacga catacagatt gttagtttgc agtcctctga acctcaccca    11280
catctggacg tcttactttt tgtagagaaa ccaggtagtg ctcagatctc aacaaaacaa    11340
cttctgcaca agattaactc ttccgtgact gacattgagg aaatcattgg agttaggata    11400
ctgaatgtat tccagaaact ctgcgcggga ctggactgcc cctggaagtt ctgcgatgaa    11460
aaggtgtctg tggatgaaag tgtgatgtca acacacagca cagccagact gagttttgtg    11520
actccccgcc accacagggc agcggtgtgt ctctgcaaag agggaaggtg cccacctgtc    11580
caccatggct gtgaagatga tccgtgccct gagggatccg aatgtgtgtc tgatccctgg    11640
gaggagaaac acacctgtgt ctgtcccagc ggcaggtttg gtcagtgccc agggagttca    11700
tctatgacac tgactggaaa cagctacgtg aaataccgtc tgacggaaaa tgaaaacaaa    11760
ttagagatga aactgaccat gaggctcaga acatattcca cgcatgcggt tgtcatgtat    11820
gctcgaggaa ctgactatag catcttggag attcatcatg gaaggctgca gtacaagttt    11880
gactgtggaa gtggccctgg aattgtctct gttcagagca ttcaggtcaa tgatgggcag    11940
tggcacgcag tggccctgga agtgaatgga aactatgctc gcttggttct agaccaagtt    12000
catactgcat cgggcacagc cccagggact ctgaaaaccc tgaacctgga taactatgtg    12060
ttttttggtg gccacatccg tcagcaggga acaaggcatg gaagaagtcc tcaagttggt    12120
aatggtttca ggggttgtat ggactccatt tatttgaatg ggcaggagct cccttttaaac   12180 agcaaaccca gaagctatgc acacatcgaa gagtcggtgg atgtatctcc aggctgcttc    12240
ctgacggcca cggaagactg cgccagcaac ccttgccaga atggaggcgt ttgcaatccg    12300
tcacctgctg gaggttatta ctgcaaatgc agtgccttgt acataggac ccactgtgag    12360 ataagcgtca atccgtgttc ctccaagcca tgcctctatg ggggcacgtg tgttgtcgac    12420
aacggaggct ttgtttgcca gtgtagagga ttatatactg gtcagaggtg tcagcttagt    12480
ccatactgca aagatgaacc ctgtaagaat ggcggaacat gctttgacag tttggatggc    12540
gccgtttgtc agtgtgattc gggttttagg ggagaaaggt gtcagagtga tatcgacgag    12600
tgctctggaa accettgcct gcacgggccc tctgtgagaa cacgcacgg ctcctatcac    12660 tgcaactgca gccacgagta caggggacgt cactgcgagg atgctgcgcc caaccagtat    12720
gtgtccacgc cgtggaacat tgggttggcg gaaggaattg gaatcgttgt gtttgttgca    12780
gggatatttt tactggtggt ggtgtttgtt ctctgccgta agatgattag tcggaaaaag    12840
aagcatcagg ctgaacctaa agacaagcac ctgggacccg ctacggcttt cttgcaaaga    12900 ccgtatttttg attccaagct aaataagaac atttactcag acataccacc ccaggtgcct    12960
gtccggccta tttcctacac cccgagtatt ccaagtgact caagaaacaa tctggaccga    13020
```

-continued

```
aattccttcg aaggatctgc tatcccagag catcccgaat tcagcacttt taaccccgag   13080
tctgtgcacg ggcaccgaaa agcagtggcg gtctgcagcg tggcgccaaa cctgcctccc   13140
ccaccccctt caaactcccc ttctgacagc gactccatcc agaagcctag ctgggacttt   13200
gactatgaca caaaagtggt ggatcttgat ccctgtcttt ccaagaagcc tctagaggaa   13260
aagccttccc agccatacag tgcccgggaa agcctgtctg aagtgcagtc tctgagctcc   13320
ttccagtccg aatcgtgcga tgacaatggg tatcactggg atacatcaga ttggatgcca   13380
agcgttcctc tgccggacat acaagagttc cccaactatg aggtgattga tgagcagaca   13440
cccctgtact cagcagatcc aaacgccatc gatacggact attaccctgg aggctacgac   13500
atcgaaagtg attttcctcc accccagaa gacttccccg cagctgatga gctaccaccg   13560
ttaccgcccg aattcagcaa tcagtttgaa tccatccacc ctcctagaga catgcctgcc   13620
gcgggtagct tgggttcttc atcaagaaac cggcagaggt tcaacttgaa tcagtatttg   13680
cccaattttt atcccctcga tatgtctgaa cctcaaacaa aaggcactgg tgagaatagt   13740
acttgtagag aaccccatgc cccttacccg ccagggtatc aaagacactt cgaggcgccc   13800
gctgtcgaga gcatgccat gtctgtgtac gcctccaccg cctcctgctc tgacgtgtca   13860
gcctgctgcg aagtggagtc cgaggtcatg atgagtgact atgagagcgg ggacgacggc   13920
cacttcgaag aggtgacgat cccgcccctg gattcccagc agcacacgga agtctgactc   13980
tcaactcccc ccaaagtgcc tgactttagt gaacctagag gtgatgtgag taatccgcgc   14040
tgttctttgc agcagtgctt ccaagctttt tttggtgagc cgaatgggca tggctgcgct   14100
ggatcctgcg cctctggacg tgctagccat ttccagtgtc ccaactactg tcatcgtgag   14160
gttttcatcg gctgtgccat ttcccaacgt cttttgggat ttacatctgt ctgtgttaaa   14220
ataatcaaac gaaaaatcag tcctgtgttg tcagcatgat tcatgtattt atatagattt   14280
gattatttta atttcctgt ctcttttttt tgtaaatttt atgtacagat ttgattttttc   14340 atagttttaa ctagatttcc aagatatttt gtgcatttgt ttcaactgaa ttttggtggt   14400
gtcagtgcca ttatctagca ccctgatttt tttttttta ctataaccag ggtttcattc   14460
tgtctttttc cactgaagtg tgacattttg ttagtacatt tcagtgtagt cattcatttc   14520
tagctgtaca taggatgaag gagagatcag atacatgaac atgtcttaca tgggttgctg   14580
tatttagaat tataaacatt tttcattatt ggaaagtgta acgggaacct tctgcatacc   14640
tgtttagaac caaaaccacc atgacacagt ttttatagtg tctgtatatt tgtgatgcaa   14700
tggtcttgta aaggttttta atgaaaacta ccattagcca gtctttctta ctgacaataa   14760
attattaata aaatacttga gcttta                                         14786
```

<210> SEQ ID NO 7
<211> LENGTH: 1852
<212> TYPE: DNA
<213> ORGANISM: Homo sapiens

<400> SEQUENCE: 7

```
aaggggggagg gagtggggaa agaggcagcg agtcgccgca gccggcggcc gcaactcctc     60
aactcggcgg ctggctgcct gggcacgtcc tgacaaactt ggctgctccc gggccctcgt    120
tccggccccg cgcactctct tttcgcctgc gtttggtgct taagtttgcc ctggtcggaa    180
gcctccggag atgcggccgc ctgggtcccg gcggcacgga cgttggcact ctggttaggg    240
acatgctgaa gatcccgggg aggcaaagtt ggtacttcaa acccggctct taacacatat    300
```

```
ctacaccgcg agggatcac ggagctgccg aggactttag agcccagggc cgaggactcg    360
gctagactga ttcccgacag ttaagcaatg gggagacatt tggctttgct cctgcttctg    420
ctccttctct tccaacattt tggagacagt gatggcagcc aacgacttga acagactcct    480
ctgcagttta cacacctcga gtacaacgtc accgtgcagg agaactctgc agctaagact    540
tatgtggggc atcctgtcaa gatgggtgtt tacattacac atccagcgtg ggaagtaagg    600
tacaaaattg tttccggaga cagtgaaaac ctgttcaaag ctgaagagta cattctcgga    660
gacttttgct ttctaagaat aaggaccaaa ggaggaaata cagctattct aatagagaa     720
gtgaaggatc actacacatt gatagtgaaa gcacttgaaa aaaatactaa tgtggaggcg    780
cgaacaaagg tcagggtgca ggtgctggat acaaatgact tgagaccgtt attctcaccc    840
acctcataca gcgtttcttt acctgaaaac acagctataa ggaccagtat cgcaagagtc    900
agcgccacgg atgcagacat aggaaccaac ggggaatttt actacagttt taaagatcga    960
acagatatgt ttgctattca cccaaccagt ggtgtgatag tgttaactgg tagacttgat   1020
tacctagaga ccaagctcta tgagatggaa atcctgctg cggaccgtgg catgaagttg    1080
tatgggagca gtggcatcag cagcatggcc aagctaacgg tgcacatcga acaggccaat   1140
gaatgtgctc cggtgataac agcagtgaca ttgtcaccat cagaactgga cagggaccca   1200
gcatatgcaa ttgtgacagt ggatgactgc gatcagggtg ccaatggtga catagcatct   1260
ttaagcatcg tggcaggtga ccttctccag cagtttagaa cagtgaggtc ctttccaggg   1320
agtaaggagt ataaagtcaa agccatcggt ggcattgatt gggacagtca tcctttcggc   1380
tacaatctca cactacaggc taaagataaa ggaactccgc cccagttctc ttctgttaaa   1440
gtcattcacg tgacttctcc acagttcaaa gccgggccag tcaagtttga aaaggatgtt   1500
tacagagcag aaataagtga atttgctcct cccaacacac ctgtggtcat ggtaaaggcc   1560
attcctgctt attcccattt gaggtatgtt tttaaaagta cacctggaaa agctaaattc   1620
agtttaaatt acaacactgg tctcatttct attttagaac cagttaaaag acagcaggca   1680
gcccattttg aacttgaagt aacaacaagt gacagaaaag cgtccaccaa ggtcttggtg   1740
aaagtcttag gtgcaaatag caatcccct gaatttaccc agacagcgta caaagctgct   1800
tttgatgaga acgtgcccat tggtactact gtcatgagcc tgagtgccgt ag           1852

<210> SEQ ID NO 8
<211> LENGTH: 1305
<212> TYPE: DNA
<213> ORGANISM: Homo sapiens

<400> SEQUENCE: 8
tgattccaag ctaaataaga acatttactc agacatacca ccccaggtgc ctgtccggcc     60
tatttcctac accccgagta ttccaagtga ctcaagaaac aatctggacc gaaattcctt    120
cgaaggatct gctatcccag agcatcccga attcagcact tttaacccg agtctgtgca    180
cgggcaccga aaagcagtgg cggtctgcag cgtggcgcca aacctgcctc ccccaccccc    240
ttcaaactcc ccttctgaca gcgactccat ccagaagcct agctgggact ttgactatga    300
cacaaaagtg gtggatcttg atccctgtct ttccaagaag cctctagagg aaaagccttc    360
ccagccatac agtgcccggg aaagcctgtc tgaagtgcag tctctgagct ccttccagtc    420
cgaatcgtgc gatgacaatg aatctttggc tgctcctgac ctcagcaaac caagagggta    480
tcactgggat acatcagatt ggatgccaag cgttcctctg ccggacatac aagagttccc    540
caactatgag gtgattgatg agcagacacc cctgtactca gcagatccaa acgccatcga    600
```

| tacggactat | taccctggag | gctacgacat | cgaaagtgat | tttcctccac | ccccagaaga | 660 |
| cttccccgca | gctgatgagc | taccaccgtt | accgcccgaa | ttcagcaatc | agtttgaatc | 720 |
| catccaccct | cctagagaca | tgcctgccgc | gggtagcttg | ggttcttcat | caagaaaccg | 780 |
| gcagaggttc | aacttgaatc | agtatttgcc | caattttat | cccctcgata | tgtctgaacc | 840 |
| tcaaacaaaa | ggcactggtg | agaatagtac | ttgtagagaa | ccccatgccc | cttacccgcc | 900 |
| agggtatcaa | agacacttcg | aggcgcccgc | tgtcgagagc | atgcccatgt | ctgtgtacgc | 960 |
| ctccaccgcc | tcctgctctg | acgtgtcagc | ctgctgcgaa | gtggagtccg | aggtcatgat | 1020 |
| gagtgactat | gagagcgggg | acgacggcca | cttcgaagag | gtgacgatcc | cgcccctgga | 1080 |
| ttcccagcag | cacacggaag | tctgactctc | aactccccc | aaagtgcctg | actttagtga | 1140 |
| acctagaggt | gatgtgagta | atccgcgctg | ttctttgcag | cagtgcttcc | aagcttttt | 1200 |
| tggtgagccg | aatgggcatg | gctgcgctgg | atcctgcgcc | tctggacgtg | ctagccattt | 1260 |
| ccagtgtccc | aactactgtc | atcgtgaggt | tttcatcggc | tgtgc | | 1305 |

<210> SEQ ID NO 9
<211> LENGTH: 854
<212> TYPE: DNA
<213> ORGANISM: Homo sapiens

<400> SEQUENCE: 9

| gtcgacaacg | gaggctttgt | tgccagtgt | agaggattat | atactggtca | gaggtgtcag | 60 |
| cttagtccat | actgcaaaga | tgaaccctgt | aagaatggcg | aacatgctt | tgacagtttg | 120 |
| gatggcgccg | tttgtcagtg | tgattcgggt | tttaggggag | aaaggtgtca | gagtgatatc | 180 |
| gacgagtgct | ctggaaaccc | ttgcctgcac | ggggccctct | gtgagaacac | gcacggctcc | 240 |
| tatcactgca | actgcagcca | cgagtacagg | ggacgtcact | gcgaggatgc | tgcgcccaac | 300 |
| cacaaaagtg | gtggatcttg | atccctgtct | ttccaagaag | cctctagagg | aaaagccttc | 360 |
| ccagccatac | agtgcccggg | aaagcctgtc | tgaagtgcag | tctctgagct | ccttccagtc | 420 |
| cgaatcgtgc | gatgacaatg | gtatcactg | ggatacatca | gattggatgc | caagcgttcc | 480 |
| tctgccggac | atacaagagt | tccccaacta | tgaggtgatt | gatgagcaga | caccctgta | 540 |
| ctcagcagat | ccaaacgcca | tcgatacgga | ctattaccct | ggaggctacg | acatcgaaag | 600 |
| tgattttcct | ccaccccag | aagacttccc | cgcagctgat | gagctaccac | cgttaccgcc | 660 |
| cgaattcagc | aatcagtttg | aatccatcca | ccctcctaga | gacatgcctg | ccgcgggtag | 720 |
| cttgggttct | tcatcaagaa | accggcagag | gttcaacttg | aatcagtatt | tgcccaattt | 780 |
| ttatcccctc | gatatgtctg | aacctcaaac | aaaaggcact | ggtgagaata | gtacttgtag | 840 |
| agaaccccat | gccc | | | | | 854 |

<210> SEQ ID NO 10
<211> LENGTH: 357
<212> TYPE: DNA
<213> ORGANISM: Homo sapiens

<400> SEQUENCE: 10

| ctttccaaga | agcctctaga | ggaaaagcct | tcccagccat | acagtgcccg | ggaaagcctg | 60 |
| tctgaagtgc | agtctctgag | ctccttccag | tccgaatcgt | gcgatgacaa | tgcttccata | 120 |
| gtgaccgtaa | tgcaccttgt | caatgctgtg | gttgacacgg | tgagcacaga | gaatctttg | 180 |
| gctgctcctg | acctcagcaa | accaagaggg | tatcactggg | atacatcaga | ttggatgcca | 240 |

```
agcgttcctc tgccggacat acaagagttc cccaactatg aggtgattga tgagcagaca    300
cccctgtact cagcagatcc aaacgccatc gatacggact attaccctgg aggctac      357
```

<210> SEQ ID NO 11
<211> LENGTH: 30
<212> TYPE: DNA
<213> ORGANISM: Homo sapiens

<400> SEQUENCE: 11

```
ggctacacat tcaccaggtc ctggatgcac                                      30
```

<210> SEQ ID NO 12
<211> LENGTH: 24
<212> TYPE: DNA
<213> ORGANISM: Homo sapiens

<400> SEQUENCE: 12

```
atttatcctg gtagtggtgg tact                                            24
```

<210> SEQ ID NO 13
<211> LENGTH: 30
<212> TYPE: DNA
<213> ORGANISM: Homo sapiens

<400> SEQUENCE: 13

```
acaagatcag ggggtcagag gttcgactac                                      30
```

<210> SEQ ID NO 14
<211> LENGTH: 30
<212> TYPE: DNA
<213> ORGANISM: Homo sapiens

<400> SEQUENCE: 14

```
agtgccagct caagtgtaag ttccatgcac                                      30
```

<210> SEQ ID NO 15
<211> LENGTH: 21
<212> TYPE: DNA
<213> ORGANISM: Homo sapiens

<400> SEQUENCE: 15

```
gacacatcca aactggcttc t                                               21
```

<210> SEQ ID NO 16
<211> LENGTH: 27
<212> TYPE: DNA
<213> ORGANISM: Homo sapiens

<400> SEQUENCE: 16

```
tttcagggga gtgggtatcc attcacg                                         27
```

<210> SEQ ID NO 17
<211> LENGTH: 8
<212> TYPE: PRT
<213> ORGANISM: Homo sapiens

<400> SEQUENCE: 17

Gly Tyr Thr Phe Thr Arg Ser Trp
1               5

<210> SEQ ID NO 18
<211> LENGTH: 8
<212> TYPE: PRT

<210> SEQ ID NO 18
<211> LENGTH: 7
<212> TYPE: PRT
<213> ORGANISM: Homo sapiens

<400> SEQUENCE: 18

Ile Tyr Pro Gly Ser Gly Gly Thr
1               5

<210> SEQ ID NO 19
<211> LENGTH: 10
<212> TYPE: PRT
<213> ORGANISM: Homo sapiens

<400> SEQUENCE: 19

Thr Arg Ser Gly Gly Gln Arg Phe Asp Tyr
1               5                   10

<210> SEQ ID NO 20
<211> LENGTH: 10
<212> TYPE: PRT
<213> ORGANISM: Homo sapiens

<400> SEQUENCE: 20

Ser Ala Ser Ser Ser Val Ser Ser Met His
1               5                   10

<210> SEQ ID NO 21
<211> LENGTH: 7
<212> TYPE: PRT
<213> ORGANISM: Homo sapiens

<400> SEQUENCE: 21

Asp Thr Ser Lys Leu Ala Ser
1               5

<210> SEQ ID NO 22
<211> LENGTH: 9
<212> TYPE: PRT
<213> ORGANISM: Homo sapiens

<400> SEQUENCE: 22

Phe Gln Gly Ser Gly Tyr Pro Phe Thr
1               5

<210> SEQ ID NO 23
<211> LENGTH: 372
<212> TYPE: DNA
<213> ORGANISM: Homo sapiens

<400> SEQUENCE: 23

```
gttcagctgc agcagtctgg gtctgagctg gtgaggcctg gagcttcagt gaagctgtcc      60
tgcaaggctt ctggctacac attcaccagg tcctggatgc actggataaa gcagaggcct     120
ggacaaggcc ttgaatggat tggaaatatt tatcctggta gtggtggtac taactacgat     180
gagaagttca agagcaaggc cacactgact gtagacacgt cctccagcac agcctacatg     240
cagctcagca gcctgacatc tgaggactct gcgatctatt actgtacaag atcagggggt     300
cagaggttcg actactgggg ccaaggcacc actctcacag tctcctcagc caaaacgaca     360
cccccatctg tc                                                         372
```

<210> SEQ ID NO 24
<211> LENGTH: 338
<212> TYPE: DNA
<213> ORGANISM: Homo sapiens

<400> SEQUENCE: 24

```
attgtgatga cccagtctcc agcaatcatg tctgcatttt caggggaaaa ggtcaccatg        60
acctgcagtg ccagctcaag tgtaagttcc atgcactggt accagcagaa gtcaagcacc       120
tcccccaaat tctggattta tgacacatcc aaactggctt ctggagtccc aggtcgcttc       180
agtggcagtg ggtctgggaa ctcttactct ctcacgatca gcagcatgga ggctgaagat       240
gttgccactt attactgttt tcaggggagt gggtatccat tcacgttcgg agggggggacc      300
aagctggaaa taaaacgggc tgatgctgca ccaattgt                               338
```

<210> SEQ ID NO 25
<211> LENGTH: 124
<212> TYPE: PRT
<213> ORGANISM: Homo sapiens

<400> SEQUENCE: 25

```
Val Gln Leu Gln Gln Ser Gly Ser Glu Leu Val Arg Pro Gly Ala Ser
1               5                   10                  15

Val Lys Leu Ser Cys Lys Ala Ser Gly Tyr Thr Phe Thr Arg Ser Trp
            20                  25                  30

Met His Trp Ile Lys Gln Arg Pro Gly Gln Gly Leu Glu Trp Ile Gly
        35                  40                  45

Asn Ile Tyr Pro Gly Ser Gly Gly Thr Asn Tyr Asp Glu Lys Phe Lys
    50                  55                  60

Ser Lys Ala Thr Leu Thr Val Asp Thr Ser Ser Ser Thr Ala Tyr Met
65                  70                  75                  80

Gln Leu Ser Ser Leu Thr Ser Glu Asp Ser Ala Ile Tyr Tyr Cys Thr
                85                  90                  95

Arg Ser Gly Gly Gln Arg Phe Asp Tyr Trp Gly Gln Gly Thr Thr Leu
            100                 105                 110

Thr Val Ser Ser Ala Lys Thr Thr Pro Pro Ser Val
        115                 120
```

<210> SEQ ID NO 26
<211> LENGTH: 112
<212> TYPE: PRT
<213> ORGANISM: Homo sapiens

<400> SEQUENCE: 26

```
Ile Val Met Thr Gln Ser Pro Ala Ile Met Ser Ala Phe Ser Gly Glu
1               5                   10                  15

Lys Val Thr Met Thr Cys Ser Ala Ser Ser Ser Val Ser Ser Met His
            20                  25                  30

Trp Tyr Gln Gln Lys Ser Ser Thr Ser Pro Lys Phe Trp Ile Tyr Asp
        35                  40                  45

Thr Ser Lys Leu Ala Ser Gly Val Pro Gly Arg Phe Ser Gly Ser Gly
    50                  55                  60

Ser Gly Asn Ser Tyr Ser Leu Thr Ile Ser Ser Met Glu Ala Glu Asp
65                  70                  75                  80

Val Ala Thr Tyr Tyr Cys Phe Gln Gly Ser Gly Tyr Pro Phe Thr Phe
                85                  90                  95

Gly Gly Gly Thr Lys Leu Glu Ile Lys Arg Ala Asp Ala Ala Pro Ile
            100                 105                 110
```

<210> SEQ ID NO 27
<211> LENGTH: 630
<212> TYPE: PRT

<213> ORGANISM: Homo sapiens

<400> SEQUENCE: 27

```
Gly Ile Gln Val Lys Glu Asn Gln Pro Val Gly Ser Ser Val Ile Phe
1               5                   10                  15

Met Asn Ser Thr Asp Leu Asp Thr Gly Phe Asn Gly Lys Leu Val Tyr
            20                  25                  30

Ala Val Ser Gly Gly Asn Glu Asp Ser Cys Phe Met Ile Asp Met Glu
        35                  40                  45

Thr Gly Met Leu Lys Ile Leu Ser Pro Leu Asp Arg Glu Thr Thr Asp
    50                  55                  60

Lys Tyr Thr Leu Asn Ile Thr Val Tyr Asp Leu Gly Ile Pro Gln Lys
65                  70                  75                  80

Ala Ala Trp Arg Leu Leu His Val Val Val Asp Ala Asn Asp Asn
                85                  90                  95

Pro Pro Glu Phe Leu Gln Ser Tyr Phe Val Glu Val Ser Glu Asp
            100                 105                 110

Lys Glu Val His Ser Glu Ile Ile Gln Val Glu Ala Thr Asp Lys Asp
                115                 120                 125

Leu Gly Pro Asn Gly His Val Thr Tyr Ser Ile Val Thr Asp Thr Asp
    130                 135                 140

Thr Phe Ser Ile Asp Ser Val Thr Gly Val Val Asn Ile Ala Arg Pro
145                 150                 155                 160

Leu Asp Arg Glu Leu Gln His Glu His Ser Leu Lys Ile Glu Ala Arg
                165                 170                 175

Asp Gln Ala Arg Glu Glu Pro Gln Leu Phe Ser Thr Val Val Lys
            180                 185                 190

Val Ser Leu Glu Asp Val Asn Asp Asn Pro Pro Thr Phe Ile Pro Pro
        195                 200                 205

Asn Tyr Arg Val Lys Val Arg Glu Asp Leu Pro Glu Gly Thr Val Ile
    210                 215                 220

Met Trp Leu Glu Ala His Asp Pro Asp Leu Gly Gln Ser Gly Gln Val
225                 230                 235                 240

Arg Tyr Ser Leu Leu Asp His Gly Glu Gly Asn Phe Asp Val Asp Lys
                245                 250                 255

Leu Ser Gly Ala Val Arg Ile Val Gln Gln Leu Asp Phe Glu Lys Lys
            260                 265                 270

Gln Val Tyr Asn Leu Thr Val Arg Ala Lys Asp Lys Gly Lys Pro Val
        275                 280                 285

Ser Leu Ser Ser Thr Cys Tyr Val Glu Val Glu Val Val Asp Val Asn
    290                 295                 300

Glu Asn Leu His Pro Val Phe Ser Ser Phe Val Glu Lys Gly Thr
305                 310                 315                 320

Val Lys Glu Asp Ala Pro Val Gly Ser Leu Val Met Thr Val Ser Ala
                325                 330                 335

His Asp Glu Asp Ala Arg Arg Asp Gly Glu Ile Arg Tyr Ser Ile Arg
            340                 345                 350

Asp Gly Ser Gly Val Gly Val Phe Lys Ile Gly Glu Glu Thr Gly Val
        355                 360                 365

Ile Glu Thr Ser Asp Arg Leu Asp Arg Glu Ser Thr Ser His Tyr Trp
    370                 375                 380

Leu Thr Val Phe Ala Thr Asp Gln Gly Val Val Pro Leu Ser Ser Phe
385                 390                 395                 400
```

```
Ile Glu Ile Tyr Ile Glu Val Glu Asp Val Asn Asp Asn Ala Pro Gln
                405                 410                 415

Thr Ser Glu Pro Val Tyr Tyr Pro Gly Ile Met Glu Asn Ser Pro Lys
        420                 425                 430

Asp Val Ser Val Val Gln Ile Glu Ala Phe Asp Pro Asp Ser Ser Ser
            435                 440                 445

Asn Asp Lys Leu Met Tyr Lys Ile Thr Ser Gly Asn Pro Gln Gly Phe
    450                 455                 460

Phe Ser Ile His Pro Lys Thr Gly Leu Ile Thr Thr Thr Ser Arg Lys
465                 470                 475                 480

Leu Asp Arg Glu Gln Gln Asp Glu His Ile Leu Glu Val Thr Val Thr
                485                 490                 495

Asp Asn Gly Ser Pro Pro Lys Ser Thr Ile Ala Arg Val Ile Val Lys
            500                 505                 510

Ile Leu Asp Glu Asn Asp Asn Lys Pro Gln Phe Leu Gln Lys Phe Tyr
                515                 520                 525

Lys Ile Arg Leu Pro Glu Arg Glu Lys Pro Asp Arg Glu Arg Asn Ala
            530                 535                 540

Arg Arg Glu Pro Leu Tyr His Val Ile Ala Thr Asp Lys Asp Glu Gly
545                 550                 555                 560

Pro Asn Ala Glu Ile Ser Tyr Ser Ile Glu Asp Gly Asn Glu His Gly
                565                 570                 575

Lys Phe Phe Ile Glu Pro Lys Thr Gly Val Val Ser Ser Lys Arg Phe
            580                 585                 590

Ser Ala Ala Gly Glu Tyr Asp Ile Leu Ser Ile Lys Ala Val Asp Asn
        595                 600                 605

Gly Arg Pro Gln Lys Ser Ser Thr Thr Arg Leu His Ile Glu Trp Ile
    610                 615                 620

Ser Lys Pro Lys Pro Ser
625                 630

<210> SEQ ID NO 28
<211> LENGTH: 98
<212> TYPE: PRT
<213> ORGANISM: Homo sapiens

<400> SEQUENCE: 28

Ser Tyr Phe Val Glu Val Ser Glu Asp Lys Glu Val His Ser Glu Ile
1               5                   10                  15

Ile Gln Val Glu Ala Thr Asp Lys Asp Leu Gly Pro Asn Gly His Val
            20                  25                  30

Thr Tyr Ser Ile Val Thr Asp Thr Asp Thr Phe Ser Ile Asp Ser Val
        35                  40                  45

Thr Gly Val Val Asn Ile Ala Arg Pro Leu Asp Arg Glu Leu Gln His
    50                  55                  60

Glu His Ser Leu Lys Ile Glu Ala Arg Asp Gln Ala Arg Glu Glu Pro
65                  70                  75                  80

Gln Leu Phe Ser Thr Val Val Lys Val Ser Leu Glu Asp Val Asn
                85                  90                  95

Asp Asn

<210> SEQ ID NO 29
<211> LENGTH: 95
<212> TYPE: PRT
<213> ORGANISM: Homo sapiens
```

-continued

<400> SEQUENCE: 29

Tyr Lys Ile Arg Leu Pro Glu Arg Glu Lys Pro Asp Arg Glu Arg Asn
1               5                   10                  15

Ala Arg Arg Glu Pro Leu Tyr His Val Ile Ala Thr Asp Lys Asp Glu
            20                  25                  30

Gly Pro Asn Ala Glu Ile Ser Tyr Ser Ile Glu Asp Gly Asn Glu His
        35                  40                  45

Gly Lys Phe Phe Ile Glu Pro Lys Thr Gly Val Val Ser Ser Lys Arg
50                  55                  60

Phe Ser Ala Ala Gly Glu Tyr Asp Ile Leu Ser Ile Lys Ala Val Asp
65                  70                  75                  80

Asn Gly Arg Pro Gln Lys Ser Ser Thr Thr Arg Leu His Ile Glu
                85                  90                  95

<210> SEQ ID NO 30
<211> LENGTH: 25
<212> TYPE: PRT
<213> ORGANISM: Homo sapiens

<400> SEQUENCE: 30

Arg Glu Pro Leu Tyr His Val Ile Ala Thr Asp Lys Asp Glu Gly Pro
1               5                   10                  15

Asn Ala Glu Ile Ser Tyr Ser Ile Glu
            20                  25

<210> SEQ ID NO 31
<211> LENGTH: 25
<212> TYPE: PRT
<213> ORGANISM: Homo sapiens

<400> SEQUENCE: 31

Tyr His Val Ile Ala Thr Asp Lys Asp Glu Gly Pro Asn Ala Glu Ile
1               5                   10                  15

Ser Tyr Ser Ile Glu Asp Gly Asn Glu
            20                  25

<210> SEQ ID NO 32
<211> LENGTH: 25
<212> TYPE: PRT
<213> ORGANISM: Homo sapiens

<400> SEQUENCE: 32

Ile Gln Val Glu Ala Thr Asp Lys Asp Leu Gly Pro Asn Gly His Val
1               5                   10                  15

Thr Tyr Ser Ile Val Thr Asp Thr Asp
            20                  25

<210> SEQ ID NO 33
<211> LENGTH: 336
<212> TYPE: DNA
<213> ORGANISM: Unknown
<220> FEATURE:
<223> OTHER INFORMATION: hybridoma

<400> SEQUENCE: 33
cagtcagggt ctgggctggt gaggcctgga acttcagtga agctgtcctg caaggcttct     60
ggtttcacat tcaccagcaa ctggatgcac tgggtgaaac agaggcctgg acaaggcctt    120
gattggatcg gaaatattta tcctggtagt ggtaaaacta attacggtga agagttcaag    180
agcaaggcca cactgactgt tgacacatcc tccagcacag cctacattca gctcagcagc    240

```
ctgacatctg aggactctgc ggtctattac tgtacaagat ctgggggtca gaggttcgac       300
tattggggcc aaggcaccac tctcacagtc tcctca                                336

<210> SEQ ID NO 34
<211> LENGTH: 306
<212> TYPE: DNA
<213> ORGANISM: Unknown
<220> FEATURE:
<223> OTHER INFORMATION: hybridoma

<400> SEQUENCE: 34
cagtctccag caatcatgtc tgcatttaca ggggaaaagg tcaccatgac ctgcagtgcc        60
agctcaagtg tagcttgcat gcactggtac cagcagaagt caagcacctc ccccaaactc       120
ttgatttatg acacatccga actggcttct ggagtcccag gtcgcttcag tggcagtggg       180
tctggaaact cttactctct cacgatcagc agcatggagg ctgaagatgt tgccacttat       240
tactgttttc aggggagtgg gtacccactc acgttcggag ggggaccaa gctggaaata       300 aaacgg                                                                  306

<210> SEQ ID NO 35
<211> LENGTH: 112
<212> TYPE: PRT
<213> ORGANISM: Unknown
<220> FEATURE:
<223> OTHER INFORMATION: hybridoma

<400> SEQUENCE: 35
```

Gln Ser Gly Ser Gly Leu Val Arg Pro Gly Thr Ser Val Lys Leu Ser
1               5                   10                  15

Cys Lys Ala Ser Gly Phe Thr Phe Thr Ser Asn Trp Met His Trp Val
            20                  25                  30

Lys Gln Arg Pro Gly Gln Gly Leu Asp Trp Ile Gly Asn Ile Tyr Pro
        35                  40                  45

Gly Ser Gly Lys Thr Asn Tyr Gly Glu Lys Phe Lys Ser Lys Ala Thr
    50                  55                  60

Leu Thr Val Asp Thr Ser Ser Thr Ala Tyr Ile Gln Leu Ser Ser
65                  70                  75                  80

Leu Thr Ser Glu Asp Ser Ala Val Tyr Tyr Cys Thr Arg Ser Gly Gly
                85                  90                  95

Gln Arg Phe Asp Tyr Trp Gly Gln Gly Thr Thr Leu Thr Val Ser Ser
            100                 105                 110

```
<210> SEQ ID NO 36
<211> LENGTH: 102
<212> TYPE: PRT
<213> ORGANISM: Unknown
<220> FEATURE:
<223> OTHER INFORMATION: hybridoma

<400> SEQUENCE: 36
```

Gln Ser Pro Ala Ile Met Ser Ala Phe Thr Gly Glu Lys Val Thr Met
1               5                   10                  15

Thr Cys Ser Ala Ser Ser Ser Val Ala Cys Met His Trp Tyr Gln Gln
            20                  25                  30

Lys Ser Ser Thr Ser Pro Lys Leu Leu Ile Tyr Asp Thr Ser Glu Leu
        35                  40                  45

Ala Ser Gly Val Pro Gly Arg Phe Ser Gly Ser Gly Ser Gly Asn Ser
    50                  55                  60

```
Tyr Ser Leu Thr Ile Ser Ser Met Glu Ala Glu Asp Val Ala Thr Tyr
65                  70                  75                  80

Tyr Cys Phe Gln Gly Ser Gly Tyr Pro Leu Thr Phe Gly Gly Gly Thr
                85                  90                  95

Lys Leu Glu Ile Lys Arg
            100
```

<210> SEQ ID NO 37
<211> LENGTH: 8
<212> TYPE: PRT
<213> ORGANISM: Unknown
<220> FEATURE:
<223> OTHER INFORMATION: hybridoma

<400> SEQUENCE: 37

```
Gly Phe Thr Phe Thr Ser Asn Trp
1               5
```

<210> SEQ ID NO 38
<211> LENGTH: 8
<212> TYPE: PRT
<213> ORGANISM: Unknown
<220> FEATURE:
<223> OTHER INFORMATION: hybridoma

<400> SEQUENCE: 38

```
Ile Tyr Pro Gly Ser Gly Lys Thr
1               5
```

<210> SEQ ID NO 39
<211> LENGTH: 10
<212> TYPE: PRT
<213> ORGANISM: Unknown
<220> FEATURE:
<223> OTHER INFORMATION: hybridoma

<400> SEQUENCE: 39

```
Thr Arg Ser Gly Gly Gln Arg Phe Asp Tyr
1               5                   10
```

<210> SEQ ID NO 40
<211> LENGTH: 10
<212> TYPE: PRT
<213> ORGANISM: Unknown
<220> FEATURE:
<223> OTHER INFORMATION: hybridoma

<400> SEQUENCE: 40

```
Ser Ala Ser Ser Ser Val Ala Cys Met His
1               5                   10
```

<210> SEQ ID NO 41
<211> LENGTH: 7
<212> TYPE: PRT
<213> ORGANISM: Unknown
<220> FEATURE:
<223> OTHER INFORMATION: hybridoma

<400> SEQUENCE: 41

```
Asp Thr Ser Glu Leu Ala Ser
1               5
```

<210> SEQ ID NO 42
<211> LENGTH: 9
<212> TYPE: PRT

```
<213> ORGANISM: Unknown
<220> FEATURE:
<223> OTHER INFORMATION: hybridoma

<400> SEQUENCE: 42

Phe Gln Gly Ser Gly Tyr Pro Leu Thr
1               5

<210> SEQ ID NO 43
<211> LENGTH: 21
<212> TYPE: DNA
<213> ORGANISM: Homo sapiens

<400> SEQUENCE: 43
caggacgtgt atgatactct a                                             21

<210> SEQ ID NO 44
<211> LENGTH: 21
<212> TYPE: DNA
<213> ORGANISM: Homo sapiens

<400> SEQUENCE: 44
caggctggat tacaacttta a                                             21

<210> SEQ ID NO 45
<211> LENGTH: 27
<212> TYPE: DNA
<213> ORGANISM: Unknown
<220> FEATURE:
<223> OTHER INFORMATION: synthetic oligonucleotide

<400> SEQUENCE: 45
atagacagat gggggtgtcg ttttggc                                       27

<210> SEQ ID NO 46
<211> LENGTH: 21
<212> TYPE: DNA
<213> ORGANISM: Unknown
<220> FEATURE:
<223> OTHER INFORMATION: synthetic oligonucleotide

<400> SEQUENCE: 46
ggatacagtt ggtgcagcat c                                             21

<210> SEQ ID NO 47
<211> LENGTH: 20
<212> TYPE: DNA
<213> ORGANISM: Unknown
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: C or G
<220> FEATURE:
<221> NAME/KEY: misc_feature
<222> LOCATION: (3)..(3)
<223> OTHER INFORMATION: A or G
<220> FEATURE:
<221> NAME/KEY: misc_feature
<222> LOCATION: (6)..(6)
<223> OTHER INFORMATION: any base (not a gap)
<220> FEATURE:
<221> NAME/KEY: misc_feature
<222> LOCATION: (7)..(7)
<223> OTHER INFORMATION: amino A or C
<220> FEATURE:
<221> NAME/KEY: misc_feature
<222> LOCATION: (13)..(13)
```

```
<223> OTHER INFORMATION: C or G
<220> FEATURE:
<221> NAME/KEY: misc_feature
<222> LOCATION: (16)..(16)
<223> OTHER INFORMATION: C or G

<400> SEQUENCE: 47
nangtnnagc tgnagnagtc                                                  20

<210> SEQ ID NO 48
<211> LENGTH: 23
<212> TYPE: DNA
<213> ORGANISM: Unknown
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: C or G
<220> FEATURE:
<221> NAME/KEY: misc_feature
<222> LOCATION: (3)..(3)
<223> OTHER INFORMATION: A or G
<220> FEATURE:
<221> NAME/KEY: misc_feature
<222> LOCATION: (6)..(6)
<223> OTHER INFORMATION: any base (not a gap)
<220> FEATURE:
<221> NAME/KEY: misc_feature
<222> LOCATION: (7)..(7)
<223> OTHER INFORMATION: amino (A or C)
<220> FEATURE:
<221> NAME/KEY: misc_feature
<222> LOCATION: (13)..(13)
<223> OTHER INFORMATION: A or C
<220> FEATURE:
<221> NAME/KEY: misc_feature
<222> LOCATION: (16)..(16)
<223> OTHER INFORMATION: A or C
<220> FEATURE:
<221> NAME/KEY: misc_feature
<222> LOCATION: (21)..(21)
<223> OTHER INFORMATION: A or T

<400> SEQUENCE: 48
nangtnnagc tgnagnagtc ngg                                              23

<210> SEQ ID NO 49
<211> LENGTH: 24
<212> TYPE: DNA
<213> ORGANISM: Unknown
<220> FEATURE:
<223> OTHER INFORMATION: synthetic oligonucleotide
<220> FEATURE:
<221> NAME/KEY: misc_feature
<222> LOCATION: (3)..(3)
<223> OTHER INFORMATION: C or T
<220> FEATURE:
<221> NAME/KEY: misc_feature
<222> LOCATION: (10)..(10)
<223> OTHER INFORMATION: amino(A or C)
<220> FEATURE:
<221> NAME/KEY: misc_feature
<222> LOCATION: (12)..(12)
<223> OTHER INFORMATION: C or G
<220> FEATURE:
<221> NAME/KEY: misc_feature
<222> LOCATION: (15)..(15)
<223> OTHER INFORMATION: amino(A or C)
<220> FEATURE:
<221> NAME/KEY: misc_feature
<222> LOCATION: (18)..(18)
<223> OTHER INFORMATION: A or G
<220> FEATURE:
<221> NAME/KEY: misc_feature
```

```
<222> LOCATION: (19)..(19)
<223> OTHER INFORMATION: A or T
<220> FEATURE:
<221> NAME/KEY: misc_feature
<222> LOCATION: (22)..(22)
<223> OTHER INFORMATION: amino(A or C)
<220> FEATURE:
<221> NAME/KEY: misc_feature
<222> LOCATION: (22)..(22)
<223> OTHER INFORMATION: A or C

<400> SEQUENCE: 49
ganattgtgn tnacncarnc tnca                                           24
```

TUMOR MARKER, MONOCLONAL ANTIBODIES AND METHODS OF USE THEREOF

This application is a U.S. national stage of PCT/EP2014/062419 filed on 13 Jun. 2014, which claims priority to and the benefit of European Application No. EP13172028.6 filed on 14 Jun. 2013, the contents of which are incorporated herein by reference in their entireties.

The present invention relates to the use of the FAT Tumor Suppressor Homolog 1 (FAT1) protein or encoding polynucleotides as markers for the detection of tumors, or as targets for their treatment, particularly of tumors affecting colon, ovary, prostate, esophagus and kidneys. Also provided are affinity ligands capable of selectively interacting with the newly identified markers, as well as methods for tumor diagnosis and therapy using such ligands.

BACKGROUND OF THE INVENTION

Tumor Markers (or Biomarkers)

Tumor markers are substances that can be produced by tumor cells or by other cells of the body in response to cancer. In particular, a protein biomarker is either a single protein or a panel of different proteins that could be used to unambiguously distinguish a disease state. Ideally, a biomarker would have both a high specificity and sensitivity, being represented in a significant percentage of the cases of given disease and not in healthy state.

Biomarkers can be identified in different biological samples, like tissue biopsies or preferably biological fluids (saliva, urine, blood-derivatives and other body fluids) whose collection does not necessitate invasive treatments. Tumor marker levels may be categorized in three major classes on the basis of their clinical use. Diagnostic markers can be used in the detection and diagnosis of cancer. Prognostics markers are indicative of specific outcomes of the disease and can be used to define predictive models that allow the clinicians to predict the likely prognosis of the disease at time of diagnosis. Moreover, prognosis markers are helpful to monitor the patient response to a drug therapy and facilitate a more personalized patient management. A decrease or return to a normal level may indicate that the cancer is responding to therapy, whereas an increase may indicate that the cancer is not responding. After treatment has ended, tumor marker levels may be used to check for recurrence of the tumor. Finally, therapeutic markers can be used to develop tumor-specific drugs or affinity ligand (i.e. antibodies) for a tumor treatment.

Currently, although an abnormal tumor marker level may suggest cancer, this alone is usually not enough to accurately diagnose cancer and their measurement in body fluids is frequently combined with other tests, such as a biopsy and radioscopic examination. Frequently, tumor marker levels are not altered in all of people with a certain cancer disease, especially if the cancer is at early stage. Some tumor marker levels can also be altered in patients with noncancerous conditions. Most biomarkers commonly used in clinical practice do not reach a sufficiently high level of specificity and sensitivity to unambiguously distinguish a tumor from a normal state.

To date the number of markers that are expressed abnormally is limited to certain types/subtypes of cancer, some of which are also found in other diseases. (http://www.cancer.gov/cancertopics/factsheet).

For example, prostate-specific antigen (PSA) levels are often used to screen men for prostate cancer, but this is controversial since elevated PSA levels can be caused by both prostate cancer or benign conditions, and most men with elevated PSA levels turn out not to have prostate cancer.

Another tumor marker, Cancer Antigen 125, (CA 125), is sometimes used to screen women who have an increased risk for ovarian cancer. Scientists are studying whether measurement of CA 125, along with other tests and exams, is useful to find ovarian cancer before symptoms develop. So far, CA 125 measurement is not sensitive or specific enough to be used to screen all women for ovarian cancer. Mostly, CA 125 is used to monitor response to treatment and check for recurrence in women with ovarian cancer. Finally, human epidermal growth factor receptor (HER2) is a marker protein overproduced in about 20% of breast cancers, whose expression is typically associated with a more aggressive and recurrent tumors of this class.

Routine Screening Test for Tumor Diagnosis

Screening tests are a way of detecting cancer early, before there are any symptoms. For a screening test to be helpful, it should have high sensitivity and specificity. Sensitivity refers to the test's ability to identify people who have the disease. Specificity refers to the test's ability to identify people who do not have the disease. Different molecular biology approaches such as analysis of DNA sequencing, small nucleotide polymorphisms, in situ hybridization and whole transcriptional profile analysis have done remarkable progresses to discriminate a tumor state from a normal state and are accelerating the knowledge process in the tumor field. However so far different reasons are delaying their use in the common clinical practice, including the higher analysis complexity and their expensiveness. Other diagnosis tools whose application is increasing in clinics include in situ hybridization and gene sequencing.

Currently, Immuno-HistoChemistry (IHC), a technique that allows the detection of proteins expressed in tissues and cells using specific antibodies, is the most commonly used method for the clinical diagnosis of tumor samples. This technique enables the analysis of cell morphology and the classification of tissue samples on the basis of their immunoreactivity. However, at present, IHC can be used in clinical practice to detect cancerous cells of tumor types for which protein markers and specific antibodies are available. In this context, the identification of a large panel of markers for the most frequent cancer classes would have a great impact in the clinical diagnosis of the disease.

Anti-Cancer Therapies

In the last decades, an overwhelming number of studies remarkably contributed to the comprehension of the molecular mechanisms leading to cancer. However, this scientific progress in the molecular oncology field has not been paralleled by a comparable progress in cancer diagnosis and therapy. Surgery and/or radiotherapy are still the main modality of local treatment of cancer in the majority of patients. However, these treatments are effective only at initial phases of the disease and in particular for solid tumors of epithelial origin, as is the case of colon, breast, ovary, prostate and others, while they are not effective for distant recurrence of the disease. In some tumor classes, chemotherapeutic treatments have been developed, which generally relies on drugs, hormones and antibodies, targeting specific biological processes used by cancers to grow and spread. However, so far many cancer therapies had limited efficacy due to severity of side effects and overall toxicity. Indeed, a major effort in cancer therapy is the development of treatments able to target specifically tumor cells causing limited damages to surrounding normal cells thereby decreasing adverse side effects. Recent developments in cancer therapy in this direction are encouraging, indicating that in some cases a cancer specific therapy is feasible. In particular, the development and commercialization of humanized monoclonal antibodies that recognize specifically tumor-associated markers and promote the elimination of cancer is one of the most promising solutions that appears to be an extremely favorable market opportunity for pharmaceutical companies. However, at present the number of therapeutic antibodies available on the market or under clinical studies is very limited and restricted to specific cancer classes. So far licensed monoclonal antibodies currently used in clinics for the therapy of specific tumor classes show only a partial efficacy and are frequently associated with chemotherapies to increase their therapeutic effect. Administration of Trastuzumab (Herceptin), a commercial monoclonal antibody targeting HER2 in conjunction with Taxol adjuvant chemotherapy induces tumor remission in about 42% of the cases (1). Bevacizumab (Avastin) and Cetuximab (Erbitux) are two monoclonal antibodies recently licensed for use in humans, targeting the endothelial and epithelial growth factors respectively that, combined with adjuvant chemotherapy, proved to be effective against different tumor diseases. Bevacizumab proved to be effective in prolonging the life of patients with metastatic colorectal and breast cancers. Cetuximab efficacy has been demonstrated in patients with tumor types refractory to standard chemotherapeutic treatments (1).

In summary, available screening tests for tumor diagnosis are uncomfortable or invasive and this sometimes limits their applications. Moreover tumor markers available today have a limited utility in clinics due to either their incapability to detect all tumor subtypes of the defined cancers types and/or to distinguish unambiguously tumor vs. normal tissues. Similarly, licensed monoclonal antibodies combined with standard chemotherapies are not effective against the majority of cases. Therefore, there is a great demand for new tools to advance the diagnosis and treatment of cancer.

Cancer Derived Exosomes.

Exosomes are nanoscale (30-100 nm) membrane vesicles formed by "inward/reverse budding" of the limiting membrane of the multivesicular bodies (MVBs) in the late endocytic compartment and released upon the fusion of MVB with the plasma membrane. Exosome secretion is observed from most cell types under both physiological and pathological conditions, particularly tumour cells and hematopoietic cells. Exosomes contain cytosolic and membrane proteins, as well as nucleic acid derived from the parental cells. The protein content is generally enriched for certain molecules, including targeting/adhesion molecules (e.g. tetraspanins, lactadherin and integrins), membrane trafficking molecules (e.g. annexins and Rab proteins), cytoskeleton molecules (e.g. actin and tubulin), proteins involved in MVB formation (e.g. Alix, Tsg101 and clathrin), chaperones (e.g., Hsp70 and Hsp90), signal transduction proteins (e.g. protein kinases, 14-3-3, and heterotrimeric G proteins) and cytoplasmic enzymes (e.g. GAPDH, peroxidases, and pyruvate kinases) (2). Other animal vesicles also contain various active molecules, such as those described above for exosomes. Depending on their cellular origin the protein composition of animal vesicles can be enriched in specific proteins. For instance, tumour-derived animal vesicles usually contain tumor-specific antigens (TAAs) expressed in the parental tumour cells such as melan-A, Silv, carcinoembryonic antigen (CEA), and mesothelin. Thus, cancer vaccine strategies have used tumour-derived exosomes as a source of TAAs to pulse DCs, resulting in the transfer of tumour antigens to DCs that were able to induce tumour-specific CD8+CTL response in mice (3) and humans (4). Methods of altering exosome protein expression are well known and include, for example, genetic modification, inhibition by small molecule inhibitors, enzymes or other inhibitory/activating proteins or peptides, and antisense technology (or other nucleic acid technologies). For example, exosomes can be modified to contain high levels of proinflammatory factors to stimulate Th1-polarized immune responses (2), e.g. by subjecting the cell that the vesicle is derived from to stress conditions under which proinflammatory cytokine and/or Hsp70 levels increase. Alternatively, the parent cell may be modified to reduce the expression of immunosuppressive molecules, such as FasL, TRAIL or TGF-beta. Exosomes can also be modified by incorporation of additional immunogenic proteins e.g. fusion with the superantigen staphylococcal enterotoxin A (SEA) (5).

Experimental Approaches Commonly Used to Identify Tumor Markers

Most popular approaches used to discover new tumor markers are based on genome-wide transcription profile or total protein content analyses of tumor. These studies usually lead to the identification of groups of mRNAs and proteins which are differentially expressed in tumors. Validation experiments then follow to eventually single out, among the hundreds of RNAs/proteins identified, the very few that have the potential to become useful markers. Although often successful, these approaches have several limitations and often, do not provide firm indications on the association of protein markers with tumor. A first limitation is that, since frequently mRNA levels not always correlate with corresponding protein abundance (approx. 50% correlation), studies based on transcription profile do not provide solid information regarding the expression of protein markers in tumor (6, 7, 8, 9, 10).

A second limitation is that neither transcription profiles nor analysis of total protein content discriminate post-translation modifications, which often occur during oncogenesis. These modifications, including phosphorylations, acetylations, and glycosylations, or protein cleavages influence significantly protein stability, localization, interactions, and functions (11).

As a consequence, large scale studies generally result in long lists of differentially expressed genes that would require complex experimental paths in order to validate the potential markers. However, large-scale genomic/proteomic studies reporting novel tumor markers frequently lack of confirmation data on the reported potential novel markers and thus do not provide solid demonstration on the association of the described protein markers with tumor.

SUMMARY OF THE INVENTION

The present invention provides new means for the detection and treatment of colon, ovary, prostate, kidney and esophagus tumors, based on the identification of the FAT Tumor Suppressor Homo log 1 (FAT1) marker specific for these tumor types.

The invention also provides a method for the diagnosis of these cancer types, comprising a step of detecting the above-identified marker in a biological sample, e.g. in a tissue or biological fluid sample of a subject suspected of having or at risk of developing malignancies or susceptible to cancer recurrences.

In addition, the tumor marker identifies a novel target for affinity ligands, which can be used for therapeutic applications. Also provided are specific affinity ligands, particularly antibodies, capable of selectively interacting with the newly identified protein marker expressed on the cell surface. The antibodies can be used to specifically discriminate cancer cells, based on the recognition of the marker. The invention also provides monoclonal antibodies able to recognize the marker on the cell surface and, upon binding, to be internalized by cancer cells. Finally, the invention provides antibodies that can be used to directly kill or promote killing of cancer cells either as unconjugated or conjugated with cell payloads (e.g. radioisotopes, drugs, or toxins).

STATE OF THE ART

General Information.

Human FAT1 gene is an ortholog of the Drosophila fat gene, which encodes a tumor suppressor essential for controlling cell proliferation during Drosophila development. The gene product FAT1 is a member of the cadherin superfamily, a group of integral membrane proteins characterized by the presence of cadherin-type repeats. In addition to containing 34 tandem cadherin-type repeats, the gene product has five epidermal growth factor (EGF)-like repeats and one laminin A-G domain. It was first identified as a tumor suppressor in Drosophila melanogaster, acting via the Salvador-Warts-Hippo signaling pathway (12).

This gene is expressed at high levels in a number of fetal epithelia. Transcript variants derived from alternative splicing and/or alternative promoter usage exist, but they have not been fully described. The protein product probably functions as an adhesion molecule and/or signaling receptor, and is likely to be important in developmental processes and cell communication. FAT1 is known to interact with Ena/VASP, thereby it is involved in promoting actin polymerization and cell motility (13).

Role in Cancer

Scientific literature has reported that FAT1 has a predominant tumor-suppressive effect. The human FAT1 gene is homozygously deleted in 23% of oral cancer cell lines and in 80% of primary oral cancer cases and FAT1 mRNA expression is repressed in oral cancer cell lines due to homozygous deletion and/or promoter CpG hypermethylation (14). Loss of heterozygosity (LOH) of the FAT1 gene occurs in 42% of low-grade diffuse astrocytoma and 63% of glioblastoma multiforme (15). FAT1 mRNA level in ductal carcinoma in situ is significantly higher than that in invasive breast cancer and FAT1 knockdown promotes progression from ductal carcinoma in situ to invasive breast cancer, indicating that lower FAT1 expression is associated with aggressive breast cancers (16).

Available in vitro and in vivo studies reported that FAT1 depletion leads to markedly accelerated cell growth and proliferation, while expression of FAT1 robustly suppresses tumor growth. These growth-suppressive effects are abrogated when mutations observed in tumors are present (17). Recent data now implicates FAT1 mutation as a driver of Wnt activation in many cancers, through the involvement the b-catenin. As other cadherins, FAT1 can bind to b-catenin and limits its translocation to the nucleus. Mutations in FAT1 intracytoplasmic domain result in a loss of this ability to regulate b-catenin. Consequently, loss of FAT1 in cells activates the Wnt signaling pathway, unleashing b-catenin-dependent transcriptional activity and upregulating pro-growth wnt transcriptional targets. Consistent with this, primary cancer samples with FAT1 alterations are characterized by significant enhancement of Wnt signaling. The growth-suppressive functions of FAT1 are mediated by its intracytoplasmic, b-catenin binding domain, but the extracellular domain also mediates cell adhesion, which may be a secondary mechanism by which FAT1 loss promotes tumor growth.

In a recent study on melanoma (18) showed that melanocytes and keratinocytes express FAT1 at similar level. However in melanoma the protein shows an altered processing. In keratinocytes FAT1 is cleaved by the proprotein convertase furin forming two fragments of 430 and 85 kDa that form a non-covalent heterodimer before achieving cell surface expression. Differently, in melanoma cells, the non-cleaved proform of FAT1 is also expressed at the cell surface together with the furin-cleaved heterodimer. Moreover, furin-independent processing generates an aberrant proteolytic product of 65-kDa no longer in association with the extracellular fragment. In vitro localization studies of FAT1 showed that melanoma cells display high levels of cytosolic FAT1 protein, whereas keratinocytes, despite comparable FAT1 expression levels, exhibited mainly cell-cell junctional staining. These differences in protein distribution are compatible with the different protein products generated by dual FAT1 processing. The authors suggest that the uncleaved FAT1 could promote altered signaling, and the novel products of alternate processing provide a dominant negative function in melanoma.

Only few examples of FAT1 upregulation in cancer have been so far reported. FAT1 mRNA expression is upregulated in 11% of acute myeloid leukemia (AML), 29% of preB acute lymphoblastic leukemia (ALL) and 63% of T-ALL, and FAT1 upregulation in preB-ALL is associated with shorter relapse-free survival as well as shorter overall survival (19). FAT1 immunoreactivity is strong in 29% of cholangiocarcinoma (20).

Thus, it is conceivable that FAT1 has a multifaceted role such that it may operate in different mechanisms, and may act as a tumor suppressive or oncogenic depending on the specific cell context and in a manner that cannot be predicted based on available knowledge.

Despite the involvement of FAT1 in tumor has been partially investigated, so far no previous evidence documents the FAT1 association with colon, ovary, kidney, esophagus and prostate tumors. In particular, no study reports FAT1 over-expression in these cancers. Finally, FAT1 antibodies able to recognize FAT1 over-expressed on the surface of colon, ovary, kidney, esophagus and prostate cancers and reduce cancer growth have not been reported so far.

DISCLOSURE OF THE INVENTION

The present invention is based on the surprising finding that FAT1 is over-expressed and acts as tumor promoter in colon, ovary, kidney, esophagus and prostate cancers. Moreover, it was found that antibodies specific for FAT1 are able to specifically recognize colon, ovary, esophagus, prostate and kidney tumor tissues from patients, while they show negative or very poor staining in corresponding normal tissues.

Accordingly, the present invention provides FAT1 as a protein marker for colon, ovary, esophagus, kidney, and prostate tumors and in general for cancers of these types. Antibodies generated towards the FAT1 protein show a selective immunoreactivity in histological preparation of colon, ovary, esophagus, prostate and kidney cancer tissues with concomitant negligible expression in corresponding normal samples, which indicates a specific over-expression of FAT1 protein in these cancer samples, and makes FAT1 protein and specific antibodies thereto novel tools for specifically distinguishing these cancer types from a normal state.

Antibodies generated against FAT1 are able to specifically recognize the protein on the surface of different cancer cell lines. In particular, experiments carried out with two specific anti-FAT1 antibodies showed that the latter, upon surface binding, are efficiently internalized by cancer cells, indicating that they are suitable for the generation of antibody-drug conjugate (ADC). In addition one of these antibodies, when administered to mice bearing tumor, is able to reduce cancer growth.

Finally, antibodies generated against FAT1 are also able to detect the protein in exosomes from cancer cells, indicating that the marker can be detected in biological fluids of oncologic patients. The exosomes carrying FAT1 can be exploited as tools for the development of vaccines to prevent or treat cancers affecting colon, ovary, esophagus, kidney, and prostate.

Overall, these findings indicate that FAT1 can be conveniently used as a diagnostic marker as well as a target for anti-cancer therapies (e.g. based on small molecules, antibodies, nucleic acids, toxins) and cancer vaccines. Moreover, they provide experimental evidences that the FAT1 antibodies can be exploited as novel therapeutic agents.

Hence, in a first aspect, the invention provides the use of a marker for colon, ovary, esophagus, kidney, and prostate tumor, which is selected from:

(i) FAT1 protein, in one of its isoforms SEQ ID NO:1, SEQ ID NO:2, SEQ ID NO:3, SEQ ID NO:4, SEQ ID NO:5, or a different isoform having sequence identity of at least 80%, preferably at least 90%, more preferably at least 95% to SEQ ID NO:1, SEQ ID NO:2, SEQ ID NO:3, SEQ ID NO:4, SEQ ID NO:5, or (ii) a RNA molecule coding for a FAT1 protein, wherein the encoding sequence is preferably selected from SEQ ID NO:6, SEQ ID NO:7, SEQ ID NO:8, SEQ ID NO:9 and SEQ ID NO:10 or from complementary sequences thereof.

As used herein the "% amino acid sequence identity" with respect to the marker protein sequences identified herein indicates the percentage of amino acid residues in a protein variant or iso form, or in a portion thereof, that are identical to the amino acid residues in the specific marker sequence, after aligning the sequences and introducing gaps, if necessary, to achieve the maximum percent sequence identity, and not considering any conservative substitution as part of the sequence identity.

Identity between nucleotide sequences is preferably determined by the Smith-Waterman homology search algorithm as implemented in the SSEARCH program (Oxford Molecular), using an affine gap search with parameters gap open penalty=12 and gap extension penalty=1.

A further aspect of this invention is a method of screening a tissue sample for malignancy, which comprises determining the presence in said sample of the above-mentioned tumor marker. This method includes detecting either the marker protein, e.g. by means of labeled monoclonal or polyclonal antibodies that specifically bind to the target protein, or the respective mRNA, e.g. by means of polymerase chain reaction techniques such as RT-PCR. The methods for detecting proteins in a tissue sample are known to one skilled in the art and include immunoradiometric, immunoenzymatic or immunohistochemical techniques, such as radioimmunoassays, immunofluorescent assays or enzyme-linked immunoassays. Other known protein analysis techniques, such as polyacrylamide gel electrophoresis (PAGE), Western blot or Dot blot are equally suitable.

Preferably, the detection of the protein marker is carried out with the immune-histochemistry technology, particularly by means of High Through-Put methods that allow the analyses of the antibody immune-reactivity simultaneously on different tissue samples immobilized on a microscope slide. Briefly, each Tissue Micro Array (TMA) slide includes tissue samples suspected of malignancy taken from different patients, and an equal number of normal tissue samples from the same patients as controls. The direct comparison of samples by qualitative or quantitative measurement, e.g. by enzymatic or colorimetric reactions, allows the identification of tumors.

In one embodiment, the invention provides a method of screening a sample of colon, ovary, esophagus, kidney, and prostate tissue for malignancy, which comprises determining the presence in said sample of the FAT1 protein tumor marker, variants or iso forms thereof as described above.

A further aspect of the invention is a method in vitro for determining the presence of a colon, ovary, esophagus, kidney, or prostate tumor in a subject, which comprises the steps of:

(a) providing a test sample which is a sample of tissue suspected of containing tumor cells or a biological fluid sample preferably containing exosomes of the suspected tumor cells;

(b) determining the amount of FAT1 tumor marker in the test sample;

(c) comparing said amount of tumor marker with that obtained in a control sample from healthy subjects;

wherein an increased amount of tumor marker in the test sample compared to the control sample is indicative of a tumor state in the subject.

The control sample may be a colon, ovary, esophagus, kidney or prostate tissue sample from healthy individuals.

In alternative to detecting altered FAT1 expression level, the test sample can be assayed for processed form of the protein marker or for differential expression of the respective mRNA transcripts.

The methods and techniques for carrying out the assay are known to one skilled in the art and are preferably based on immunoreactions for detecting proteins and on PCR methods for the detection of mRNAs. The same methods for detecting proteins or mRNAs from a tissue sample as disclosed above can be applied.

A further aspect of this invention is the use of the FAT1 tumor marker herein provided as target for the identification of candidate antitumor agents for the treatment of colon, ovary, kidney, esophagus or prostate cancers. Accordingly, the invention provides a method for screening compounds which comprises contacting cells expressing the FAT1 protein from colon, ovary, kidney, esophagus or prostate tissues, with the test compound, and determining the binding of said compound to said tumor-associated protein or the cellular or intracellular effects elicited by that interaction. In addition, the ability of the test compound to modulate the activity of each target molecule can be assayed.

A further aspect of the invention is an antibody or a fragment thereof, which is able to specifically recognize and bind to one of the FAT1 tumor-associated proteins described above, for use in a method in vitro for determining the presence of a colon, ovary, esophagus, kidney or prostate tumor as defined above or for use in the treatment of the same tumors. The term "antibody" as used herein refers to any type of immunoglobulins, including IgG, IgM, IgA, IgD and IgE and it may be selected from the group consisting of a polyclonal antibody; a monoclonal antibody including a Human Engineered antibody; a humanized antibody; a human antibody; a chimeric antibody; Fab, F(ab')2; Fv; Sc Fv or SCA antibody fragment; a diabody; linear antibody; or a mutein of any one of these antibodies.

The antibodies may be of various origin, including human, mouse, rat, rabbit and horse, or chimeric antibodies. The production of antibodies is well known in the art. For the production of antibodies in experimental animals, various hosts including goats, rabbits, rats, mice, and others, may be immunized by injection with polypeptides of the present invention or any fragment or oligopeptide or derivative thereof which has immunogenic properties or forms a suitable epitope. Monoclonal antibodies may be produced following the procedures described in Kohler and Milstein, Nature 265:495 (1975) or other techniques known in the art.

In a preferred embodiment, the invention provides an isolated antibody or fragment thereof which specifically binds the FAT1 protein, wherein the heavy- and light-chain variable regions of said antibody contain complementarity determining regions 1, 2 and 3 (CDR-H 1-3 and CDR-L 1-3, respectively) and:

said CDR-H 1-3 comprises the amino acid sequences set forth in SEQ ID NOs:17, 18 and 19, respectively, or an amino acid sequence identical to: SEQ ID NO:17 by at least 60%, preferably at least 85%; SEQ ID NO:18 by at least 85%, preferably at least 90%; and to SEQ ID NO:19 by at least 90%, preferably at least 95%;

said CDR-L 1-3 comprises the amino acid sequences set forth in SEQ ID NOs:20, 21 and 22, respectively, or an amino acid sequence identical to: SEQ ID NO:20 by at least 80%, preferably at least 90%; SEQ ID NO:21 by at least 85%, preferably at least 90%; and to SEQ ID NO:22 by at least 88%, preferably at least 95%.

In a further preferred embodiment, said CDR-H 1-3 contain the amino acid sequences SEQ ID NOs:37, 38 and 39, respectively, and said CDR-L 1-3 contain the amino acid sequences SEQ ID NOs:40, 41 and 42, respectively.

In another preferred embodiment said CDR-H 1-3 and CDR-L 1-3 are encoded by the polynucleotides SEQ ID NOs:11-13 and SEQ ID NOs:14-16, respectively, or variants thereof due to the degeneracy of genetic code.

In another preferred embodiment the antibody of invention contains the heavy and light chains set forth in SEQ ID NO:25 and SEQ ID NO:26, respectively, or heavy and light chain sequences identical to SEQ ID NOs:25 or 26 by at least 85%, preferably at least 95%.

In a likewise preferred embodiment, the antibody of invention contains the heavy and light chains set forth in SEQ ID NO:35 and SEQ ID NO:36, respectively, or heavy and light chain sequences identical to SEQ ID NOs:35 and 36 by at least 85%, preferably at least 95%.

In another preferred embodiment, the heavy and light chains of the invention antibody are encoded by the polynucleotides of SEQ ID NOs:23 and 24, respectively, or variants thereof due to the degeneracy of genetic code.

In yet another preferred embodiment, the heavy and light chains of the invention antibody are encoded by the polynucleotides of SEQ ID NOs:33 and 34, respectively, or variants thereof due to the degeneracy of genetic code.

In related embodiments, the invention antibody comprises a modified or unmodified constant region of a human IgG1, IgG2, IgG3 or IgG4. In a preferred embodiment, the constant region is human IgG1, yet more preferably IgG1k which may optionally be modified to enhance or decrease certain properties. In the case of IgG1, modifications to the constant region, particularly the hinge or CH2 region, may increase or decrease effector function, including ADCC and/or CDC activity.

Epitope-mapping was carried out on FAT1 molecule to identify the molecule regions recognized by monoclonal antibodies on cancer cells. Overlapping fragments were isolated and further investigated for more accurate epitope identification and eventually a region of FAT1 molecule including cadherin domains 8 and 12 and a panel of shorter peptides were identified and validated as FAT1 epitopes in ELISA and FACS competition experiments.

Accordingly, in a further embodiment the invention provides a FAT1 epitope which is selected from the group consisting of SEQ ID NOs: 27, 28, 29, 30, 31 and 32, or peptide sequences identical to SEQ ID NOs: 27, 28, 29, 30, 31 and 32 by at least 48%, preferably at least 75%, more preferably at least 84%, and the use thereof as tumor antigens for rising an immune response against FAT1-expressing tumors. For example, the FAT1 epitope could be used to generate antibodies or T lymphocytes able to impair growth of FAT1-expressing tumors.

In a yet further embodiment the invention provides an isolated monoclonal antibody or fragment thereof which specifically binds to one or more of said FAT1 protein epitopes.

In a preferred embodiment, the monoclonal antibody or fragment thereof contains the CDR-H, CDR-L, heavy and light chain sequences specified above.

Chimeric monoclonal antibodies, in which the variable Ig domains of a mouse monoclonal antibody are fused to human constant Ig domains, can be generated using standard procedures known in the art (See Morrison, S. L., et al. (1984) Chimeric Human Antibody Molecules; Mouse Antigen Binding Domains with Human Constant Region Domains, Proc. Natl. Acad. Sci. USA 81, 6841-6855; and, Boulianne, G. L., et al, Nature 312, 643-646. (1984)).

Humanized antibodies may be achieved by a variety of methods including, for example: (1) grafting the non-human complementarity determining regions (CDRs) onto a human framework and constant region (a process referred to in the art as humanizing through "CDR grafting"), or, alternatively, (2) transplanting the entire non-human variable domains, but "cloaking" them with a human-like surface by replacement of surface residues (a process referred to in the art as "veneering").

The antibodies to the tumor markers of the invention can be used to detect the presence of the marker in histologic preparations or to distinguish tumor cells from normal cells. To that purpose, the antibodies may be labeled with radioactive, fluorescent or enzyme labels.

In addition, the antibodies of the invention can be used for treating proliferative diseases by modulating, e g inhibiting or abolishing the activity of the target protein according to the invention.

Therefore, in a further aspect the invention provides the use of antibodies to FAT1 protein for the preparation of a therapeutic agent for the treatment of proliferative diseases of colon, ovary, esophagus, kidney and prostate tissues. For use in therapy, the antibodies can be formulated with suitable carriers and excipients, optionally with the addition of adjuvants to enhance their effects.

A further aspect of the invention relates to a diagnostic kit containing suitable means for detection, in particular FAT1 polypeptides or polynucleotides, antibodies or fragments or derivatives thereof described above, reagents, buffers, solutions and materials needed for setting up and carrying out the immunoassays, nucleic acid hybridization or PCR assays described above. Parts of the kit of the invention can be packaged individually in vials or bottles or in combination in containers or multicontainer units.

In a further embodiment, the invention provides a pharmaceutical composition containing an antibody to a FAT1 protein or a fragment thereof as herein disclosed, for use in a method of treatment of subjects affected by colon, ovary, esophagus, kidney, or prostate tumor.

In a further embodiment, the invention provides a method for suppressing or reducing the expression of the FAT1 protein in a subject affected by a colon, ovary, esophagus, kidney or prostate tumor, which comprises administering to that subject a siRNA molecule having a sequence complementary to SEQ ID NOs: 6-10.

Graph represents the percentage of cancer samples showing positive IHC reactivity to mAb91.3. As shown in the graph, FAT1 is over-expressed in approximately 80% of colon cancer, 18% of ovary cancer, 20% of esophagus and kidney carcinoma, and 100% of prostate cancer.

Figure 2:
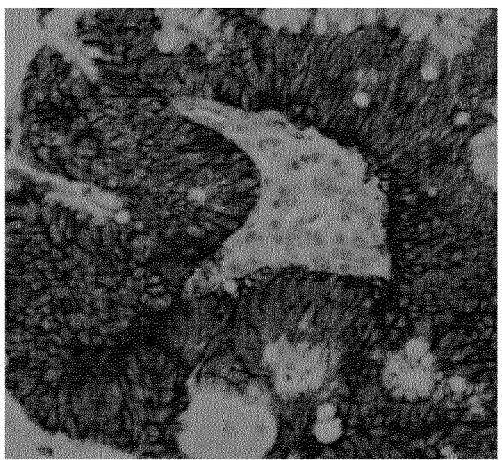
Figure 2:
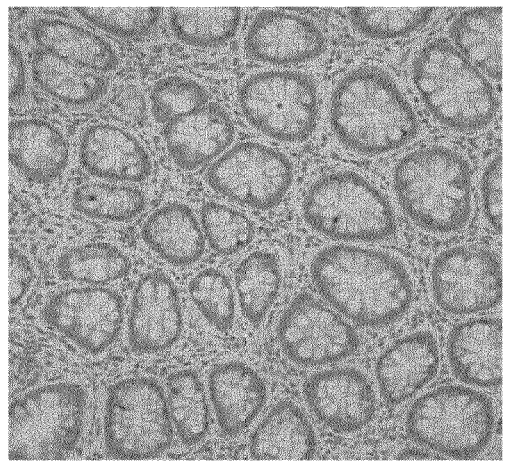
Figure 2:
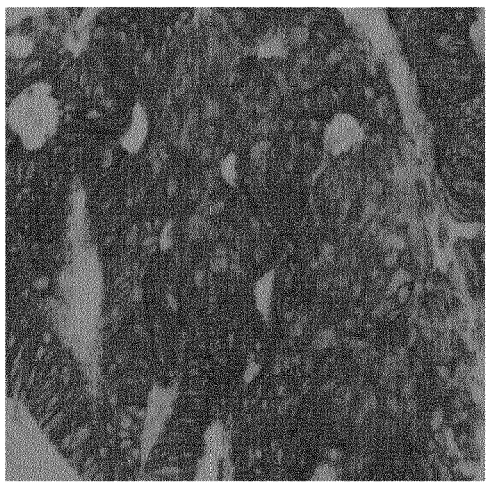
Figure 2:
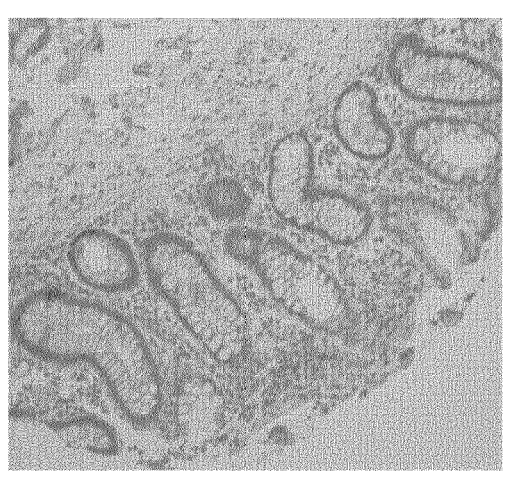

FIG. 2. The anti-FAT1 mAb91.3 specifically recognizes FAT1 over-expressed in colon cancer by IHC.

IHC images of colon tumor and normal colon tissue samples stained with the anti-FAT1 monoclonal antibody mAb91.3. The antibody stains specifically tumor cells, visible in dark gray.

Figure 3:
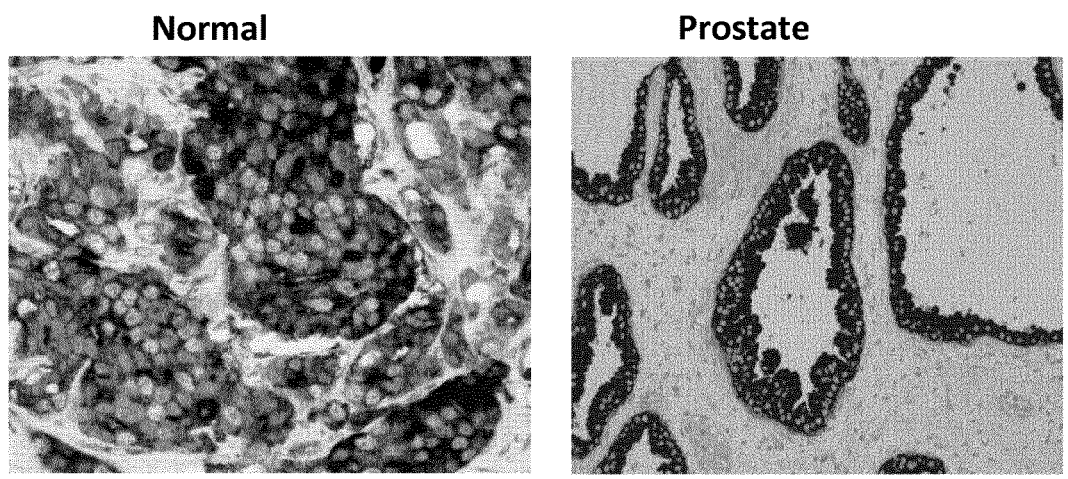

FIG. 3. The anti-FAT1 mAb91.3 recognizes FAT1 over-expressed in prostate cancer by IHC. IHC images of prostate tumor (lower panel) and normal tissue samples (upper panel) stained with the anti-FAT1 antibody mAb91.3. The antibody mAb91.3 stains specifically tumor cells, visible in dark gray.

Figure 4:
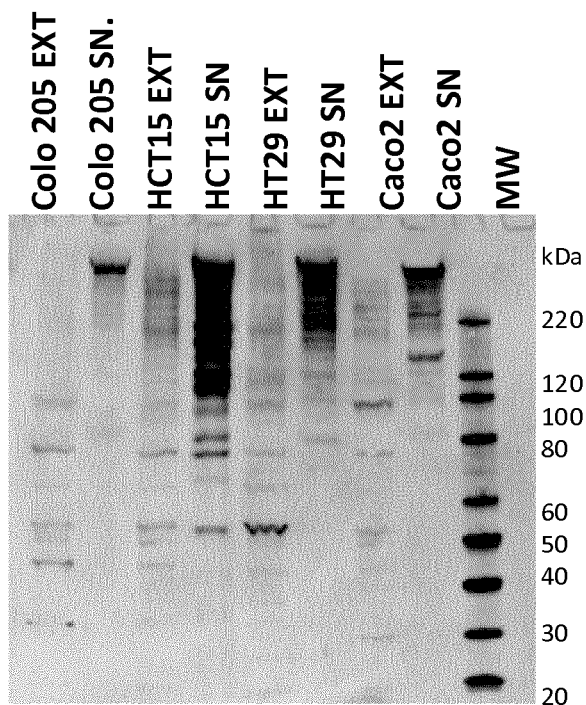

FIG. 4. FAT1 is expressed of in colon tumor cell lines.

Western blot analysis of total protein extracts (corresponding to $2\times10^5$ cells) from colon cancer cell lines. Cell extracts (EXT) and culture supernatants (SN) were separated by SDS-PAGE, transferred onto nitrocellulose membranes and probed with mAb91.3. FAT1 is detected at very high molecular weight bands. Moreover, possible degradation products are also visible. Molecular weight markers are reported on the right.

Figure 5:
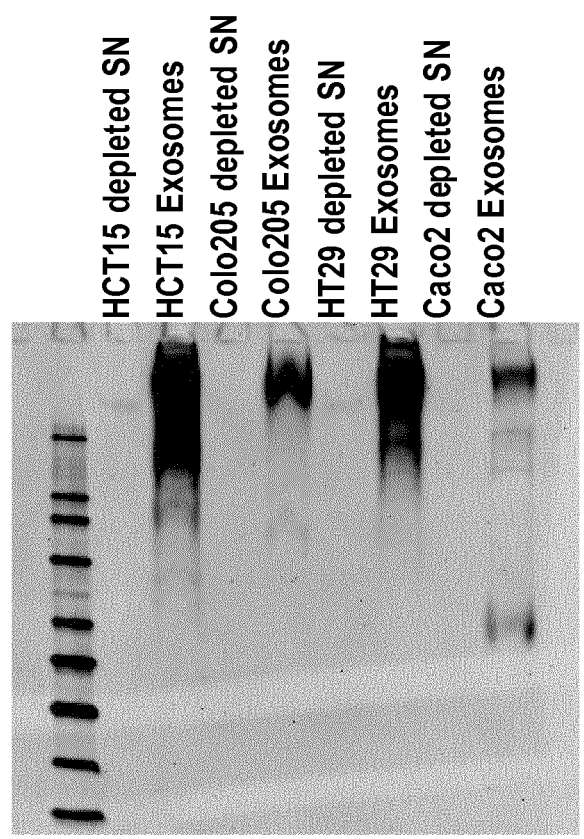

FIG. 5. FAT1 is associated to cell derived exosomes.

Western blot analysis of the exosomal fraction and the exosome-depleted supernatant derived from colon cancer cells stained with the anti-FAT1 monoclonal antibody. Molecular weight markers are reported on the left. The protein mainly associated with exosomes and is detectable at low level in the exosome-depleted supernatant FIG. 6. FAT1 is exposed on the surface of colon cancer cells.

FAT1 surface expression was confirmed by confocal microscopy and flow cytometry of different colon cell lines stained with the anti-FAT1 mAb91.3 or unrelated antibodies. A) Confocal microscopy analysis. Cells were fixed with 3% formaldehyde and incubated with mAb91.3 or an irrelevant mouse monoclonal antibody. The antibody binding was detected by incubation with an Alexa 488-conjugated goat anti-mouse antibody. DAPI was used to visualize nuclei, visible in the left images. Arrows mark examples FAT1 staining visible at the cell surface with mAb91.3. B) FACS. Cells were incubated with mAb91.3 (white peaks) or an irrelevant mouse monoclonal antibody (grey peaks). The antibody binding was detected by incubation with an R-Phycoerythrin (PE)-conjugated secondary antibody. X axis, Fluorescence scale; Y axis, Cells (expressed as % relatively to major peaks).

FIG. 7. Specificity of the anti-FAT1 antibody.

HCT15 cells were transfected with two FAT1 specific siRNA or a scrambled siRNA and the loss of expression and protein disappearance from the cell surface was assessed respectively by Western blot (left panel) and flow cytometry (right panel), using mAb91.3 and two additional anti-FAT1 antibodies that were negative on cancer tissues. Actin and CD81-specific antibodies were used as internal reference for immunoblot or flow cytometry surface staining. As shown in the figure, both antibodies specifically detect FAT1.

Figure 8A:
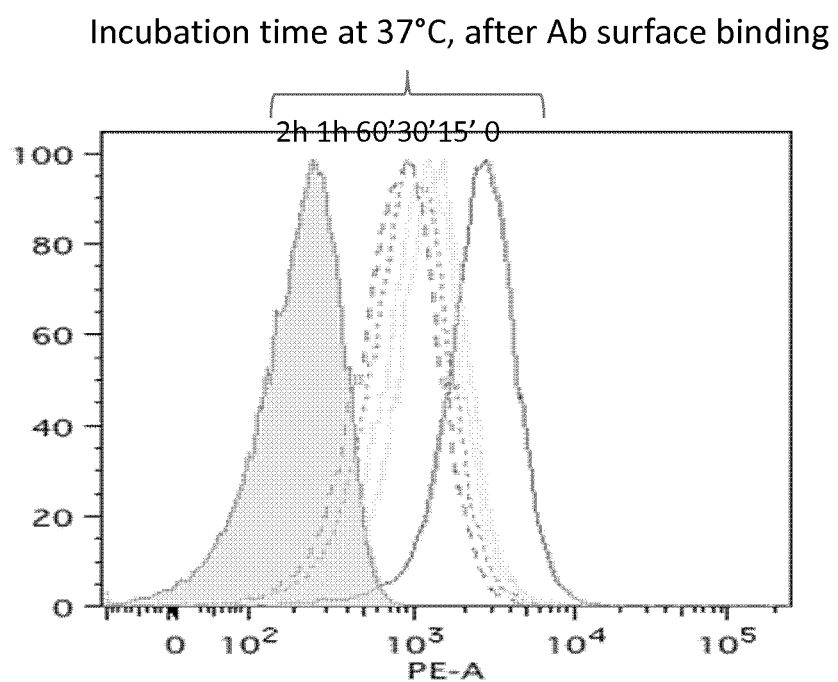
Figure 8B:
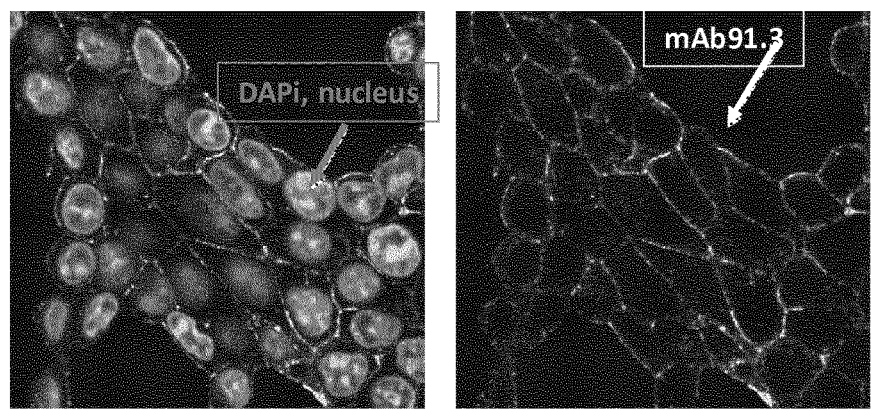
Figure 8B:
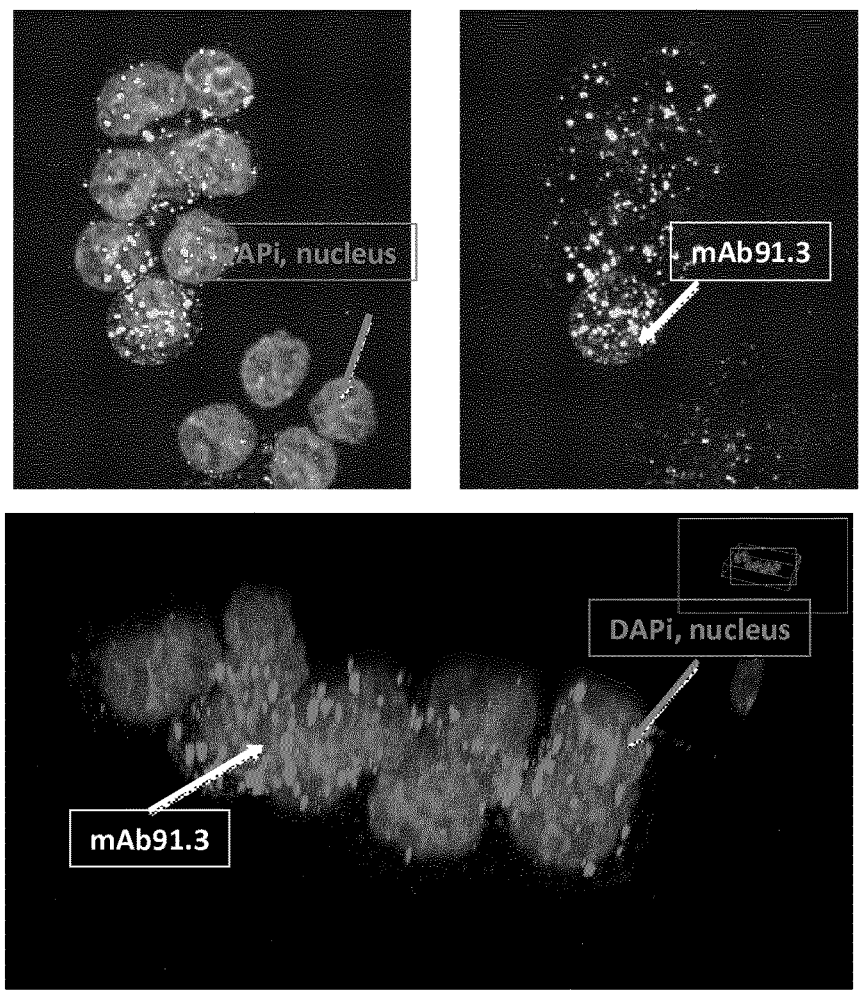

FIG. 8. mAb91.3 is internalized by colon cancer cells.

mAb91.3 (10 micrograms/ml) was incubated with cells 30' at 4° C. to allow surface binding. Then cells were shifted for 1 hour at 37° C. to permit the antibody internalization. A) At defined time-points mAb91.3 disappearance from the cell surface was monitored by flow cytometry with R-Phycoerythrin (PE)-conjugated secondary antibody. B) Confocal microscopy analysis was also used to monitor the loss of antibody from the cell surface and the concomitant accumulation of antibody complexes in the intracellular compartments of cells permeabilized with cold methanol and incubated with α-mouse AlexaFluor488-conjugated secondary antibody. DAPI was used to visualize nuclei. Upper and lower images show 2D and 3D representations, respectively.

Figure 9:
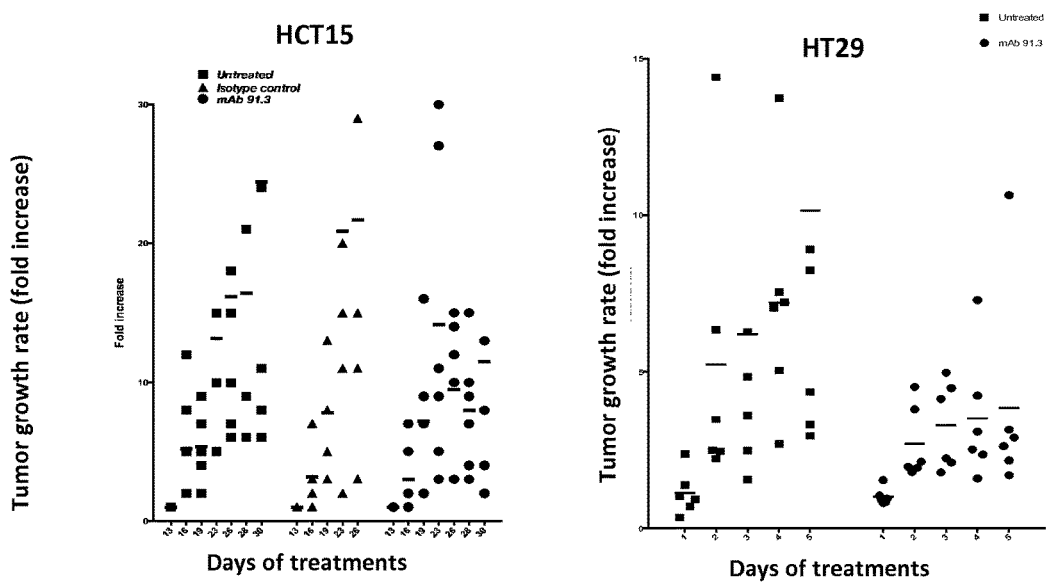
Figure 9:
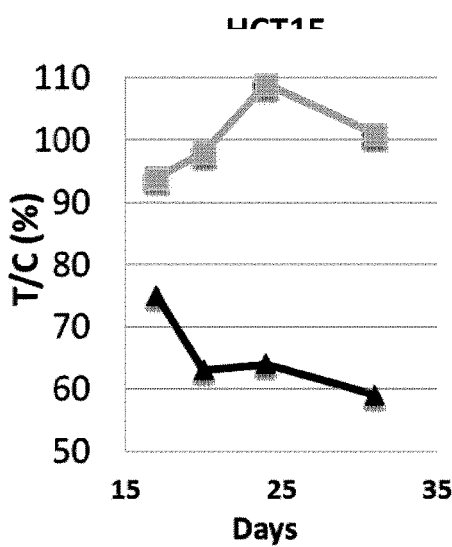

FIG. 9. The anti-FAT1 mAb91.3 specifically binds colon cancer and reduces its growth in xenograft colon mouse models.

A) mAb therapeutic activity. HCT15 and HT29 colon cancer cells were engrafted subcutaneously in athymic nude mice (6 per group) and when they reached approx. 60-100 $mm^3$ mice were administered intravenously with either mAb91.3 or an irrelevant mAb as isotype control (300 micrograms/dose, equal to approximately 12 mg mAb per Kg of animal weight, 3 doses per week). Tumor growth measured with a caliper over a 2 week-period. Graph represents the tumor growth rate. For each mouse tumor growth rate was calculated by dividing the tumor volume at time points vs the tumor volume before treatment start. Horizontal bars represent mean values of each animal group (squares, untreated; triangles, isotype control; circles, mAb91.3).

B) Preventive activity. HCT15 colon cancer cells were engrafted subcutaneously in athymic nude mice (8 per group). The day before and subsequently mice were administered intravenously with either mAb91.3 or an isotype control irrelevant antibody at the indicated dose regimen. Graph represents the tumor mass ratio at time points between treated and control mice for the irrelevant isotype control (gray square) or the mAb91.3 (black triangles). The specificity of mAb91.3 antibody binding on cancer xenografts was monitored by Near-Infrared (NI) Optical Imaging in mice injected NI-labelled antibodies.

Figure 10:
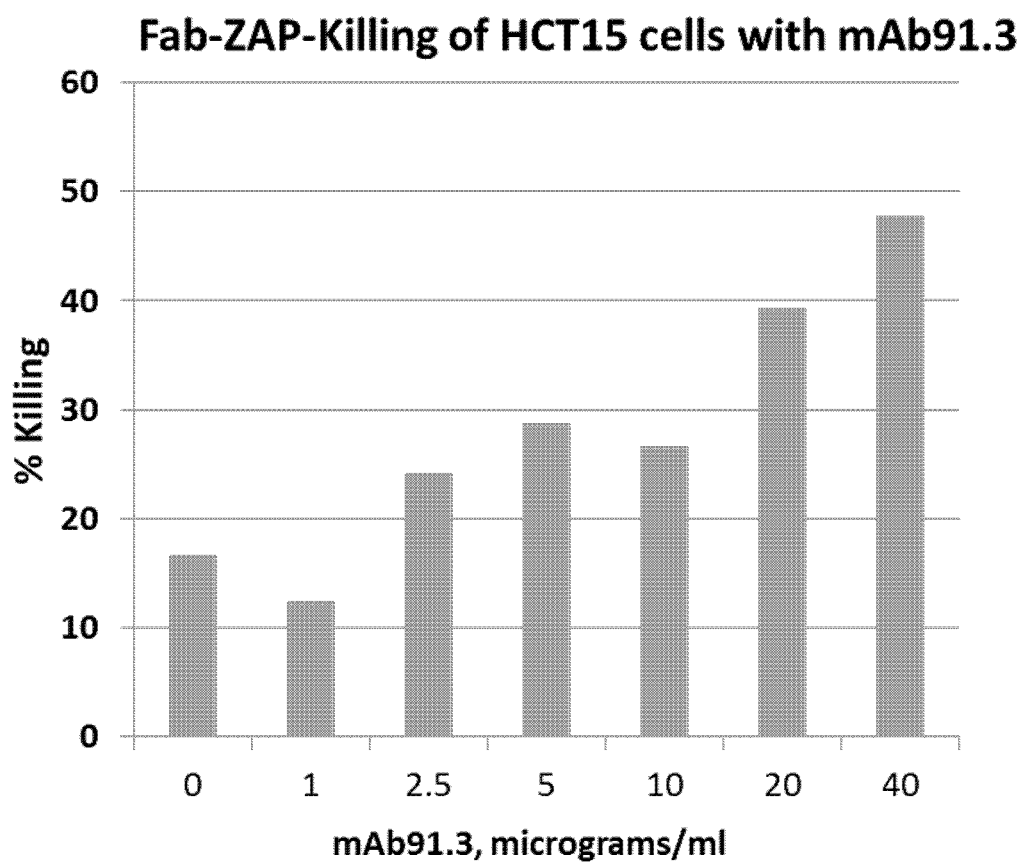

FIG. 10. The anti-Fat1 mAb91.3 promotes killing of cancer cells in an indirect saporin killing assay.

HCT15 cells were incubated with different concentrations of mAb91.3 for 30' at 4° C. Cells were washed with PBS to remove unbound antibody and further incubated for 30' with a saporin-conjugated secondary antibody (ATS system). Afterwards, cells were shifted at 37° C. for 72 hours. Cell viability was assessed with the MTT.

Figure 11:
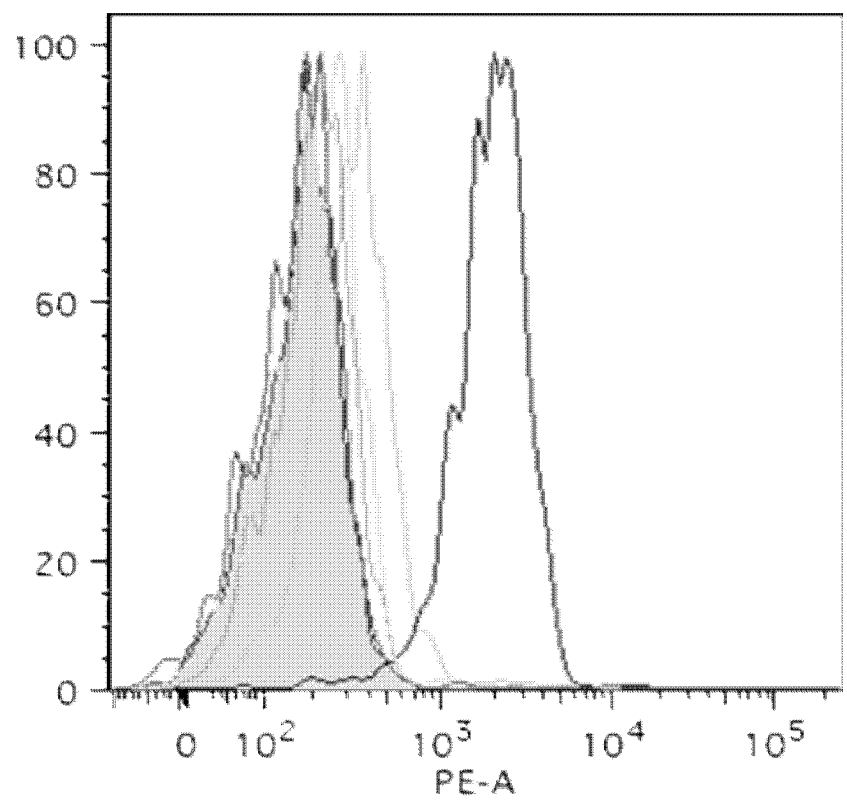

FIG. 11. mAb91.4 binds the surface of colon cancer and is internalized upon binding Cells were incubated with mAb91.4 (10 micrograms/ml) was incubated with cells 30' at 4° C. to allow surface binding. Then cells were shifted for 1 hour at 37° C. to permit the antibody internalization. The antibody binding was detected by FACS by incubation with an R-Phycoerythrin (PE)-conjugated secondary antibody. X axis, Fluorescence scale; Y axis, Cells (expressed as % relatively to major peaks). At defined time-points mAb91.4 disappearance from the cell surface was monitored by FACS as described before.

Figure 12:
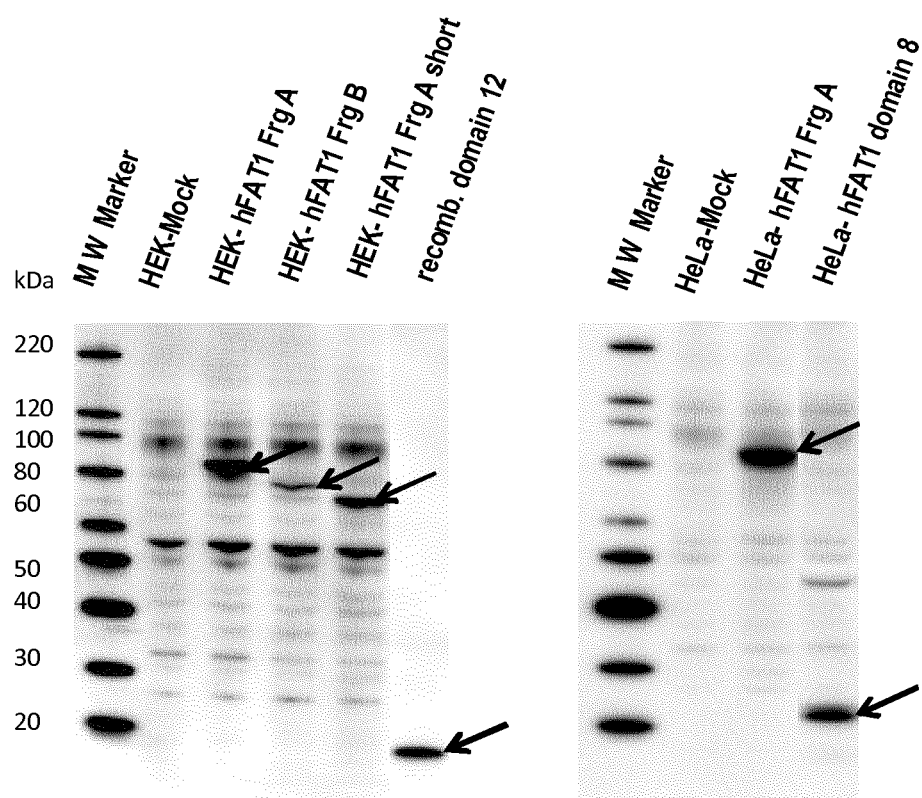

FIG. 12. mAb91.3 binds two FAT1 regions in Western blot. Western blot analysis of HEK-293T or Hela cells transfected with a plasmid encoding the FAT1 fragments. Cells were transfected with plasmids encoding Fat1 fragment A, Fragment B, the short form of fragment A lacking the overlapping region with Fragment B, Domain 8 or the empty vector (mock). After 48 hours cell were lysed and total extracts were loaded on PAGE-SDS, along with recombinant domain 12, and subjected to Western blot using mAb91.3.

Figure 13:
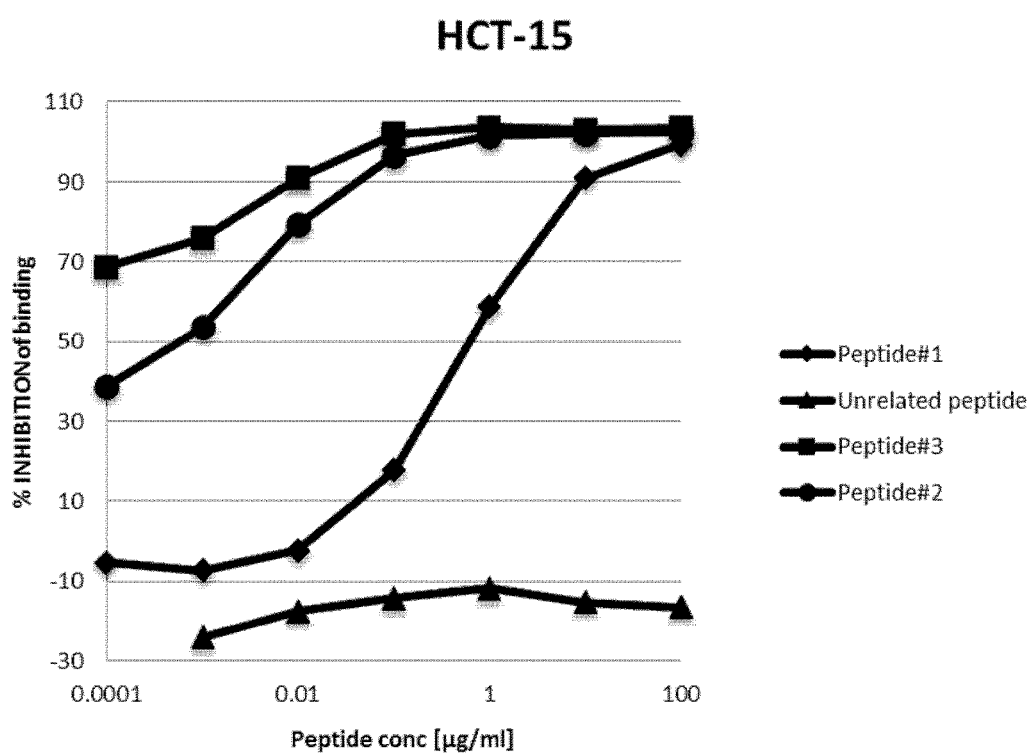

FIG. 13. Identification of mAb91.3 surface exposed epitopes by FACS peptide competition.

HCT15 cells were incubated with mAb 91.3 in the presence of different concentration of the 25 mer FAT1 peptides encompassing the epitopes and an irrelevant peptide. The residual antibody binding on the cell surface was assessed by FACS.

Figure 14:
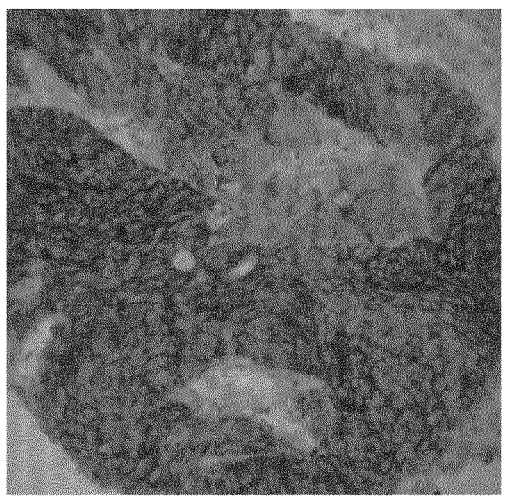
Figure 14:
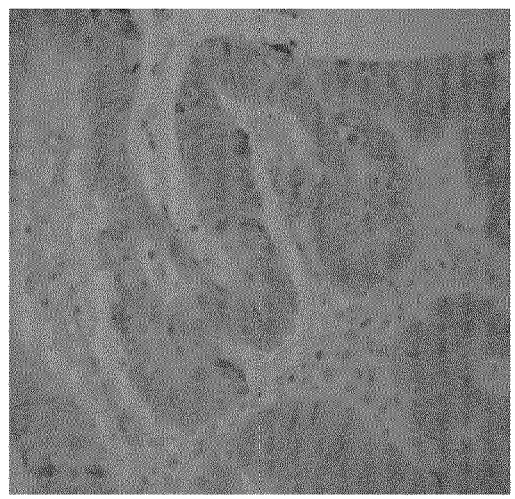

FIG. 14. Identification of the mAb91.3 peptides recognized in colon cancer by IHC peptide competition.

Representative IHC image of colon tumor and normal colon tissue samples stained with the anti-FAT1 monoclonal antibody mAb91.3 (5 micrograms/ml) in the presence of one of the 25 mer peptides encompassing the antibody epitope.

Figure 15:
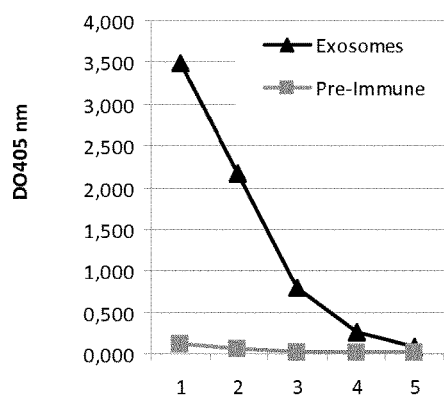
Figure 15:
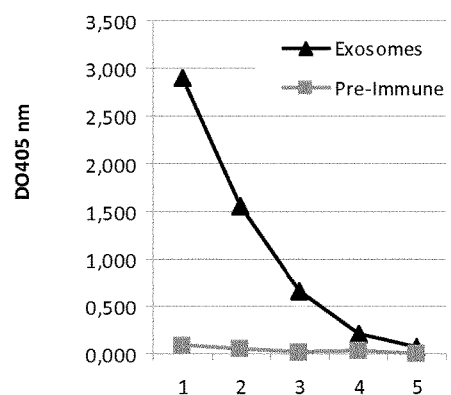

FIG. 15. Total IgGs elicited by the HCT15 exosomes formulations against FAT1. Groups of CD1 mice were immunized with exosomes (15 micrograms dose, three doses) purified from the culture supernatant of HCT15. Two weeks after the last immunization mice were bled and serum was collected. Sera from mice immunized with exosomes were pooled and analyzed by ELISA on two recombinant FAT1 domains as compared to pre-immune sera

EXAMPLES

Example 1. Discovery and Confirmation of FAT1 Over-Expression in Cancer by Immune-Histochemistry A proprietary collection of polyclonal and monoclonal antibodies raised against human recombinant proteins was used to identify proteins over-expressed in cancer by immune-histochemistry (IHC). The antibody library was used screen clinical samples by Tissue Micro Array (TMA), a miniaturized immuno-histochemistry technology suitable for HTP analysis that allows to analyse the antibody immuno-reactivity simultaneously on different tissue samples immobilized on a microscope slide. Since the TMAs include both tumor and healthy tissues, the specificity of the antibodies for the tumors can be immediately appreciated. The use of this technology, differently from approaches based on transcription profile, has the important advantage of giving a first hand evaluation on the potential of the markers in clinics. Conversely, since mRNA levels not always correlate with protein levels (approx. 50% correlation), studies based on transcription profile do not provide solid information regarding the expression of protein markers.

Methods

The tissue microarrays were prepared containing formalin-fixed paraffin-embedded cores of human tissues from patients affected by breast, colon, lung, ovary, esophagus, kidney, and prostate cancers and corresponding normal tissues as controls and subsequently analyzed using the specific antibody sample. For each tumor class two TMA designs were generated and used for IHC with the anti-FAT1 mAb91.3. A first TMA design consisted in pathological and normal tissue samples from 5 patients of known clinical history per each of the five organs (all samples in duplicate) and was used to identify promising target molecules differentially expressed in cancer and normal cells. The direct comparison between tumor and normal tissues of each patient allowed the identification of antibodies that stain specifically tumor cells and provided indication of target expression in tumor. A second expanded TMA design represented samples from 50 patients from each of the five organs and was used to confirm the marker over-expression in the cancer in which the antibody showed specific reactivity.

Corresponding whole tissue sections were examined to confirm diagnosis and tumor classification, and to select representative areas in donor blocks. Normal tissues were defined as microscopically normal (non-neoplastic) and were generally selected from specimens collected from the vicinity of surgically removed tumors. The TMA production was performed essentially as previously described (21, 22). Briefly, a hole was made in the recipient TMA block. A cylindrical core tissue sample (1 mm in diameter) from the donor block was acquired and deposited in the recipient TMA block. This was repeated in an automated tissue arrayer "Galileo TMA CK 3500" BioRep (Milan) until a complete TMA design was produced. TMA recipient blocks were baked at 42 <0> C for 2 h prior to sectioning. The TMA blocks were sectioned with 2-3 mm thickness using a waterfall microtome (Leica), and placed onto poly-L-lysinated glass slides for immunohistochemical analysis. For automated immunohistochemistry, glass slides were incubated for 30' min in 60° C., de-paraffinized in xylene (2×15 min) using the Bio-Clear solution (Midway. Scientific, Melbourne, Australia), and re-hydrated in graded alcohols. For antigen retrieval, slides were immersed 0.01 M Na-citrate buffer, pH 6.0 at 99° C. for 30 min Slides were placed in the Autostainer® (DakoCytomation) and endogenous peroxidase was initially blocked with 3% H2O2, for 5 min. Slides were then blocked in Dako Cytomation Wash Buffer containing 5% Bovine serum albumin (BSA) and subsequently incubated with mouse antibodies for 30' (dilution 1:200 in Dako Real™ dilution buffer). After washing with DakoCytomation wash buffer, slides were incubated with the goat anti-mouse peroxidase conjugated Envision® for 30 min each at room temperature (DakoCytomation). Finally, diaminobenzidine (DakoCytomation) was used as chromogen and Harris hematoxylin (Sigma-Aldrich) was used for counterstaining. The slides were mounted with Pertex® (Histolab).

The staining results have been evaluated by a trained pathologist at the light microscope, and scored according to both the percentage of immunostained cells and the intensity of staining. The individual values and the combined score (from 0 to 300) were recorded in a custom-tailored database. Digital images of the immunocytochemical findings have been taken at a Leica DM LB light microscope, equipped with a Leica DFC289 color camera.

Results

Figure 1:
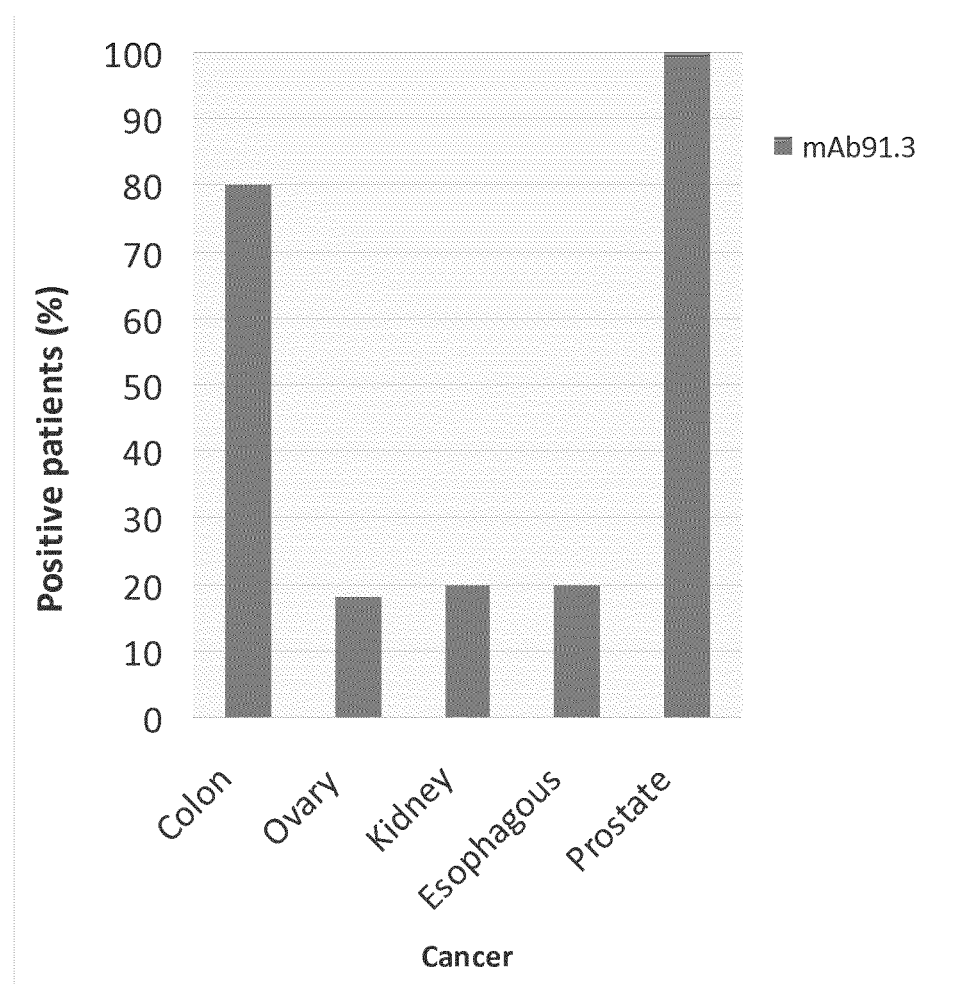
FIG. 1. Frequency of positive IHC staining of colon, ovary, esophagus, kidney and prostate cancer using the anti-FAT1 monoclonal antibody mAb91.3.

The results from tissue profiling showed that a monoclonal antibody specific for human FAT1 mAb91.3 was strongly immunoreactive on tissues from colon cancer (approximately 80%), while no or poor reactivity was detected in corresponding normal samples. This monoclonal antibody also showed selective reactivity on ovary, esophagus and kidney cancers (approximately 18%, 20% and 20% of positive staining, respectively). Moreover, this monoclonal antibody also showed very strong reactivity on 100% of prostate cancer sample, with concomitant moderate reactivity on normal prostate tissues. The antibody staining accumulated at the plasma membrane of tumor cells. FIG. 1 shows the frequency of IHC positive staining with mAb91.3, based on analysis of 50 patients/tumor. Representative examples of microscopic enlargements of colon and prostate tissue samples stained by the anti-FAT1 monoclonal antibody are reported in FIGS. 2-3. Other antibodies towards FAT1 were used in the tissue profile analysis and these did not prove as much efficient as mAb91.3 to selectively recognize cancer tissues.

Based on this finding, the detection of FAT1 protein in tumor tissue samples can be associated with colon, ovary, esophagus, kidney and prostate tumors. Moreover, the FAT1 localization at the plasma membrane makes this protein a suitable target for anti-cancer therapies.

Example 2. Expression and Localization of FAT1 Protein in Cancer Cells

The expression and localization of FAT 1 protein in cancer cells was investigated using an anti-FAT1 monoclonal antibody to confirm that FAT1 is expressed by cancer cell lines derived from the human cancers found positive in the IHC screening. Moreover, FAT1 surface localization surface was verified to confirm that FAT1 could be exploited as therapeutic target of anti-cancer therapies. FAT-1 affinity ligands, such as small molecules or antibodies, able to recognize the protein on the cell surface can be developed as novel therapeutic antigens. Finally the association of FAT1 with cell-derived exosomes was investigated to assess whether FAT1 is released by cancer cells and could be detected in patients' biological fluids. This property would allow developing non-invasive diagnostic assays based on FAT1 detection. Moreover, exosomes could be exploited in vaccines based on the elicitation of antibody and T cell response against FAT1.

Methods

FAT1 expression was first assessed by WB on total extracts from a panel of colon cancer epithelial cell lines. In the analysis, cells were cultured in under ATCC recommended conditions, and sub-confluent cell monolayers were detached with PBS-0.5 mM EDTA and lysed by several freeze-thaw passages in PBS-1% Triton. Total protein extracts were loaded on SDS-PAGE ($2\times10^5$ cells/lane), and subjected to WB with anti-FAT1 specific antibodies.

To analyse the presence of FAT1 in cancer cell exosomes, exosomes were purified from 10 ml culture supernatant of different colon cancer cell lines using the Exoquick-TC purification kit (SBI). The exosomal pellet (corresponding to approximately $5\times10^6$ cells) were lysed with Laemmli buffer under reducing condition, loaded of SDS-PAGE gradient gels (NuPage 4-12% Bis-Tris gel, Invitrogen) under reducing conditions, and subjected to immunoblot with anti-FAT1 antibodies as described (see example 1). The culture supernatants deprived of exosomes were concentrated, loaded on the gel and analysed in parallel by immunoblot. The quality of the exosomal preparation was verified by probing the blots with antibodies specific for known exosomal markers (e.g. CD81) or exosome-associated proteins (e.g IFITM3).

Western blot was performed by separation of the protein extracts on pre-cast SDS-PAGE gradient gels (NuPage 4-12% Bis-Tris gel, Invitrogen) under reducing conditions, followed by electro-transfer to nitrocellulose membranes (Invitrogen) according to the manufacturer's recommendations. The membranes were blocked in blocking buffer composed of 1×PBS-0.1% Tween 20 (PBST) added with 10% dry milk, for 1 h at room temperature, incubated with the antibody diluted 1:2500 in blocking buffer containing 1% dry milk and washed in PBST-1%. The secondary HRP-conjugated antibody (goat anti-mouse immunoglobulin/HRP, Perkin Elmer) was diluted 1:5000 in blocking buffer and chemiluminescence detection was carried out using a Chemidoc-IT UVP CCD camera (UVP) and the Western Lightning™ cheminulescence Reagent Plus (Perkin Elmer), according to the manufacturer's protocol.

FAT1 surface localization was assessed by Flow cytometry (FACS) and confocal microscopy analyses on colon and prostate cancer cells.

For Flow Cytometry analysis, cells ($2\times10^4$ per well) were pelleted in 96 U-bottom microplates by centrifugation at 200× g for 5 min at 4° C. and incubated for 1 hour at 4° C. with the appropriate dilutions of anti-FAT1-monoclonal antibody. The cells were washed twice in PBS-5% FCS and incubated for 20 min with the appropriate dilution of R-Phycoerythrin (PE)-conjugated secondary antibodies (Jackson Immuno Research, PA, USA) at 4° C. After washing, cells were analysed by a FACS Canto II flow cytometer (Becton Dickinson). Data were analyzed with FlowJo 8.3.3 program.

For confocal microscopy, cells were plated on glass cover slips and after 48 h were washed with PBS and fixed with 3% formaldehyde solution in PBS for 20 min at RT. Then, after extensive washing in PBS, the cells were incubated with the anti-FAT1 antibodies overnight at 4° C. (1:200) with or without a previous permeabilization step with 0.01% BriJ96® (Fluka). Cells were then stained with Alexafluor 488-labeled goat anti-mouse antibodies (Molecular Probes). DAPI (Molecular Probes) was used to visualize nuclei. The cells were mounted with glycerol plastine and observed under a laser-scanning confocal microscope (LeicaSPS).

Results

FAT1 expression was confirmed in a panel of colon tumor cell lines, including HCT15, HCT116, HCC2998, Colo205, HT29 and Caco2, examples of which are given in FIG. 4. In all tested cell lines a peculiar protein pattern was observed in which different high molecular weight protein bands (around 200 kDa and higher mass) were detected by the antibody, and other proteins species of lower molecular weight (ranging from 100 to 30 kDa), that could correspond to the annotated FAT1 isoforms as well as processed form of it.

FAT1 protein was also clearly detected in exosomes derived from cancer cells using specific antibodies (FIG. 5) whereas it was marginally detected in the exosome-free supernatants. This indicated that the protein detected in the cell supernatant is mainly associated to exosomes. This result suggests that FAT1 could be released in biological fluids and could be detectable in patients' derived exosomes.

Figure 6A:
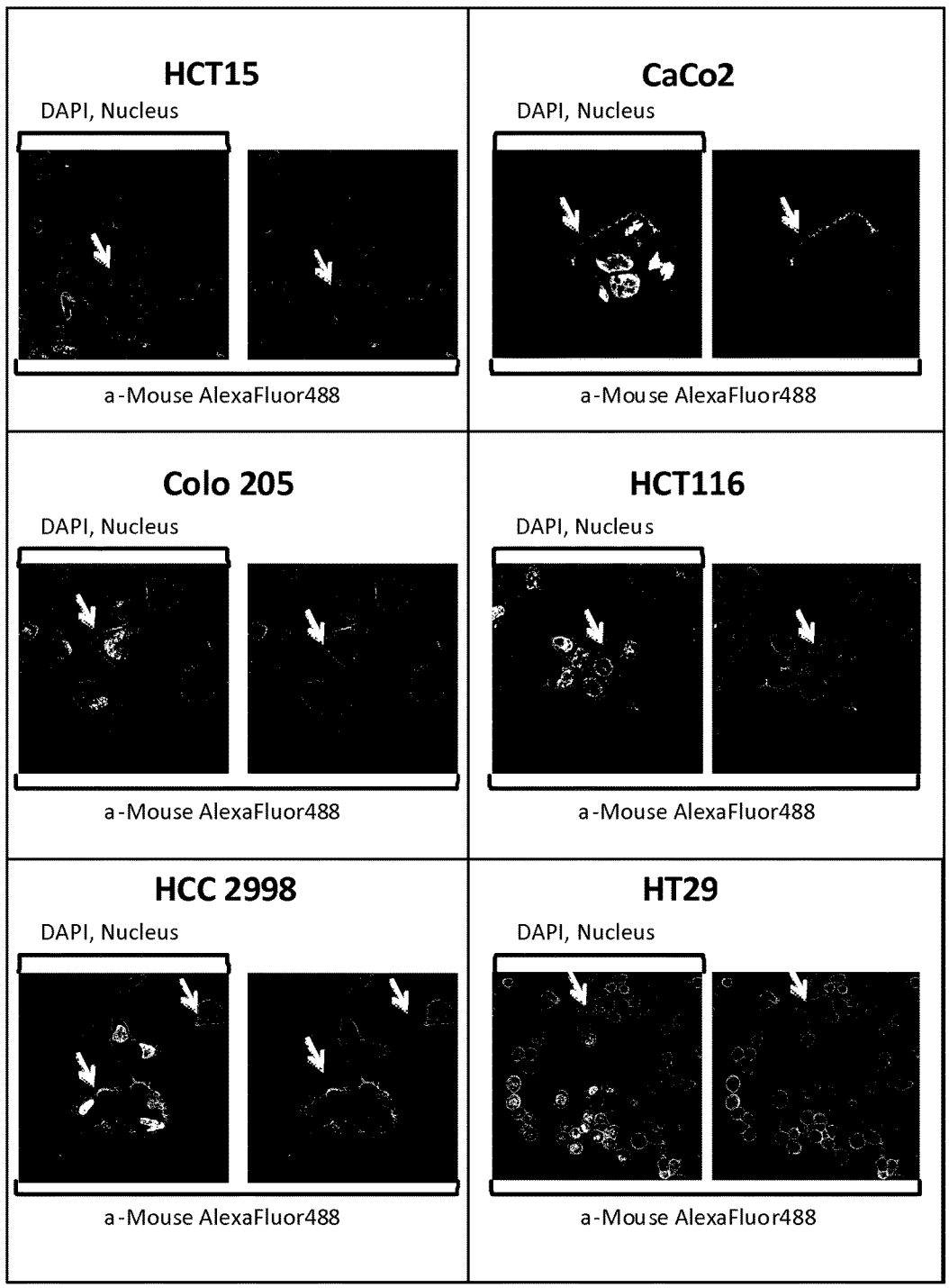
Figure 6B:
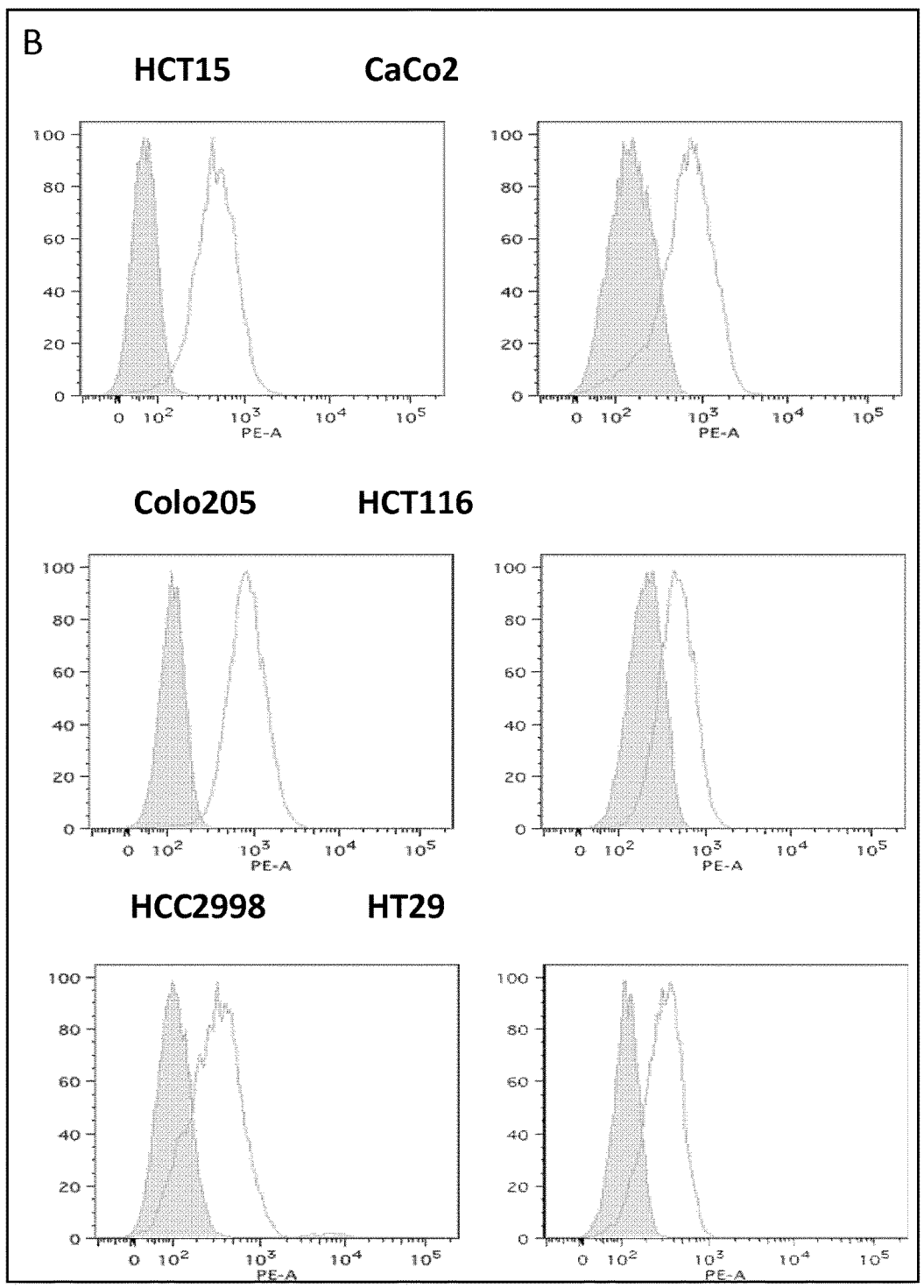

Surface staining of a panel of tumor cell lines with flow cytometry and confocal microscopy indicated that FAT1 protein is clearly exposed on the surface of colon and prostate cancer cells, as judged by the capability of the anti-FAT1 monoclonal antibody to bind the cell surface (FIG. 6). This evidence suggests that FAT1 could be exploited as therapeutic target of anticancer therapies.

Example 3. Confirmation of the Specificity of the Anti-FAT1 Antibody by Gene Silencing The specifity of the anti-FAT1 monoclonal antibody mAb91.3 showing selective cancer reactivity in IHC was further verified by specific FAT1 knock-down in FAT1 positive tumor cell lines by the siRNA technology and the knock-down of FAT1 expression was monitored at transcriptional and protein level.

Method

FAT1 expression was silenced in the HCT15 colon cell lines with two FAT1-specific siRNAs (10 nM) (whose target sequences are reported in the Table) using the HiPerfect transfection reagent (QIAGEN) following the manufacturer's protocol. As control, cells treated with equal concentrations of irrelevant siRNA (scrambled siRNA) were analysed in parallel. At different time points (ranging from 24 to 72 hours) post transfection, the reduction of gene transcription was assessed by quantitative RT-PCR (Q-RT-PCR) on total RNA, by evaluating the relative marker transcript level, using the beta-actin, GAPDH or MAPK genes as internal normalization control. Western blot was carried out on cells transfected with FAT1 or the scrambled siRNA and the reduced FAT1 protein expression was measured by Western blot with mAb91.3, using antibodies for beta-actin as normalization standard. Furthermore, the FAT1 disappearance from the cell surface was assessed with mAb91.3, using the surface marker CD81 as internal standard. Finally, FACS analysis of silenced cells was also extended to other two antibodies generated against FAT1 (Ab623 and Ab624) that did not react with cancer tissues.

Results

Figure 7A:
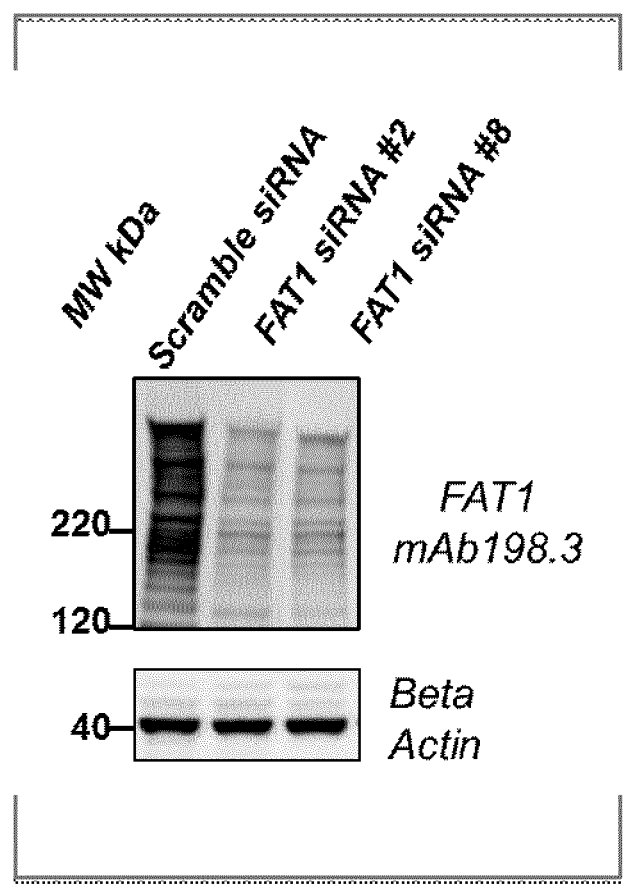
Figure 7B:
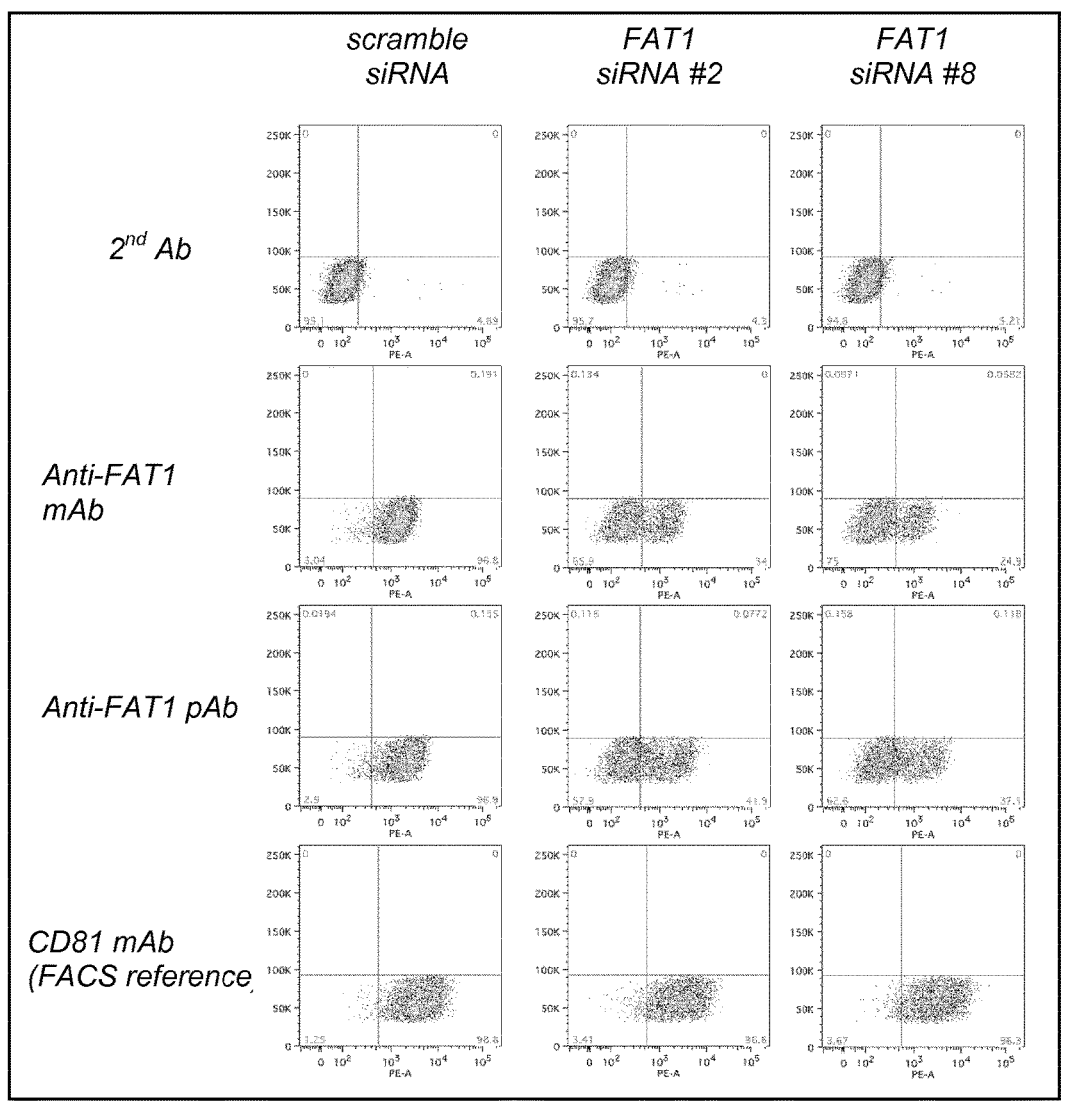

Gene silencing experiments with both FAT1-specific siRNA significantly reduced the marker transcripts, as determined by all Q-RT-PCR. A significant reduction of the FAT1 expression was clearly visible by Western blot (FIG. 7A). Flow cytometry analysis also showed the disappearance of FAT1 surface staining in silenced cells using mAb91.3 as well other two anti-FAT1 antibodies, whereas CD81 staining remained unchanged (FIG. 7B). These results confirmed that mAb91.3 and the two other antibodies unambiguously recognize FAT1 on the surface of cancer cells. Moreover, the data highlighted that mAb91.3, compared to other anti-FAT1 antibodies, has unique and unexpected properties to detect cancer tissues.

TABLE

| NCBI gene | siRNA Target Sequence | siRNA # |
|---|---|---|
| FAT1 | CAGGACGTGTATGATACTCTA (SEQ ID NO: 43) | #2 |
| | CAGGCTGGATTACAACTTTAA (SEQ ID NO: 44) | #8 |

Example 4. Internalization of the Anti-FAT1 Monoclonal Antibody mAb91.3 by Cancer Cells The ability of the anti-FAT1 monoclonal antibody to be internalized by cancer cells was assessed in different cancer model. Indeed, monoclonal antibodies able to be efficiently internalized by cancer cells are ideal candidate to generate ADC, in which they can be linked to therapeutic drugs, such as small molecules, toxins, radionucleotides, epigenetic agents and others.

Method

The ability of the anti-FAT1 antibody to be internalized was first assessed by flow cytometry, monitoring the kinetics by with the surface-bound antibody disappeared from the cell surface upon temperature shift from 0° C. to 37° C. In parallel, confocal microscopy was used to confirm the accumulation of antibody complexes in the intracellular milieu.

For Flow cytometry analysis Colo205 cells were incubated with the anti-FAT1 monoclonal antibody (10 micrograms/ml) for 30' at 4° C., as described (see Example 2) to allow antibody binding on the cell surface. Then cells were washed with PBS-5% FCS to remove unbound antibody and shifted to 37° C. At time points, cells were incubated for 20 min with the appropriate dilution of R-Phycoerythrin (PE)-conjugated secondary antibodies at 4° C. After washing, cells were analysed by a flow cytometer and the data were analyzed, as described.

For confocal microscopy analysis HCT15 cells were plated on microscope coverslips as described and after 48 h were washed with PBS. Cells were incubated with the anti-FAT1 monoclonal antibody mAb91.3 for 1 hour at 4° C. (10 micrograms/ml) and subsequently shifted at 37° C. Cells were then fixed with 10 minute incubation with 90% cold methanol and stained with Alexafluor 488-labeled goat anti-mouse antibodies. DAPI (Molecular Probes) was used to visualize nuclei. The cells were mounted with glycerol plastine and observed under a laser-scanning confocal microscope (LeicaSPS).

Results

Flow cytometry and confocal microscopy analyses showed that the anti-FAT1 antibody is able to bind the cells surface and upon temperature shift to 37° C. it disappears from the cell surface and accumulates in the intracellular milieu (FIG. 8) These results confirm that the anti-FAT1 antibody is efficiently internalized by cancer cells and indicate that the antibody is a suitable vehicle to drive therapeutic/cancer cytotoxic agents within cancer cells.

Example 5. Therapeutic Activity of the Anti-FAT1 Antibody in Mouse Colon Cancer Models Marker specific monoclonal antibodies able to selectively bind and reduce human cancers engrafted in appropriate mouse models can be developed as therapeutic agents either as naked antibody or as ADC. Such antibodies can be used in therapeutic treatment regimens of oncologic patients, to reduce the tumor burden in patients affected by primary or metastatic cancers. Moreover, they can be used in preventive treatments to prevent or delay the formation of cancer, for instance in the adjuvant therapy of patients subjected to surgery.

Method

The efficacy of the anti-FAT1 mAb91.3 against cancer growth was assessed in colon cancer xenograft mouse models in two experimental setting aimed at measuring the ability of the antibody to reduce tumor growth or delay tumor formation.

Therapeutic Setting.

The HCT15 and the HT29 human colon carcinoma cells ($5 \times 10^6$ cells) were injected subcutaneously into nude athymic mice. Mice (6 per group) bearing xenografts of approx. 60-100 mm$^3$ were administered i.v. of either mAb91.3 or the irrelevant mAb 61 (300 micrograms/dose, equal to approximately 12 mg mAb per Kg of animal weight, 2 doses per week). The specificity of the antibody binding to the tumor was also assessed by injecting mice with Near Infrared (NI) fluorescence-labeled antibodies (300 micrograms) followed by optical imaging 2-3 days after mAb injection. Tumor growth measured with a caliper over approximately a 2 week-period. Mice bearing tumors higher than 700 mm$^3$ were sacrificed.

Preventive Setting.

The HCT15 human colon carcinoma cells ($5\times10^6$ cells) were injected subcutaneously into nude athymic mice (8 per group). Mice were administered i.v. with repeated doses of either mAb91.3 or the irrelevant mAb61 (IgG1k isotype control) (300 micrograms/dose, equal to approximately 12 mg mAb per Kg of animal weight, 2 doses per week starting from day −1 before cancer injection). Tumor growth measured with a caliper over a 3 week-period.

Results

The anti-FAT1 monoclonal antibody was able to bind colon cancer xenograft (FIG. 9A) and showed negligible background distribution in other animal anatomical districts. Moreover, the anti-FAT1 antibody was able to significant reduce growth rate in both HCT15 and HT29 colon cancer (FIGS. 9A and 9B) both in the therapeutic and the preventive experimental settings.

Example 6. Therapeutic Activity of the Anti-FAT mAb91.3 in an Indirect Antibody-Drug Conjugate mAbs can be used as naked molecules or conjugated with cell payloads (radioisotopes, drugs or toxins) to direct kill tumor cells or to activate pro-drugs specifically within the tumors. These antibody-drug conjugates (ADC) can deliver a toxic load selectively to the tumor site while normal tissues are generally spared. ADC are of particular interest in that their therapeutic efficacy is stronger than that of naked antibodies.

The most important property of antibodies to be used for the generation of ADC is their specificity for cancer cells, and the ability to be efficiently internalized by them so as to deliver the toxic compound in the intracellular compartment.

In order to minimize toxicity, conjugates are usually engineered based on molecules with a short serum half-life (e.g. the use of IgG3 or IgG4 isotypes). Different linker chemistry can be used to link the cell payload to the antibody. Labile linkers allow a rapid dissociation of the drug from the antibody within the cells (e.g. pH sensitive linkers dissociates from the antibody at pH below 6, allowing the drug release within endosomes or lysosomes). Stable linkers require complete proteolytic digestion of the ADC to release the cytotoxic drug as the active metabolite. An in vitro assay generally used to predict the potential of an antibody as ADC exploits the use of a secondary antibody conjugated to saporin, the most potent of the plant ribosome-inactivating proteins. In this assay the primary monoclonal antibody is incubated with cancer cells to allow surface binding. Afterwards a saporin-conjugated secondary antibody is added that recognizes the cell-bound primary antibody. After shift to 37° C. the immunocomplex is internalized in the cell and cell death is induced.

Method

HCT15 cells were seeded on 96 w plates (2000 cells per well) and incubated 4° C. for 30' with mAb91.3 at concentrations ranging from 1 to 40 micrograms/ml. After washing, cells were incubated for 30' with a saporin-conjugated secondary antibody (FABZAP system, ATS) according to the manufacturer's recommendation and shifted at 37° C. for 72 hours to allow internalization and cell killing. The percentage of killing was evaluated with the MTT assay. Results are from triplicate samples.

Results

The anti-FAT1 mAb91.3 incubated in the presence of a saporin-conjugated secondary showed a significant killing on HCT15 cancer cells, indicating that this antibody has a high potential for the generation of ADC (see FIG. 10).

Example 7. Identification of Monoclonal Antibodies Reactive with Peculiar FAT1 Epitopes Able to be Bind the Surface of Cancer Cells and Internalized Upon Binding To reinforce the validity of FAT1 as potential target of monoclonal antibody therapy a panel of anti-FAT1 monoclonal antibodies were screened in search for other antibodies that recognize the FAT1 region exposed on the surface of cancer cells and are internalized by cancer cells upon binding.

Method

A panel of monoclonal antibodies secreted by distinct hybridoma cells able to recognize FAT1 in ELISA were tested for the ability to recognize colon cancer cells in Western blot and FACS (see Western blot and FACS methods described in Example 2) and of being internalized upon binding (see Internalization methods described in Example 4).

Results

The FACS selection process allowed to identify another anti-FAT1 monoclonal antibody (namely mAb91.4) able to bind the surface of HCT15 and Colo205 colon cancer cells and to internalize upon temperature shift to 37° C. (FIG. 11).

Example 8. Identification of the FAT1 Region Recognized by the Monoclonal Antibodies and Epitope Mapping The epitopes specifically recognized by monoclonal antibodies on cancer cells can be exploited as diagnostic tools for the development of diagnostic assay. Moreover, they can be used as targets for the development of affinity drugs with therapeutic properties. Given the high molecular weight of FAT1, a selection of the FAT1 regions recognized by mAb91.3 and mAb91.4 was done by transfecting cells with plasmids encoding overlapping FAT1. These regions were further subcloned in smaller fragments and expressed in a recombinant forms and analyzed by enzyme-linked immunosorbent assay (ELISA) and Western blot. Finally, overlapping peptides were generated and used to identify the antibody epitope/s. The specificity of the monoclonal antibodies for the target epitopes was demonstrated by peptide competition experiments in ELISA, FACS and IHC. Overall the results unambiguously led to the identification of the FAT1 epitopes recognized on the surface of cancer cells and detected in cancer tissues by IHC.

Method

Overlapping FAT1 cDNAs regions encoding approximately 600-800 amino acids were cloned in the mammalian expression vector pcDNA3.1 so as to generate a series of plasmids globally covering the FAT1 extracellular region from amino acid 1 to amino acid 4181. For cloning, cDNA were generated from pools of total RNA derived from Human testis, Human placenta, Human bone marrow, Human fetal brain, in reverse transcription reactions and the entire coding regions were PCR-amplified with specific primers pairs. PCR products were cloned into plasmid pcDNA3 (Invitrogen) so as to generate His6-V5 tagged fusions. HeLa and Hek-293T cells were grown in DMEM-10% FCS supplemented with 1 mM Glutamine were transiently transfected with preparation of the resulting plasmid and with the empty vector as negative control using the Lipofectamine-2000 transfection reagent (Invitrogen). After 48 hours, cells were collected and analysed by Western blot as described in Example 2, using the anti-FAT1 mAb91.3 or an anti-V5 antibody.

Shorter FAT1 domains covering Region A and Region B (see example before) were also cloned, used for transfection and analysed the ability of the mAb91.3 to recognize them in Western blot. Moreover, these FAT1 regions were expressed in recombinant form, purified from *E. coli* and used for ELISA. Finally, 25 mer peptides were obtained by chemical synthesis covering selected FAT1 regions and used for competition of the antibody binding in ELISA, FACS and IHC, thus leading to the unambiguous identification of the mAb91.3 target epitopes.

For ELISA competition experiments, ELISA plates (Nunc Maxisorp) were coated with 1 μg of the FAT1 recombinant proteins in PBS (pH 7.4) at 4° C. overnight. The plates were washed, treated for 1 h at 37° C. with PBS-1% BSA, and 100 μl aliquots of mAb91.3 at (10 micrograms/ml) in PBS-0.1% Tween were added to the wells in the presence of the 25 mer peptides at concentration ranging from 0.001 to 100 micrograms/ml. After incubation for 2 h at 37° C., plates were again washed and incubated for 1 h at 37° C. with alkaline-phosphatase conjugated goat anti-mouse IgG (Sigma) diluted 1:2500 in PBS-Tween. Thereafter 100 μl of PNPP substrate (Sigma) were added to the samples and incubated for 30 min at room temperature and optical densities were read at 405 nm.

For FACS competition, Colo205 and HCT15 cells were co-incubated with mAb91.3 in the presence of different concentrations of selected 25 mer peptides (ranging from 0 to 100 micrograms per ml) and the inhibition of surface binding was assessed by FACS, as described in Example 2, compared to samples incubated with an irrelevant peptide.

For IHC competition experiments, cancer tissues were co-incubated with mAb91.3 in the presence of selected 25 mer peptides (100 micrograms per ml) and residual antibody binding to cancer cells was assessed (see Method in Example 1).

Results

HeLa and HEK-293T were transfected with plasmids encoding overlapping FAT1 regions and their expression was first confirmed by Western blot using the anti-V5 antibody. Two positive FAT1 regions were recognized by mAb91.3 overlapping for 102 amino acids (Fragment A, encompassing the amino acid regions from amino acid 723 to amino acid 1352, and Fragment B encompassing the FAT1 region from amino acid 1246 to amino acid 1879) were recognized by the mAb91.3. Moreover, a shorter form of Fragment A lacking the region overlapping with Fragment B (referred as fragment A short) was also recognized by the antibody. This evidence indicates that, unexpectedly, this monoclonal antibody has two binding sites on FAT1 protein (FIG. 12). Fragment A-transfected cells were also recognized by mAb91.4, suggesting that mAb91.3 and mAb91.4 share at least in part the same epitopes.

HeLa and HEK-293T were also transfected with plasmids encoding shorter FAT1 regions included in Fragment A and Fragment B, which allowed to discriminate that the two antibody binding sites map on two distinct cadherin domains, namely Domain 8 (from amino acid 823 to amino acid 927—SEQ ID NO:28) and Domain 12 (from amino acid 1246 to 1352—SEQ ID NO:29). Both Domains 8 and 12 are included in the original Region A (SEQ ID NO:27) while Domain 12 is located in the overlapping region between Region A and Region B.

FAT1 recombinant proteins encompassing the two FAT1 cadherin Domain 8 and 12 were also recognized in ELISA by mAb91.3, further confirming antibody specificity. Afterwards, for a more accurate epitope identification, a panel of overlapping peptides were designed on Domain 8 and Domain 12 and used in ELISA and FACS competition experiments. Among them, three 25 mer peptides encompassing the FAT1 regions were recognized by mAb91.3 in ELISA. Among them, Peptide 1 and 2 map on the cadherin Domain 12 and partially overlap, whereas peptide 3 maps on the Domain 8. The peptide sequences are reported below.

```
                                      (SEQ ID NO: 30)
    Peptide 1:    REPLYHVIATDKDEGPNAEISYSIE (SEQ ID NO: 31)
    Peptide 2:    YHVIATDKDEGPNAEISYSIEDGNE (SEQ ID NO: 32)
    Peptide 3:    IQVEATDKDLGPNGHVTYSIVTDTD
```

ELISA competition experiments showed that the binding of mAb91.3 on the two FAT1 recombinant domains was almost abolished by competition with each of the three peptides.

Similarly, FACS competition experiments showed that the antibody ability to bind the surface of Colo205 and HCT15 cells was dramatically reduced by competition the three peptides (FIG. 13).

IHC competition experiment was carried out with peptide 1 on colon cancer tissue. Under this condition the antibody recognition of cancer cells was almost abolished (FIG. 14).

Overall, results demonstrate that mAb91.3 and mAb91.4 epitopes are included Region A. For mAb 91.3, a more precise epitope mapping showed that its target epitopes are located in peptides 1, 2 and 3. The three peptides show differences in their primary sequence and have amino acid identity between 84 to 48%. Moreover, shorter peptides encompassing the central conserved region are not able to compete for the antibody binding. Thus, a plausible hypothesis is that they have a structural similarity and that anti-FAT1 monoclonal antibodies recognize a structural motif in common between them.

(see annexed sequence listings).

Example 9. Sequencing of mAb91.3 and mAb91.4

Complementarity determining regions (CDRs) are the most variable part of antibody molecules determining the diversity of these molecules, and represent a unique feature of the antibody. CDRs are the antibody regions that complement an antigen's shape and determine the antibody specificity for given antigens. Differences in the CDRs are also responsible for the affinity constant of the monoclonal antibodies for their epitopes. RNA was isolated from the hybridoma clone secreting mAb91.3 and subjected to RT-PCR using degenerated primers able to amplify the variable regions of heavy and light chains (23). Since the subclass of mAb91.3 and mAb91.4 is IgG1k, the following primers were used:

Heavy Chain:

```
                                      (SEQ ID NO: 45)
    IgG1:HC       ATAGACAGATGGGGGTGTCGTTTTGGC (SEQ ID NO: 47)
    MH1           SARGTNMAGCTGSAGSAGTC (SEQ ID NO: 48)
    MH2           SARGTNMAGCTGSAGSAGTCWGG
```

Light Chain:

```
                                         (SEQ ID NO: 46)
    Kc         GGATACAGTTGGTGCAGCATC (SEQ ID NO: 49)
    Mk         GAYATTGTGMTSACMCARWCTMCA
```

The amplification products were sequenced and the variable regions were analyzed using three different sequence analysis tools: Ig-BLAST http://www.ncbi.nlm.nih.gov/igblast/ (Ye J[1], Ma N, Madden T L, Ostell J M.) IgBLAST: an immunoglobulin variable domain sequence analysis tool. Nucleic Acids Res. 2013 July; 41(Web Server issue):W34-40. doi: 10.1093/nar/gkt382. Epub 2013 May 13.), V-BASE2 http://www.vbase2.org/ (Retter I, Althaus H H, Münch R, Müller W: VBASE2, an integrative V gene database. Nucleic Acids Res. 2005 Jan. 1; 33(Database issue):D671-4) and the fully integrated antibody discovery system AbYsis http://www.bioinforg.uk/abysis.

For either of the two monoclonal antibodies, sets of CDRs were determined with the three predictors.

The CDR and variable region sequences of mAb91.3 and mAb91.4 are identified in the annexed sequence listing, wherein:
  mAb 91.3 heavy chain CDRs: SEQ ID NOs:17-19
  mAb 91.3 light chain CDRs: SEQ ID NOs: 20-22
  mAb 91.3 heavy chain: SEQ ID NO:25
  mAb 91.3 light chain: SEQ ID NO:26
  mAb 91.4 heavy chain CDRs: SEQ ID NOs: 37-39
  mAb 91.4 light chain CDRs: SEQ ID NOs:40-42
  mAb 91.4 heavy chain: SEQ ID NO:35
  mAb 91.4 light chain: SEQ ID NO:36

Example 10. Determination of the Affinity Constant of the Anti-FAT1 mAb91.3

Method

The kinetics of association and dissociation and the Dissociation constants of the anti-FAT1 mAb91.3 were determined using Surface Plasmon Resonance Analysis. Experiments were performed at 25° C. with a BIACORE T100 instrument (Biacore A B, Uppsala, Sweden). The recombinant FAT1 proteins were immobilised on a carboxymethylated dextran-coated (CM5) sensor chip by amine coupling. Briefly, a mixture of 0.2 M 1-ethyl-3-diaminopropyl-carbodiimide (EDC) and 0.05 M N-hydroxysuccinimide (NHS) was used for sensor chip surface activation. Proteins pre-concentrated in 0.01 M sodium acetate pH 3.5 were injected at concentration ranging from 2.5 and 5 µg/ml for 10 min and then 1 M ethanolamine pH 8.5 was used to block any remaining activated groups. mAb91.3 was diluted in HBS-EP+ buffer at different concentrations from 0.625 µg/ml to 5 µg/ml and injected for 120 s at a flow rate of 300 min on flow cell 2 and 3. HBS-EP+ buffer was run as control. Dissociation was followed for 450 sec, regeneration was achieved with a short pulse of glycine 10 mM pH2.0. $k_{on}$, $k_{off}$ and $K_D$ were calculated with the 1:1 Langmuir model using "BiaEvaluation 4.1".

Results mAb91.3 Dissociation constants ($K_D$) on FAT Domain 8 and 12, reported below, ranged from $10^{-8}$ to $10^{-9}$ M

| FAT Domain | ka (1/Ms) | kd (1/s) | KD (M) |
|---|---|---|---|
| Domain 8 | 3.29E+05 | 0.003132 | 9.52E−09 |
| Domain 12 | 3.89E+05 | 0.007075 | 1.82E−08 |

Example 11. Generation of a Recombinant Monoclonal Antibody Reproducing mAb91.3 Properties Recombinant monoclonal antibodies can be prepared in order to improve the characteristic and functions of antibodies. Changes in the variable region can be made in order to improve the antigen binding characteristics. Changes in the constant region can, in general, be made in order to improve the cellular process characteristics, such as ADCC activity, complement fixation, interaction with membranes, and other effector functions. Alterations can be made by standard recombinant techniques.

Moreover, recombinant monoclonal antibodies can be also prepared to confirm the specificity and molecular properties of the original antibodies produced by hybridoma clones.

Method

RNA was isolated from the hybridoma clone secreting mAb91.3 and subjected to RT-PCR using primers able to amplify the variable regions of heavy and light chains. These primers contain convenient modification of the immunoglobulin sequences in order to clone the variable regions in the light (Igk) and heavy (IgG2a) pFUSEss expression vectors (Invivogen). The plasmids obtained containing the variable regions of mAb91.3 were sequenced and the corrected clones (light and heavy chains) were used to cotransfect HEK-293T cells. Total cell extracts and culture supernatant were analyzed by Western blot using a secondary antibody to confirm the expression and correct assembly of the recombinant antibody.

Results

A recombinant mouse IgG2a antibody bearing the variable regions of mAb91.3 has been produced and detected both in total extracts and in the culture supernatant. The recombinant antibody produced in the cell culture supernatant was used in WB, ELISA and FACS analysis and confirmed its ability to bind the surface of Colo205 cells and to recognize specific FAT1 polypeptides.

Example 12. Immunogenicity of Cell-Derived Exosomes Bearing FAT1

Exosomes released by cancer cells can be used as antigens for vaccines, able to elicit strong immune responses. Cancer derived exosomes bearing FAT1 can be exploited for the development of vaccines against FAT1 positive cancer types, such as colon, ovary, esophagus, kidney and prostate.

Methods

Preparation of Exosomes for Immunization Studies

For immunization studies, exosomes from cell culture supernatants were isolated by differential centrifugation as described (24). Briefly, $1 \times 10^8$ HCT15 cells were cultured in DMEM-10% FCS until confluency in 18 175 cm$^2$ flasks until pre-confluence. For exosomes preparation, the culture medium was replaced with serum-free medium (PFHM-II Gibco-Life Technologies), cultured for 24 h and then centrifuged at 200×g for 10 min (pellet P1). The supernatant was collected and centrifuged twice at 500 g for 10 min (pellet P2). The second supernatant was sequentially centrifuged at 2,000×g twice for 15 min (pellet P3), once at 10,000×g for 30 min (pellet P4), and once at 70,000×g for 60 min (pellet P5), using a SW28 rotor (Beckman instruments, Inc.). The cellular pellet P1 was solubilized in 1 ml of C-RIPA buffer (50 mM Tris-HCl pH7.5, 150 mM NaCl, 1% Nonidet P-40; 2 mM EGTA, 1 mM orthovanadate, 0.1% SDS, 0.5% Na-deoxycholate, 1 mM phenyl-methane-sulphonylfluoride, 10 μg/ml leupeptin, 10 μg/ml aprotinin) while each of the supernatant-derived pellets P2-P5 were solubilized in 0.5 μl of the same buffer. After clarification, the protein concentration of each sample was determined by Bradford.

As quality controls of the exosomal preparation, 20 μg of P1 extract and 10 μg of P2-P5 extracts (corresponding to approximately $2 \times 10^5$ and $2 \times 10^7$ cells, respectively) were loaded on SDS-PAGE (4-12%) and analyzed by Western blot with antibodies targeting the exosomal marker CD81. Moreover, the presence of FAT1 in exosomes was also assessed by Western blot as described.

Immunizations

5/6 week old CD1 outbred female mice (5 mice per group) were immunised intra-peritoneally at days 1, 14 and 28 with exosomes (15 micrograms, in 100 microliters) formulated with an equal volume of Alum Hydroxide as adjuvant at the final concentration of 3 mg/ml. Two weeks after the last immunization mice were bled and sera from individual mice were pooled.

ELISA Analysis

Total IgG titers elicited by immunizing mice with exosomes was tested on two

FAT1 recombinant domains covering the protein cadherin domains 7-10 and 11-12 (Domain 7-10 from amino acid 723 to amino acid 1148; Domain 11-12 regions from amino acid 1136 to amino acid 1352) as proteins were assayed by enzyme-linked immunosorbent assay (ELISA). Individual wells of micro-ELISA plates (Nunc Maxisorp) were coated with 1 μg of each recombinant protein in PBS (pH 7.4) at 4° C. overnight. The plates were washed, treated for 1 h at 37° C. with PBS—1% BSA, and 100 μl aliquots of anti-sera towards exosomes, at different serial dilutions in PBS—0.1% Tween, were added to the wells. After incubation for 2 h at 37° C., plates were again washed and incubated for 1 h at 37° C. with alkaline-phosphatase conjugated goat anti-mouse IgG (Sigma) diluted 1:2500 in PBS-Tween. Thereafter 100 μl of PNPP (Sigma) were added to the samples and incubated for 30 min. at room temperature. Optical densities were read at 405 nm and the serum-antibody titers were defined as the serum dilution yielding an OD value of 0.5.

Results

To verify the ability of the FAT1-bearing exosomes to elicit high antibody titers against FAT1, CD1 mice were mice immunized with the combination exosomes (15 micrograms) formulated in Alum Hydroxide. Sera collected after the last immunization were pooled and analyzed by ELISA on plates coated with FAT1 recombinant proteins. As shown in FIG. 15, exosomes induced high antibodies titers against both recombinant FAT1 domains. During the entire experiments mice did not showed any evident sign of toxicity or pain. Results confirm that that the FAT1-Exosomes formulation is safe and highly immunogenic, thus could be exploited for as candidate antigen for anticancer vaccines.

REFERENCES

1. Adams G. P. and Weiner L. M. (2005) Monoclonal antibody therapy cancer. Nat Biotechnol. 23:1147-1157.
2. Yang C. & Robbins D. B. (2011) The role of tumor-derived exosomes in cancer pathogenesis. Clinical and Developmental Immunology, doi:10.1155/2011/842849).
3. Wolfers J, Lozier A, Raposo G, et al. Tumor-derived exosomes are a source of shared tumor rejection antigens for CTL cross-priming. Nature Medicine. 2001; 7(3):297-303).
4. Bu N, Wu H, Sun B, et al. Exosome-loaded dendritic cells elicit tumor-specific CD8(+) cytotoxic T cells in patients with glioma. Journal of Neuro-Oncology. 104(3):659-667).
5. Xiu F, Cai Z, Yang Y, Wang X, Wang J, Cao X. Surface anchorage of superantigen SEA promotes induction of specific antitumor immune response by tumor-derived exosomes. Journal of Molecular Medicine. 2007; 85 (5): 511-521.
6. Anderson, L., and Seilhamer, J. (1997). A comparison of selected mRNA and protein abundances in human liver. Electrophoresis 18: 533-537.
7. Chen, G., Gharib, T. G., Wang, H., Huang, C. C., Kuick, R., Thomas, D. G., Shedden, K. A., Misek, D. E., Taylor, J. M., Giordano, T. J., Kardia, S. L., Iannettoni, M. D., Yee, J., Hogg, P. J., Orringer, M. B., Hanash, S. M., and Beer, D. G. (2003) Protein profiles associated with survival in adenocarcinoma. Proc. Natl. Acad. Sci. U. S. A 100: 13537-13542.
8. Ginestier, C., Charafe-Jauffret, E., Bertucci, F., Eisinger, F., Geneix, J., Bechlian, D., Conte, N., Adelaide, J., Toiron, Y., Nguyen, C., Viens, P., Mozziconacci, M. J., Houlgatte, R., Birnbaum, D., and Jacquemier, J. (2002) Distinct and complementary information provided by use of tissue and DNA microarrays in the study of breast tumor markers. Am. J. Pathol. 161:1223-1233.
9. Gygi, S. P., Rochon, Y., Franza, B. R., and Aebersold, R. (1999) Correlation between protein and mRNA abundance in yeast. Mol. Cell. Biol. 19, 1720-1730.
10. Nishizuka, S., Charboneau, L., Young, L., Major, S., Reinhold, W. C., Waltham, M., Kouros-Mehr, H., Bussey, K. J., Lee, J. K., Espina, V., Munson, P. J., Petricoin, E., III, Liotta, L. A., and Weinstein, J. N. (2003) Proteomic profiling of the NCI-60 cancer cell lines using new high-density reverse-phase lysate microarrays. Proc. Natl. Acad. Sci. U.S.A. 100, 14229-14234.
11. Tyers, M., and Mann, M. (2003) From genomics to proteomics. Nature 422: 193-197.
12. Ivan Hateren N J, Das R M, Hautbergue G M, Borycki A G, Placzek M and Wilson S A: FatJ acts via the Hippo mediator Yap1 to restrict the size of neural progenitor cell pools. Development 138: 1893-1902, 2011.
13. Moeller M J, Soofi A, Braun G S, et al: Protocadherin FAT1 binds Ena/VASP proteins and is necessary for actin dynamics and cell polarization. EMBO J 23: 3769-3779, 2004.
14. Nakaya K, Yamagata H D, Arita N, et al: Identification of homozygous deletions of tumor suppressor gene FAT in oral cancer using CGH-array. Oncogene 26: 5300-5308, 2007.
15. Chosdol K, Misra A, Puri S, et al: Frequent loss of heterozygosity and altered expression of the candidate tumor suppressor gene "FAT" in human astrocytic tumors. BMC Cancer 9: 5, 2009.
16. Lee S, Stewart S, Nagtegaal I, et al: Differentially expressed genes regulating the progression of ductal carcinoma in situ to invasive breast cancer. Cancer Res 72: 4574-4586, 2012.
17. Morris L G, Kaufman A M, Gong Y, Ramaswami D, Walsh L A, Turcan Ş Eng S, Kannan K, Zou Y, Peng L, Banuchi V E, Paty P, Zeng Z, Vakiani E, Solit D, Singh B, Ganly I, Liau L, Cloughesy T C, Mischel P S, Mellinghoff I K, Chan T A. Recurrent somatic mutation of FAT1 in multiple human cancers leads to aberrant Wnt activation. Nat Genet. 2013 45:253-61. doi: 10.1038/ng.2538.

18. Sadeqzadeh E, de Bock C E, Zhang X D, Shipman K L, Scott N M, Song C, Yeadon T, Oliveira C S, Jin B, Hersey P, Boyd A W, Burns G F, Thorne R F. Dual processing of FAT1 cadherin protein by human melanoma cells generates distinct protein products. J Biol Chem. 2011 Aug. 12; 286(32):28181-91. doi: 10.1074/jbc.M111.234419.
19. de Bock C E, Ardjmand A, Molloy T J, et al: The Fat1 cadherin is overexpressed and an independent prognostic factor for survival in paired diagnosis-relapse samples of precursor B-cell acute lymphoblastic leukemia. Leukemia 26: 918-926, 2012.
20. Settakorn J, Kaewpila N, Burns G F and Leong A S: FAT, E-cadherin, β-catenin, HER 2/neu, Ki67 immuno-expression, and histological grade in intrahepatic cholangiocarcinoma. J Clin Pathol 58: 1249-1254, 2005.
21. Kononen J, Bubendorf L, Kallioniemi A, Barlund M, Schraml P, Leighton S, Torhorst J, Mihatsch M J, Sauter G, Kallioniemi O P. Tissue microarrays for high-throughput molecular profiling of tumor specimens. (1998) Nat Med. 4:844-7.
22. Kallioniemi O P, Wagner U, Kononen J, Sauter G. (2001) Tissue microarray technology for high-throughput molecular profiling of cancer. Hum Mol Genet. 10:657-62.
23. Wang, Z. Raifu M, Howard M, Smith L, Hansen D, Goldsby R, Ratner D (2000) Universal PCR amplification of mouse immunoglobulin gene variable regions: the design of degenerate primers and an assessment of the effect of DNA polymerase 3' to 5' exonuclease activity. *Journal of immunological methods* 233, 167-77.
24. Raposo G, Nijman H W, Stoorvogel W, Liejendekker R, Harding C V, Melief C J, Geuze H J (1996) B lymphocytes secrete antigen-presenting vesicles. J Exp Med 183:1161-1172.

---

The invention claimed is:

1. An isolated monoclonal antibody or fragment thereof which specifically binds the FAT1 protein, wherein the heavy- and light-chain variable regions of said antibody or fragment thereof contain complementarity determining regions 1, 2 and 3 (CDR-H 1-3 and CDR-L 1-3, respectively) and:
said CDR-H 1-3 comprises the amino acid sequences set forth in SEQ ID NOs:17, 18 and 19, respectively; and
said CDR-L 1-3 comprises the amino acid sequences set forth in SEQ ID NOs:20, 21 and 22, respectively.

2. An isolated monoclonal antibody or fragment thereof which specifically binds the FAT1 protein, wherein the heavy- and light-chain variable regions of said antibody or fragment thereof contain complementarity determining regions 1, 2 and 3 (CDR-H 1-3 and CDR-L 1-3, respectively) and:
said CDR-H 1-3 comprises the amino acid sequences set forth in SEQ ID NOs:37, 38 and 39, respectively; and
said CDR-L 1-3 comprises the amino acid sequences set forth in SEQ ID NOs:40, 41 and 42, respectively.

3. An antibody or fragment thereof according to claim 1, wherein said variable regions contain heavy and light chains set forth in SEQ ID NO:25 and SEQ ID NO:26, respectively.

4. An antibody or fragment thereof according to claim 2, wherein said variable regions contain the heavy and light chains set forth in SEQ ID NO:35 and SEQ ID NO:36, respectively.

5. An antibody according to claim 1, containing a constant region of a human IgG1, IgG2, IgG3 or Ig4.

6. The isolated monoclonal antibody or fragment thereof according to claim 1 which specifically binds to an epitope of the FAT1 protein, wherein said epitope is selected from SEQ ID NOs:30, 31 and 32.

7. An antibody according to claim 1, which is a IgG, IgM, IgA, IgD or IgE antibody.

8. An antibody fragment according to claim 1, which is a Fab, F(ab')2, Fv, ScFv or single-chain antibody fragment.

9. An antibody according to claim 1, which is one of the following: a humanized antibody, a chimeric antibody, or a diabody.

10. An antibody or fragment thereof according to claim 1, which is conjugated to an antitumor compound.

* * * * *